(12) United States Patent
Sidduri

(10) Patent No.: US 10,815,244 B2
(45) Date of Patent: Oct. 27, 2020

(54) ISOIDIDE DERIVATIVES AND METHODS OF MAKING AND USING SAME

(71) Applicant: Rutgers, the State University of New Jersey, New Brunswick, NJ (US)

(72) Inventor: Achyutharao Sidduri, Newark, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/551,293

(22) Filed: Aug. 26, 2019

(65) Prior Publication Data

US 2019/0382414 A1 Dec. 19, 2019

Related U.S. Application Data

(62) Division of application No. 15/250,336, filed on Aug. 29, 2016, now abandoned.

(60) Provisional application No. 62/214,519, filed on Sep. 4, 2015.

(51) Int. Cl.
| | |
|---|---|
| *C07D 493/00* | (2006.01) |
| *A61K 31/34* | (2006.01) |
| *A61K 31/4709* | (2006.01) |
| *C07D 519/00* | (2006.01) |
| *C07D 493/04* | (2006.01) |
| *A61K 31/506* | (2006.01) |
| *A61K 31/513* | (2006.01) |
| *A61K 31/517* | (2006.01) |
| *A61K 31/519* | (2006.01) |

(52) U.S. Cl.
CPC ............ *C07D 493/04* (2013.01); *A61K 31/34* (2013.01); *A61K 31/4709* (2013.01); *A61K 31/506* (2013.01); *A61K 31/513* (2013.01); *A61K 31/517* (2013.01); *A61K 31/519* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 2006/0069077 A1* | 3/2006 | Rice | C07D 239/94 514/183 |
| 2010/0311721 A1* | 12/2010 | Stadtmueller | C07D 519/00 514/213.01 |
| 2011/0288071 A1* | 11/2011 | Stadtmueller | C07D 239/47 514/211.05 |

* cited by examiner

*Primary Examiner* — Savitha M Rao
*Assistant Examiner* — Gregg Polansky
(74) *Attorney, Agent, or Firm* — Saul Ewing Arnstein & Lehr LLP; Domingos J. Silva

(57) ABSTRACT

The present disclosure relates to compounds having an improved solubility thereby increasing their bioavailability, lower dosages, etc. The target compounds, may include but are not limited to, macrophage migration inhibitory factor (MIF) inhibitors, epidermal growth factor receptor (EGRF) inhibitors, kinase inhibitors and prodrugs of alpha4 beta1 and alpha4 beta7 integrin antagonists. An illustrative compound is shown below:

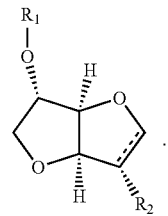

9 Claims, No Drawings

ISOIDIDE DERIVATIVES AND METHODS OF MAKING AND USING SAME

CLAIM OF PRIORITY

This application claims priority to U.S. application Ser. No. 15/250,336 filed on Aug. 29, 2016 which claims priority to U.S. Application 62/214,519 filed on Sep. 4, 2015, the contents of which are herein fully incorporated by reference in its entirety.

FIELD OF THE EMBODIMENTS

The field of the embodiments of the present invention relate to compounds having improved solubility thereby increasing their bioavailability. In particular, the present invention relates to the synthesis and applications of such target compounds.

BACKGROUND OF THE EMBODIMENTS

Isosorbide is a heterocyclic compound derived from glucose. Isosorbide has two isomers, namely two diastereomers, isomannide and isoidide, which belong to a class of compounds called 1,4;3,6-dianhydrohexitols. Isosorbide is essentially two fused tetrahydrofuran rings having a cis-arrangement at the ring junction, providing for a wedge-shaped molecule. The compound bears two hydroxyl groups, one at $C_6$ having an exo-orientation with respect to the wedge-shaped molecule, and the other at $C_3$ having the endo-orientation. This spatial relationship is what facilitates the intramolecular hydrogen bonding with the oxygen atom of the neighboring tetrahydrofuran ring (see below).

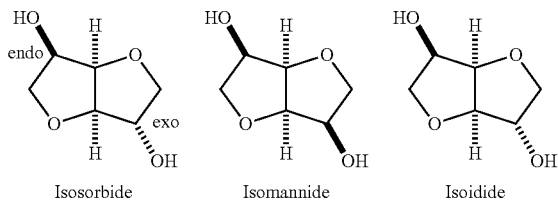

Isosorbide    Isomannide    Isoidide

Overall, and in part to its derivation from starches, isosorbide is highly stable, non-toxic, inexpensive, and commercially available in large quantities. Moreover, it bears two hydroxyl groups, which described below, allow further chemical modification of the isosorbide core. Isosorbide is thus an attractive and versatile chemical platform for many in academia and industry research.

Isosorbide and its derivatives have been utilized in polymer materials for, amongst others, the synthesis of biodegradable polymers, plasticizers, solvents, and surfactants. In other more limited usages, isosorbide and use of its derivatives have been reported in the medical field with the exception of isosorbide mononitrate, which has seen prominence in the pharmaceutical industry. Some of the other more limited medical applications include, but are not limited to, uses as a diuretic and in treating glaucoma. Other medications derived from isosorbide, include isosorbide dinitrate which, along with isosorbide mononitrate, are used to treat angina pectoris. Other isosorbide-based medicines are used as osmotic diuretics and for treatment of esophageal varices. Further, isosorbide dinitrate and hydralazine are the two components of the anti-hypertensive drug isosorbide dinitrate/hydralazine.

Notwithstanding the above, many derivatives of isosorbide (Isoidide, 3-exo and 6-exo substitution) are very difficult to make using conventional approaches. In practice, one use the disparate reactivity of the two hydroxyl groups (endo and exo) of isosorbide, to selectively react one of isosorbide's two hydroxyl groups with an introduced group. For example, under the purview of the present invention, the endo hydroxyl group may be selectively reacted with active phenols or carboxylic acids under slightly modified Mitsunobu reaction conditions without touching, or reacting, the exo hydroxyl group. The regioselective synthesis of this kind of mono substitution ether derivatives in one step has yet to be reported in the literature.

Although there is a different chemical reactivity for two hydroxyl groups with endo and exo orientations, there has been limited success in making selective mono substituted isosorbide derivatives without protection, with the exception of acetylation in the presence of metal salts such as lead oxide (Synthesis, 1987, 174-176). The alkylation, benzylation (Carbohydrate Research, 1994, 261, 255-266), esterification (Synthesis, 1989, 610-612), tosylation (Can. J. Chem., 1960, 38, 136-140), silylation or etherification under Mitsunobu reaction conditions (Synlett, 2003, 11, 1683-1687, Tetrahedron, 1999, 55, 10713-10734) of isosorbide produced a mixture of endo or exo mono-substituted derivatives with some extent bis-derivative (endo, exo). Whereas, the chemical reactivity of both hydroxyl groups of isomannide or isoidide are difficult to differentiate for selective chemical reactions.

The present application provides for an invention and various embodiments that describes the selective etherification or esterification of the endo hydroxyl group of isosorbide without touching the exo hydroxy group under slightly modified Mitsunobu reaction conditions (Synthesis, 1981, 1) that provide the derivatives of (3S,3aR,6S,6aR)-2,3,3a,5,6,6a-hexahydrofuro[3,2-b]furan-3,6-diol (isoidide core). The present application also describes this chemical reaction for the synthesis of MIF (macrophage migration inhibitory factor) inhibitors, EGFR (epidermal growth factor receptor) inhibitors, kinase targeting compounds, and prodrugs of alpha4 beta1 and alpha4 beta7 integrin antagonists.

SUMMARY OF THE EMBODIMENTS

One aspect of this invention is the provision of compounds, compositions, and kits for the improved solubility of target compounds, including but not limited to, macrophage migration inhibitory factor (MIF) inhibitors, epidermal growth factor receptor (EGFR) inhibitors, kinase inhibitors, and prodrugs of alpha4 beta1 and alpha4 beta7 integrin antagonists. Such applications are contained under the purview of a compound of Formula I:

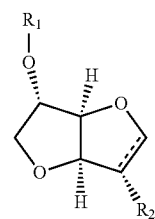

wherein:

R₁ is -aryl, -heteroaryl, or C(O)R₃, wherein
   i) each of said aryl or heteroaryl may additionally be fused with an independently selected aryl or heteroaryl; and
   ii) each of said aryl, heteroaryl, and alkyl is either unsubstituted or substituted with 1, 2, 3, 4 or 5 substituents which can be the same or different and are independently selected from the group consisting of halo, hydroxyl, cyano, oxo, amino, aminoalkyl-, (amino)alkoxy-, -alkyl, -alkenyl, -alkynyl, alkoxy-, hydroxy, -alkylhydroxy, aryloxy-, -alkyl(aryl), (alkoxyalkyl)amino-, -aryl, -aryl(halo), -heteroaryl, C(O)OC$_n$, —NR$^a$R$^b$; deuterium, hydroxyl-alkyl-, hydroxyl-aryl-, amino, aminoalkyl, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, (alkoxyalkyl)amino-, —O(alkyl), —O(aryl), O(heteroaryl), —NH(SO₂)alkyl, —NH(SO₂)aryl, —NH(SO₂)heteroaryl, -(aryl)alkyl-, —S(O)₂-alkyl, —S(O)₂-aryl, —C(O)alkyl, —NHC(O)-alkyl, NH—, —NH—C(O)— R$^c$—(O)alkyl, —NH—C(O)-aryl, —NH—C(O)—NH-alkyl, NH—C(O)— NH—C(O)—NH-aryl, —NH—C(O)—O-alkyl, —NH(R$^c$)—C(O)-alkyl, —NH(R$^c$)—C(O)-aryl, —S(O₂)NH₂, —S(O₂)NH(alkyl), —S(O₂)N(alkyl)₂, —C(O)N(H)(alkyl), —CH$_z$F$_{3-z}$, —OCH$_z$F$_{3-z}$;

R₂ is hydrogen, hydroxyl, or a group selected from -oxy(alkyl), -oxy(alkene), alkyl, -alkenyl, -oxy(alkyl)-aryl, -oxyalkynyl, OC(O)(alkyl), OC(O)(haloalkyl), and OC(O)(aryl) which is either substituted or non-substituted and straight or branched, where the substituents can be the same or different and are from the group consisting of oxo or halo;

R₃ is an alkyl, alkoxy(alkyl), substituted or unsubstituted monocyclic or bicyclic aryl or heteroaryl, or alkyl(aryl), the substituted or unsubstituted monocyclic or bicyclic heteroaryl having 0, 1, 2 or 3 heteroatoms independently selected from N, O, or S;

R$^a$ is an alkyl, alkoxy(alkyl), substituted or unsubstituted monocyclic or bicyclic aryl or heteroaryl, or alkyl(aryl), the substituted or unsubstituted monocyclic or bicyclic heteroaryl having 0, 1, 2 or 3 heteroatoms independently selected from N, O, or S;

R$^b$ is hydrogen or halo;

R$^c$ is hydrogen, halo, or alkyl;

--- is an optional bond that is present only when R₂ is hydrogen;

n is 0, 1, 2, or 3; and z is 0, 1, or 2.

Another aspect of this invention is the provision of compounds, compositions, and kits for the improved solubility of target compounds, including but not limited to, macrophage migration inhibitory factor (MIF) inhibitors, epidermal growth factor receptor (EGFR) inhibitors, kinase inhibitors, and prodrugs of alpha4 beta1 and alpha4 beta7 integrin antagonists of Formula II:

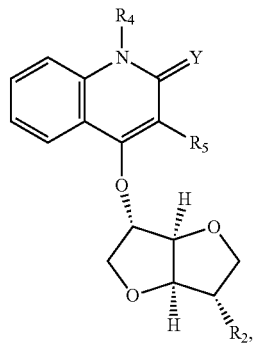

wherein:

R₂ is hydrogen, hydroxyl, or a group substituted or non-substituted and straight or branched selected from -oxy(alkyl), -oxy(alkene), alkyl, -alkenyl, -alkynyl, —OC(O)(alkyl), —OC(O)(haloalkyl), and —OC(O)(aryl);

R₄ is cyano, amino, aminoalkyl-, alkyl, -alkyl(aryl), substituted or non-substituted aryl, if substituted then substituted with 1, 2, 3, 4 or 5 substituents which can be the same or different and are independently selected from the group consisting of halo, hydroxyl, cyano, oxo, amino, aminoalkyl-, alkyl(arylhalide), (amino)alkoxy-, -alkyl, -alkenyl, -alkynyl, alkoxy-, hydroxy, -alkylhydroxy, -alkyl(aryl), aryloxy-, -alkyl(aryl), (alkoxyalkyl)amino-, -aryl, -aryl(halo), -heteroaryl, C(O)OC$_n$, —NR$^a$R$^b$; deuterium, hydroxyl-alkyl-, hydroxyl-aryl-, amino, aminoalkyl;

R₅ is C(O)R$^c$ or cyano;

R$^c$ is hydrogen, or a group, substituted or unsubstituted, selected from straight or branched C₁ to C₃ alkyl, CF₃, alkoxy, aryl, and monocyclic or bicyclic heteroaryl having one to three heteroatoms independently selected from O, S, and N and if substituted then substituted with 1, 2, 3, 4 or 5 substituents which can be the same or different and are independently selected from the group consisting of halo, hydroxyl, cyano, oxo, amino, aminoalkyl-, ethoxy, (amino)alkoxy-, -alkyl, -alkenyl, -alkynyl, alkoxy-, hydroxy, -alkylhydroxy, -alkyl(aryl), aryloxy-, -alkyl(aryl), (alkoxyalkyl)amino-, -aryl, -aryl(halo), -heteroaryl, C(O)OC$_n$, —NR$^a$R$^b$; deuterium, hydroxyl-alkyl-, hydroxyl-aryl-, amino, aminoalkyl; and Y is S or O.

Still another aspect of this invention is the provision of compounds, compositions, and kits for the improved solubility of target compounds, including but not limited to, macrophage migration inhibitory factor (MIF) inhibitors, epidermal growth factor receptor (EGFR) inhibitors, kinase inhibitors, and prodrugs of alpha4 beta1 and alpha4 beta7 integrin antagonists of Formula III:

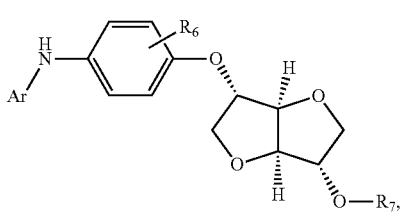

wherein;

$R_6$ is hydrogen, halo, CN, alkyl, alkoxy, aryloxy, aryl, and $SO_2$(alkyl);

$R_7$ is hydrogen, $C(O)R^c$, alkyl, haloalkyl, alkenyl, alkynyl, and —$CH_2$(aryl);

Ar is a substituted or non-substituted monocyclic or bicyclic heteroaryl, with one to four heteroatoms independently selected from O, S, and N, wherein the substituents are selected from the group consisting of halo, hydroxyl, oxy, cyano, amino, aminoalkyl-, (amino)alkoxy-, -alkyl, -alkenyl, -alkynyl, alkoxy-, hydroxy, $NR^aR^b$, $OC_n$, —$CH_zF_{3-z}$, —$OCH_zF_{3-z}$, aryloxy-, (alkoxyalkyl)amino-, —O(alkyl), —O(aryl), —O(heteroaryl), —C(O)NH(alkyl), —$C(O)N(aryl)_2$, —$NH(SO_2)$alkyl, —$NH(SO_2)$aryl, —$NH(SO_2)$heteroaryl, (aryl)alkyl-, -heteroaryl, (heteroaryl)alkyl-, —$S(O)_2$-alkyl, —$S(O)_2$-aryl, —$C(O)N(alkyl)_2$, —C(O)alkyl, —NHC(O)-alkyl, —NH—C(O)— $R^c$—(O)alkyl, —NH—C(O)-aryl, —NH—C(O)—NH-alkyl, NH—C(O)—NH-aryl, —NH—C(O)—O-alkyl, —$NH(R^c)$—C(O)-alkyl, —$NH(R^c)$—C(O)-aryl, —$S(O_2)NH_2$, —$S(O_2)NH$(alkyl), —$S(O_2)N$(alkyl)$_2$, —C(O)N(H)(alkyl), —$CH_zF_{3-z}$, —$OCH_zF_{3-z}$, or -alkyl(aryl); and $R^c$ is hydrogen, or a group, substituted or unsubstituted, selected from straight or branched $C_1$ to $C_3$ alkyl, alkenyl, alkynyl, $CF_3$, alkoxy, aryl, and monocyclic or bicyclic heteroaryl having one to three heteroatoms independently selected from O, S, and N and if substituted then substituted with 1, 2, 3, 4 or 5 substituents which can be the same or different and are independently selected from the group consisting of halo, hydroxyl, cyano, oxo, amino, aminoalkyl-, ethoxy, (amino)alkoxy-, -alkyl, -alkenyl, -alkynyl, alkoxy-, hydroxy, -alkylhydroxy, -alkyl(aryl), aryloxy-, -alkyl (aryl), (alkoxyalkyl)amino-, -aryl, -aryl(halo), -heteroaryl, $C(O)OC_n$, —$NR^aR^b$; deuterium, hydroxylalkyl-, hydroxyl-aryl-, amino, aminoalkyl.

Still another aspect of this invention is the provision of compounds, compositions, and kits for the improved solubility of target compounds, including but not limited to, macrophage migration inhibitory factor (MIF) inhibitors, epidermal growth factor receptor (EGFR) inhibitors, kinase inhibitors, and prodrugs of alpha4 beta1 and alpha4 beta7 integrin antagonists of Formula IV:

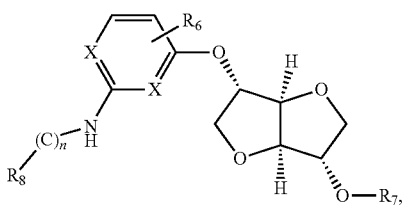

IV wherein;

$R_6$ is hydrogen, halo, CN, alkyl, alkoxy, aryloxy, aryl, and $SO_2$(alkyl);

$R_7$ is hydrogen, $C(O)R^c$, alkyl, alkenyl, alkynyl, and —$CH_2$(aryl);

$R_8$ is substituted or non-substituted aryl or cycloalkyl or heterocycloalkyl, wherein the substituents are selected from the group consisting of straight or branched alkyl, halo, hydroxyl, oxy, cyano, amino, dimethylpropanone, aminoalkyl-, (amino)alkoxy-, -alkyl(arylhalide), -alkyl, -alkenyl, -alkynyl, alkoxy-, hydroxy, -alkylhydroxy, aryloxy-, -alkyl(aryl), —$SO_2$(aryl), —$SO_2$(alkyl), (alkoxyalkyl)amino-, -aryl, -heteroaryl, $C(O)C_n$, $C(O)OC_n$, —$NR^aR^b$, and deuterium;

$R^c$ is substituted or unsubstituted aryl, substituted or unsubstituted alkyl, alkenyl, and alkynyl;

X is independently C, N, S, or O; and n is 0, 1, or 2.

Another aspect of this invention is the provision of pharmaceutical compositions comprising therapeutically effective amounts of at least one compound of Formula I, II, III, or IV.

Another preferred embodiment is a pharmaceutical formulation comprising a pharmaceutically acceptable compound of the present invention, which provides, upon administration to a human, a decrease in tumor burden and/or metastases. The pharmaceutical formulation can be administered by oral means or other suitable means.

Another preferred embodiment is a pharmaceutical formulation comprising a pharmaceutically acceptable compound of the present invention for treatment of a variety of cancers including but not limited to cervix, colon, breast, lung, non-small cell lung cancer, glioma and stomach cancers.

Another preferred embodiment is a pharmaceutical formulation comprising a pharmaceutically acceptable compound of the present invention for treatment hematologic cancer, such as but not limited to leukemia, lymphoma and multiple myeloma.

Another preferred embodiment is a pharmaceutical formulation comprising a pharmaceutically acceptable compound of the present invention for treatment of midline carcinomas, mesenchymal, hepatic, renal and neurological tumors.

Another preferred embodiment is a pharmaceutical formulation comprising a pharmaceutically acceptable compound of the present invention for treatment of melanoma, squamous cell carcinoma and cutaneous T-cell lymphoma.

Another preferred embodiment is a pharmaceutical formulation comprising a pharmaceutically acceptable compound of the present invention for treatment of a variety of diseases or conditions related to systemic or tissue inflammation, inflammatory responses to infection or hypoxia, cellular activation and proliferation, lipid metabolism, fibrosis and in the prevention and treatment of viral infections.

Another preferred embodiment is a pharmaceutical formulation comprising a pharmaceutically acceptable compound of the present invention for treatment of a variety of chronic and inflammatory conditions, including but not limited to rheumatoid arthritis, osteoarthritis, acute gout, psoriasis, systemic lupus erythematosus, multiple sclerosis, Crohn's disease, ulcerative colitis, asthma, chronic obstructive airways disease, pneumonitis, myocarditis, pericarditis, myositis, eczema, dermatitis, alopecia, vitiligo, bullous skin disease, nephritis, vasculitis, atherosclerosis, Alzheimer's disease, depression, Sjogren's syndrome, siloadenitis, central retinal vein occlusion, branched retinal vein occlusion, Irvine-Gass syndrome, parafoveal telangiectasis, retinitis pigmentosa, pars planitis, birdshot retinochoroidopathy, epiretinal membrane, cystic macular edema, maculopathies, vitreomacular traction syndromes, retinal detachment, neuroretinitis, idiopathic macular edema, retinitis, dry eye, vernal keratoconjuctivitis, atopic keratoconjuctivitis, anterior uveitis, pan uveitis, posterior uveitis, uveitis-associated macular edema, scleritis, diabetic retinopathy, diabetic macular edema, age-related macular dystrophy, hepatitis, pancreatitis, primary biliary cirrhosis, sclerosing cholangitis, Addison's disease, hypophysitis, thyroiditis, type I diabetes and acute rejection of transplanted organisms.

Another preferred embodiment is a pharmaceutical formulation comprising a pharmaceutically acceptable compound of the present invention for treatment of a variety of acute inflammatory conditions such as acute gout, giant cell arteritis, nephritis including lupus nephritis, vasculitis with organ involvement such as glomerulonephritis, vasculitis including giant cell arteritis, Wegner's granulomatosis, Polyarteritis nodosa, Becet's disease, Kawasaki disease, Takayasu's arteritis, pyoderma gangrenosum, vasculitis with organ involvement and acute rejection of transplanted organs.

Another preferred embodiment is a pharmaceutical formulation comprising a pharmaceutically acceptable compound of the present invention for treatment of a variety of diseases or conditions which involve inflammatory responses to infections with bacteria, viruses, fungi, parasites or their toxins, such as but not limited to sepsis, sepsis syndrome, septic shock, endotoxaemia, systemic inflammatory response syndrome, multi organ dysfunction syndrome, toxic shock syndrome, acute lung injury, acute respiratory distress syndrome, acute renal failure, fulmiant hepatitis, burns, acute pancreatitis, post-surgical syndromes, sarcoidosis, Herxheimer reactions, encephalitis, myelitis, meningitis, malaria, systemic inflammatory responses associated with viral infections, such as but not limited to influenza, herpes zoster, herpes simplex and coronavirus.

Another preferred embodiment is a pharmaceutical formulation comprising pharmaceutically acceptable compound of the present invention for treatment of a variety of conditions associated with ischaemia reperfusion injury such as myocardial infarction, cerebrovascular ischaemia, acute coronary syndromes, renal reperfusion injury, organ transplantation, coronary artery bypass procedures, cardio-, pulmonary and bypass procedures, pulmonary, renal, hepatitic, gastrointestinal or peripheral limb embolism.

Another preferred embodiment is a pharmaceutical formulation comprising a pharmaceutically acceptable compound of the present invention for treatment of a variety of disorders of lipid metabolisms such as hypercholesterolemia, atherosclerosis and Alzheimer disease.

Another preferred embodiment is a pharmaceutical formulation comprising a pharmaceutically acceptable compound of the present invention for treatment of a variety of fibrotic conditions such as, but not limited to idiopathic pulmonary fibrosis, renal fibrosis, post-operative structure, keloid scar formation, scleroma and cardial fibrosis.

Another preferred embodiment is a pharmaceutical formulation comprising a pharmaceutically acceptable compound of the present invention for treatment of a variety of viral infections such as, but not limited to herpes virus, human papilloma virus, adenovirus, poxvirus, and DNA-viruses in general.

Another preferred embodiment is a pharmaceutical formulation comprising a pharmaceutically acceptable compound of the present invention for treatment of a variety of conditions such as non-malignant melanoma, actinic keratosis, basal cell melanoma, in situ melanoma, squamous cell carcinoma and cutaneous T-cell lymphoma.

Another preferred embodiment is a pharmaceutical formulation comprising a pharmaceutically acceptable compound of the present invention for treatment of obesity.

Another preferred embodiment is a pharmaceutical formulation comprising a pharmaceutically acceptable compound of the present invention for male contraceptive.

Yet another embodiment is a method of treating a disease associated with systemic inflammatory response syndrome, such as but not limited to sepsis, burns, pancreatitis, major trauma, hemorrhage and ischaemia.

Another preferred embodiment is a method to reduce incidence of SIRS, onset of shock, multi-organ dysfunction syndrome, acute lung injury, acute renal hepatic, cardiac and gastrointestinal injury at the point of diagnosis by administering compounds of this disclosure.

Another preferred embodiment is a method to reduce incidence of sepsis, hemorrhage, tissue damage, and multiple organ dysfunction before surgery or any procedure with high risk of sepsis.

Pharmaceutical compositions of this invention may be administered by any appropriate way: orally, including buccal or sublingual, rectal, inhaled, intranasal, topical, ocular, vaginal or parenteral, including subcutaneous, intramuscular, intravenous and intradermal route.

Yet another embodiment is a method of preparing a pharmaceutical formulation of the present invention by mixing at least one pharmaceutically acceptable compound of the present invention, and, optionally, one or more pharmaceutically acceptable additives or excipients.

According to one embodiment of this invention is a method of preparing a pharmaceutical formulation of the present invention by mixing at least one pharmaceutically acceptable compound of the present invention and one or more additional therapeutic agents.

According to one embodiment of the invention the additional therapeutic agents may be selected from the group consisting of cytotoxic agent, cisplatin, doxorubicin, taxotere, taxol, etoposide, irinotecan, camptostar, topotecan, paclitaxel, docetaxel, the epothilones, tamoxifen, 5-fluorouracil, methotrexate, temozolomide, cyclophosphamide, SCH 66336, tipifarnib (Zarnestra®), R115777, L778,123, BMS 214662, Iressa®, Tarceva®, $C_{225}$, GLEEVEC®, Intron®, Peg-Intron®, aromatase combinations, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, leucovirin, oxaliplatin (ELOXATIN®), Pentostatine, Vinblastine, Vincristine, Vindesine, Bleomycin, Dactinomycin, Daunorubicin, Epirubicin, Idarubicin, Mithramycin™, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Rituximab, C225, Campath, leucovorin, dexamethasone, bicalutamide, carboplatin, letrozole, megestrol, and valrubicin.

For preparing pharmaceutical compositions from the compounds described in this disclosure inert, pharmaceutically acceptable carriers can be either solid or liquid. Solid form preparations include powders, tablets, dispersible granules, capsules, cachets and suppositories. The powders and tablets may be comprised of from about 5 percent to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

If formulated as a fixed dose, such combination products employ the compounds of this invention within the dosage range described herein, or as known to those skilled in the art.

Since the compounds of this invention are intended for use in pharmaceutical compositions a skilled artisan will understand that they are each preferably provided in substantially pure forms for example, at least 60% pure, more suitably at least 75% pure, preferably at least 85% pure and most preferably at least 98% pure (w/w).

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Definitions

As used above, and throughout this disclosure, the following terms, unless otherwise indicated, shall be understood to have the following meanings. If a definition is missing, convention definition as known to one skilled in the art controls.

As used herein, the terms "including," "containing," and "comprising" are used in their open, non-limiting sense.

As used herein, the singular forms "a," "an," and "the" include plural referents unless the context clearly dictates otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently The terms "effective amount" or "therapeutically effective amount" refer to a sufficient amount of the agent to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective amount" in any individual case may be determined by one of ordinary skill in the art using routine experimentation. Thus, the expression "effective amount" generally refers to the quantity for which the active substance has therapeutic effects.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping or alleviating the symptoms of the disease or disorder.

By using the terms "pharmaceutically acceptable" or "pharmacologically acceptable" it is intended to mean a material which is not biologically or otherwise undesirable—the material may be administered to an individual without causing any substantially undesirable biological effects or interacting in a deleterious manner with any of the components of the composition in which it is contained.

"Carrier materials" or what are also referred to as "excipients" include any commonly used excipients in pharmaceutics and should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

"Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate carrageenan, monoglyceride, diglyceride, pregelatinized starch, and the like. See, e.g., Hoover, John E., *Remington's Pharmaceutical Sciences*, Mack Publishing Co., Easton, Pa. 1975.

The present invention also includes "prodrugs" of compounds of the invention. The term "prodrug" includes any covalently bonded carriers that release an active parent drug of the present invention in vivo when such prodrug is administered to an animal. Release of the active ingredient occurs in vivo. Prodrugs can be prepared by techniques known to one skilled in the art. These techniques generally modify appropriate functional groups in a given compound. These modified functional groups, however, regenerate original functional groups by routine manipulation or in vivo. Prodrugs of compounds of the present invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of the invention, amides (e.g., trifluoroacetylamino, acetylamino, and the like), and the like. Since prodrugs are known to enhance numerous desirable qualities of pharmaceuticals (e.g., solubility, bioavailability, manufacturing, transport, pharmacodynamics, etc.), the compounds of the present invention may be delivered in prodrug form. Prodrugs, for instance, may be bioavailable by oral administration even when the parent drug is not. Thus, the present invention is intended to cover prodrugs of the presently claimed compounds, methods of delivering the same, and compositions containing the same. Generally speaking, prodrugs are derivatives of per se drugs that after administration undergo conversion or metabolism to the physiologically active species. The conversion may be spontaneous, such as hydrolysis in the physiological environment, or may be enzyme-catalyzed. Prodrugs include compounds that can be oxidized, reduced, aminated, deaminated, hydroxylated, dehydroxylated, hydrolyzed, esterified, alkylated, dealkylated, acylated, deacylated, phosphorylated, and/or dephosphorylated to produce the active compound.

The terms "administered", "administration", or "administering" a compound will be understood to mean providing any compound of the invention to an individual, including an animal, in need of treatment by bringing such individual in contact with, or otherwise exposing such individual to, such compound.

As used herein, "alkyl" means a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, branched or cyclized. As used herein, "lower alkyl" means an alkyl having from 1 to 6 carbon atoms.

As used herein, an "alkenyl" includes an unbranched or branched hydrocarbon chain having one or more double bonds therein. The double bond of an alkenyl group can be unconjugated or conjugated to another unsaturated group. Illustrative alkenyl groups include, but are not limited to, ($C_2$-$C_8$) alkenyl groups, such as ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted.

As used herein, "alkynyl" includes an unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$) alkynyl groups, such as ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The terms "trifluoromethyl", "sulfonyl", and "carboxyl" include $CF_3$, $SO_2$, and $CO_2H$, respectively.

The term "hydroxyl" means an OH group;

The term "alkyl hydroxyl" or "hydroxyalkyl" means an alkyl group as defined above, where the alkyl group has an OH group disposed thereon.

The term "alkoxy" as used herein includes—O-(alkyl), wherein alkyl is defined above.

The term "aminoalkyl" as used herein means a group having one or more nitrogen atoms and one or more alkyl groups as defined above on the nitrogen.

"Aralkyl" or "arylalkyl" means an aryl-alkyl-group in which the aryl (discussed later) and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

It should also be noted that any carbon as well as heteroatom with unsatisfied valences in the text, schemes, examples and Tables herein is assumed to have the sufficient number of hydrogen atom(s) to satisfy the valences.

When any variable (e.g., aryl, heterocycle, $R^2$, etc.) occurs more than one time in any constituent or in the Formulas, its definition on each occurrence is independent of its definition at every other occurrence.

As used herein, the term "composition" is intended to encompass a product comprising the specified ingredients in the specified amounts, as well as any product which results, directly or indirectly, from the combination of the specified ingredients in the specified amounts.

The term "halo" as used herein means a substituent having at least one halogen selected from fluorine, chlorine, bromine, and iodine.

The term "cyano" as used herein means a substituent having a carbon atom joined to a nitrogen atom by a triple bond.

The term "amino" as used herein means a substituent containing at least one nitrogen atom. Specifically, amide-, carbamide-, urea, and sulfamide substituents are included in the term "amino".

The term "(amino)alkoxy" as used herein means a substituent having at least one amino group and at least one alkoxy group.

The term "aryloxy" as used herein means a substituent of the form Ar—O— where Ar is an aryl group as defined herein.

As used herein, the term "aryl" refers to a monocyclic, or fused polycyclic, aromatic carbocycle (ring structure having ring atoms that are all carbon) having from 3 to 24 ring atoms per ring.

As used herein, the term "heteroaryl" refers to a monocyclic, or fused polycyclic, aromatic heterocycle (ring structure having ring atoms selected from carbon atoms as well as nitrogen, oxygen, and sulfur heteroatoms) having from 3 to 24 ring atoms per ring.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

As used herein, the term "optionally substituted" means that the specified group is unsubstituted or substituted by one or more substituents.

When used as a therapeutic agent, the MIF, EGRF, and kinase inhibitors described herein may be administered with one or more physiologically acceptable excipients. A physiologically acceptable carrier or excipient is a formulation to which the compound can be added to dissolve it or otherwise facilitate its administration.

The dosage forms of the present invention, may contain a mixture of one or more compounds of this invention, and may include additional materials known to those skilled in the art as pharmaceutical excipients. Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octaacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, ascorbyl palmitate, butylated hydroxyanisole, butylated hydroxytoluene, hypophosphorous acid, monothioglycerol, propyl gallate sodium formaldehyde sulfoxylate sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate ethylcellulose, gelatin, pharmaceutical glaze, hydroxypropyl cellulose, hydroxypropyl methylcellulose, hydroxypropyl methylcellulose phthalate methacrylic acid copolymer, methylcellulose, polyethylene glycol, polyvinyl acetate phthalate shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate glycerin, mono- and di-acetylated monoglycerides, polyethylene glycol, propylene glycol, triacetin, triethyl citrate); Polymers (e.g., cellulose acetate, alkyl celluloses, hydroxyalkylcelluloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol) may be used as excipients. This list is not meant to be exclusive, but instead merely representative of the classes of excipients and the particular excipients which may be used in dosage forms of the present invention.

The compounds of Formulas I to IV can also form salts which are also within the scope of this invention. Reference to a compound of the Formula herein is understood to include reference to salts thereof, unless otherwise indicated.

The term "salt(s)", as employed herein, denotes acidic salts formed with inorganic and/or organic acids, as well as basic salts formed with inorganic and/or organic bases. In addition, when a compound of the Formula contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula may be formed, for example, by reacting a compound of Formula with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of the various Formulas, and salts, solvates, esters and prodrugs thereof, may exist in their tautomeric form (for example, as an amide or imino ether). All such tautomeric forms are contemplated herein as part of the present invention.

The compounds of the various Formulas may contain asymmetric or chiral centers, and, therefore, exist in different stereoisomeric forms. It is intended that all stereoisomeric forms of the compounds of the various Formulas as well as mixtures thereof, including racemic mixtures, form part of the present invention. In addition, the present invention embraces all geometric and positional isomers. For example, if a compound of the various Formulas incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the various Formulas may be atropisomers (e.g., substituted biaryls) and are considered as part of this invention. Enantiomers can also be separated by use of a chiral HPLC column.

It is also possible that the compounds of the various Formulas may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the various Formulas incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The foregoing merely summarizes the various aspects and preferred embodiments thereof, of the invention and is not intended to be limiting in nature. These aspects and embodiments are described more fully below.

DESCRIPTION OF THE PREFERRED EMBODIMENTS

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Compounds of the Invention

The present invention relates to particular molecules and pharmaceutically acceptable salts or isomers thereof. The invention further relates to molecules which are useful in macrophage migration inhibitory factor (MIF) inhibitors, epidermal growth factor receptor (EGRF) inhibitors, kinase inhibitors, and prodrugs of alpha4 beta1 and alpha4 beta7 integrin antagonists and pharmaceutically acceptable salts or isomers thereof.

The invention is directed to compounds as described herein and pharmaceutically acceptable salts or isomers thereof, and pharmaceutical compositions comprising one or more compounds as described herein and pharmaceutically acceptable salts or isomers thereof. One aspect of this invention is the provision of compounds, compositions, and kits for macrophage migration inhibitory factor (MIF) inhibitors, epidermal growth factor receptor (EGFR) inhibitors, kinase inhibitors, and prodrugs of alpha4 beta1 and alpha4 beta7 integrin antagonists comprising a compound of Formula I:

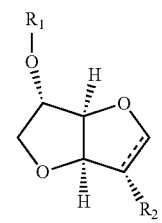

wherein:
R$_1$ is -aryl, -heteroaryl, or C(O)R$_3$, wherein
  i) each of said aryl or heteroaryl may additionally be fused with an independently selected aryl or heteroaryl; and
  ii) each of said aryl, heteroaryl, and alkyl is either unsubstituted or substituted with 1, 2, 3, 4 or 5 substituents which can be the same or different and are independently selected from the group consisting of halo, hydroxyl, cyano, oxo, amino, aminoalkyl-, (amino)alkoxy-, -alkyl, -alkenyl, -alkynyl, alkoxy-, hydroxy, -alkylhydroxy, aryloxy-, -alkyl(aryl), (alkoxyalkyl)amino-, -aryl, -aryl(halo), -heteroaryl, C(O)OC$_n$, —NR$^a$R$^b$; deuterium, hydroxyl-alkyl-, hydroxyl-aryl-, amino, aminoalkyl, —CONH$_2$, —C(O)NH(alkyl), —C(O)N(alkyl)$_2$, —C(O)NH (aryl), —C(O)N(aryl)$_2$, —CH$_z$F$_{3-z}$, —OCH$_z$F$_{3-z}$, (alkoxyalkyl)amino-, —O(alkyl), —O(aryl), O(heteroaryl), NH(SO$_2$)alkyl, —NH(SO$_2$)aryl, —NH (SO$_2$)heteroaryl, (aryl)alkyl-, —S(O)$_2$-alkyl, —S(O)$_2$-aryl, —C(O)alkyl, —NHC(O)-alkyl, NH—, —NH—C(O)— R$^c$—(O)alkyl, —NH—C (O)-aryl, —NH—C(O)—NH-alkyl, NH—C(O)—NH—C(O)—NH-aryl, —NH—C(O)—O-alkyl, —NH(R$^c$)—C(O)-alkyl, —NH(R$^c$)—C(O)-aryl, —S(O$_2$)NH$_2$, —S(O$_2$)NH(alkyl), —S(O$_2$)N(alkyl)$_2$, —C(O)N(H)(alkyl), —CH$_z$F$_3$-z, —OCH$_z$F$_{3-z}$;
R$_2$ is hydrogen, hydroxyl, OC(O)CH$_3$, -oxy(aryl), or a group selected from -oxy(alkyl), -oxy(alkene), alkyl, -alkenyl, -oxy(alkyl)-aryl, -oxyalkynyl, —OC(O) (alkyl), —OC(O)(haloalkyl), and —OC(O)(aryl) which is either substituted or non-substituted and straight or branched, where the substituents can be the same or different and are from the group consisting of oxo or halo;
R$_3$ is an alkyl, alkyl(benzyl), alkoxy(alkyl) all of which may be substituted or unsubstituted, substituted or unsubstituted monocyclic or bicyclic aryl or heteroaryl, or alkyl(aryl), the substituted or unsubstituted monocyclic or bicyclic heteroaryl having 0, 1, 2 or 3 heteroatoms independently selected from N, O, or S;

$R^a$ is an alkyl, alkyl(benzyl), alkoxy(alkyl) all of which may be substituted or unsubstituted, substituted or unsubstituted monocyclic or bicyclic aryl or heteroaryl, or alkyl(aryl), the substituted or unsubstituted monocyclic or bicyclic heteroaryl having 0, 1, 2 or 3 heteroatoms independently selected from N, O, or S;

$R^b$ is hydrogen or halo;

$R^c$ is hydrogen, halo, or alkyl;

--- is an optional bond that is present only when $R_2$ is hydrogen;

n is 0, 1, 2, or 3; and z is 0, 1, or 2.

In another embodiment $R_2$ of Formula I is hydrogen.

In another embodiment $R_1$ of Formula I is a substituted bicyclic ring having 0, 1, 2, or 3 heteroatoms independently selected from N, O, or S; and $R_2$ is hydroxyl or $OC(O)C_nR^b$.

In another embodiment, the compound of Formula I is represented by the compound of Formula II:

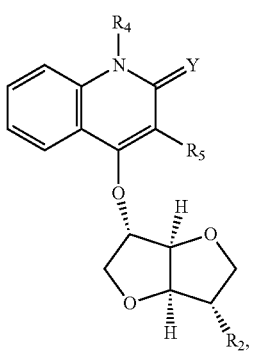

II wherein:

$R_2$ is hydroxyl, or a group substituted or non-substituted and straight or branched selected from -oxy(alkyl), -oxy(alkene), alkyl, -alkenyl, -oxyalkynyl, —OC(O)(alkyl), —OC(O)(haloalkyl), and OC(O)(aryl);

$R_4$ is cyano, amino, aminoalkyl-, alkyl, -alkyl(aryl), substituted or non-substituted aryl, if substituted then substituted with 1, 2, 3, 4 or 5 substituents which can be the same or different and are independently selected from the group consisting of halo, hydroxyl, cyano, oxo, amino, aminoalkyl-, alkyl(arylhalide), (amino)alkoxy-, -alkyl, -alkenyl, -alkynyl, alkoxy-, hydroxy, -alkylhydroxy, -alkyl(aryl), aryloxy-, -alkyl(aryl), (alkoxyalkyl)amino-, -aryl, -aryl(halo), -heteroaryl, $C(O)OC_n$, —$NR^aR^b$; deuterium, hydroxyl-alkyl-, hydroxyl-aryl-, amino, aminoalkyl;

$R_5$ is $C(O)R^c$ or cyano;

$R^c$ is hydrogen, or a group, substituted or unsubstituted, selected from straight or branched $C_1$ to $C_3$ alkyl, $CF_3$, alkoxy, aryl, and monocyclic or bicyclic heteroaryl having one to three heteroatoms independently selected from O, S, and N and if substituted then substituted with 1, 2, 3, 4 or 5 substituents which can be the same or different and are independently selected from the group consisting of halo, hydroxyl, cyano, oxo, amino, aminoalkyl-, ethoxy, (amino)alkoxy-, -alkyl, -alkenyl, -alkynyl, alkoxy-, hydroxy, -alkylhydroxy, -alkyl(aryl), aryloxy-, (alkoxyalkyl)amino-, -aryl, -aryl(halo), -heteroaryl, $C(O)OC_n$, —$NR^aR^b$; deuterium, hydroxyl-alkyl-, hydroxyl-aryl-, amino, aminoalkyl; and Y is S or O.

In another embodiment of Formula II, $R_4$ is selected from the group consisting of:

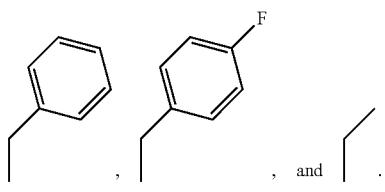

In another embodiment of Formula II, $R_4$ is alkyl(aryl), Y is oxy, $R_5$ is $C(O)OC_n$, and where n is 0, 1, 2, or 3.

In another embodiment, the compound of Formula I is represented by the compound of Formula III:

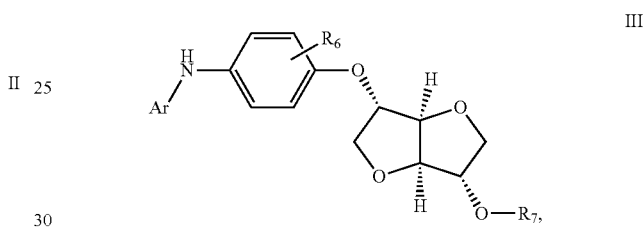

III wherein;

$R_6$ is hydrogen, halo, CN, alkyl, alkoxy, aryloxy, aryl, and $SO_2$(alkyl);

$R_7$ is hydrogen, $C(O)R^c$, alkyl, haloalkyl, alkenyl, alkynyl, and —$CH_2$(aryl);

Ar is a substituted or non-substituted monocyclic or bicyclic heteroaryl, with one to four heteroatoms independently selected from O, S, and N, wherein the substituents are selected from the group consisting of halo, hydroxyl, oxy, cyano, amino, aminoalkyl-, (amino)alkoxy-, -alkyl, -alkenyl, -alkynyl, alkoxy-, hydroxy, $NR^aR^b$, $OC_n$, —$CH_zF_{3-z}$, —$OCH_zF_{3-z}$, aryloxy-, (alkoxyalkyl)amino-, —O(alkyl), —O(aryl), —O(heteroaryl), —C(O)NH(alkyl), —C(O)N(aryl)$_2$, —NH($SO_2$)alkyl, —NH($SO_2$)aryl, —NH($SO_2$)heteroaryl, (aryl)alkyl-, -heteroaryl, (heteroaryl)alkyl-, —S(O)$_2$-alkyl, —S(O)$_2$-aryl, —C(O)N(alkyl)$_2$, —C(O)alkyl, —NHC(O)-alkyl, —NH—C(O)— $R^c$—(O)alkyl, —NH—C(O)-aryl, —NH—C(O)—NH-alkyl, NH—C(O)—NH-aryl, —NH—C(O)—O-alkyl, —NH($R^c$)—C(O)-alkyl, —NH($R^c$)—C(O)-aryl, —S($O_2$)NH$_2$, —S($O_2$)NH(alkyl), —S($O_2$)N(alkyl)$_2$, —C(O)N(H)(alkyl), —$CH_zF_{3-z}$, —$OCH_zF_{3-z}$, or -alkyl(aryl); and $R^c$ is a group, substituted or unsubstituted, selected from straight or branched $C_1$ to $C_3$ alkyl, alkenyl, alkynyl, $CF_3$, alkoxy, aryl, and monocyclic or bicyclic heteroaryl having one to three heteroatoms independently selected from O, S, and N and if substituted then substituted with 1, 2, 3, 4 or 5 substituents which can be the same or different and are independently selected from the group consisting of halo, hydroxyl, cyano, oxo, amino, aminoalkyl-, ethoxy, (amino)alkoxy-, -alkyl, -alkenyl, -alkynyl, alkoxy-, hydroxy, -alkylhydroxy, -alkyl(aryl), aryloxy-, -alkyl(aryl), (alkoxyalkyl)amino-, -aryl, -aryl(halo), -heteroaryl, C(O)OC$_n$, —NR$^a$R$^b$; deuterium, hydroxyl-alkyl-, hydroxyl-aryl-, amino, aminoalkyl.

In another embodiment Ar of Formula III is selected from the group consisting of:

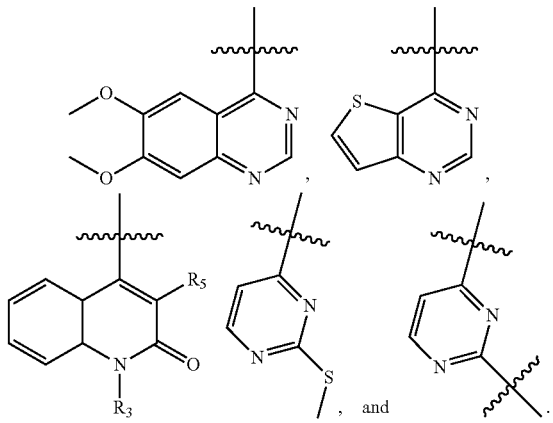

In another embodiment, the compound of Formula I is represented by the compound of Formula IV:

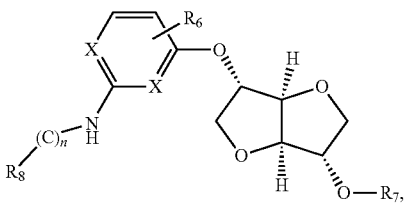

IV wherein;

R$_6$ is hydrogen, halo, alkyl, alkoxy, aryloxy, aryl, and —SO$_2$(alkyl);

R$_7$ is hydrogen, C(O)R$^c$, alkyl, alkenyl, alkynyl, and —CH$_2$(aryl);

R$_8$ is substituted or non-substituted aryl or cycloalkyl or heterocycloalkyl, wherein the substituents are selected from the group consisting of straight or branched alkyl, halo, hydroxyl, oxy, cyano, amino, dimethylpropanone, aminoalkyl-, (amino)alkoxy-, -alkyl(arylhalide), -alkyl, -alkenyl, -alkynyl, alkoxy-, hydroxy, -alkylhydroxy, aryloxy-, -alkyl(aryl), —SO$_2$(aryl), —SO$_2$(alkyl), (alkoxyalkyl)amino-, -aryl, -heteroaryl, C(O)C$_n$, C(O)OC$_n$, —NR$^a$R$^b$, and deuterium;

R$^c$ is hydrogen, halo, aryl, or alkyl;

X is independently C, N, S, or O; and n is 0, 1, or 2.

In another embodiment R$_7$ of Formula IV is C(O)OC.

EXAMPLES

The following are illustrative, but non-limiting, examples of certain embodiments of the present invention. The synthetic schemes are presented for the synthesis of certain compounds herein disclosed. The process and results for the assays testing the effects on the target compound solubility are also described.

Definitions used in the following Schemes and elsewhere herein are:

4-F-PH 4-fluorophenyl
calcd calculated
DIAD diisopropyl azodicarboxylate
DIPEA N,N-diisopropylethylamine
DMF N,N-dimethylformamide
EA ethyl acetate
EtI iodo ethane
EtOH ethanol
HCl hydrochloric acid
HPLC high pressure liquid chromatography
h hours
iso-PrOH isopropanol
LC/MS liquid chromatography/mass spectrometry
MeOH methanol
mcpba m-chloroperbenzoic acid
MS mass spectrometry
NEt$_3$ neat triethylamine
NMP n-methyl-2-pyrrolidone
obsd observed
Ph phenyl
Ph$_3$P triphenylphosphine
rt room temperature
TEA triethylamine
TFA trifluoroacetic acid
THF tetrahydrofuran
TLC thin layer chromotography Materials Unless otherwise noted, the starting materials and reagents used in preparing these compounds were obtained from commercial suppliers, such as Aldrich Chemical Co., Oakwood Chemical Inc., Alfa Aesar, A Johnson Matthey Company, and Matrix Scientific. In some instances, the compounds prepared by methods known to those skilled in the art of following procedures set forth in references such as Fieser and Fieser's Reagents for Organic Synthesis: Wiley & Sons: New York, 1991, Volumes 1-15; and Organic Reactions, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art of having referred to the disclosure contained in this application. The invention described in this application can be applied to many target compounds. Here, we describe a few of those applications.

The starting materials and intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Intermediates and final compounds were purified by either flash chromatography and/or by reverse-phase preparative HPLC. Unless otherwise noted, flash chromatography was performed using the ISCO CombiFlash chromatography instrument (from Teledyne Isco, Inc). Unless otherwise noted, the silica gel brand and pore size utilized were pre-packed 230-400 mesh columns provided by Teledyne, Inc.

Mass spectrometry was performed using a Watres ZQ 4000 (from Watres Corporation), a Waters Quattro micro API. Mass spectra data generally only indicate the parent ions unless otherwise stated. MA data is provided for a particular intermediate or compound where indicated.

Nuclear magnetic resonance spectroscopy (NMR) was performed using a Varian Mercury 300 MHz NMR spectrometer or a Bruker 500 MHz NMR spectrometer. $^1$H NMR data is provided for a particular intermediate or compound where indicated.

Unless specified to the contrary, the reactions described herein preferably are conducted under an inert atmosphere at atmospheric pressure at a reaction temperature range of from about −10° C. to about 180° C., more preferably from about 0° C. to 110° C., and most preferably and conveniently at about room (or ambient) temperature, e.g., about 20° C. Reagents were used as received from commercial suppliers unless otherwise noted. THF was distilled over sodium and benzophenone before use.

endo-mono-benzyl ether isosorbide did not react under these conditions even after extended hours of reaction time.

The esterification reaction of compound I to provide compound II may be carried out in the presence of an alkyl or aryl acid chloride such as VII in the presence of a base such as DIPEA or TEA in an inert solvent such as methylene chloride in an inert atmosphere. The reactions can be performed at temperatures between 0° C. and room temperature for several hours.

Compounds of the invention of general formula III may be prepared from isosorbide and phenol derivative of type VI under similar conditions using 3-6 equivalents of triphenylphosphine, DIAD and DIPEA in an inert solvent such as THF at room temperature for an extended period of reaction

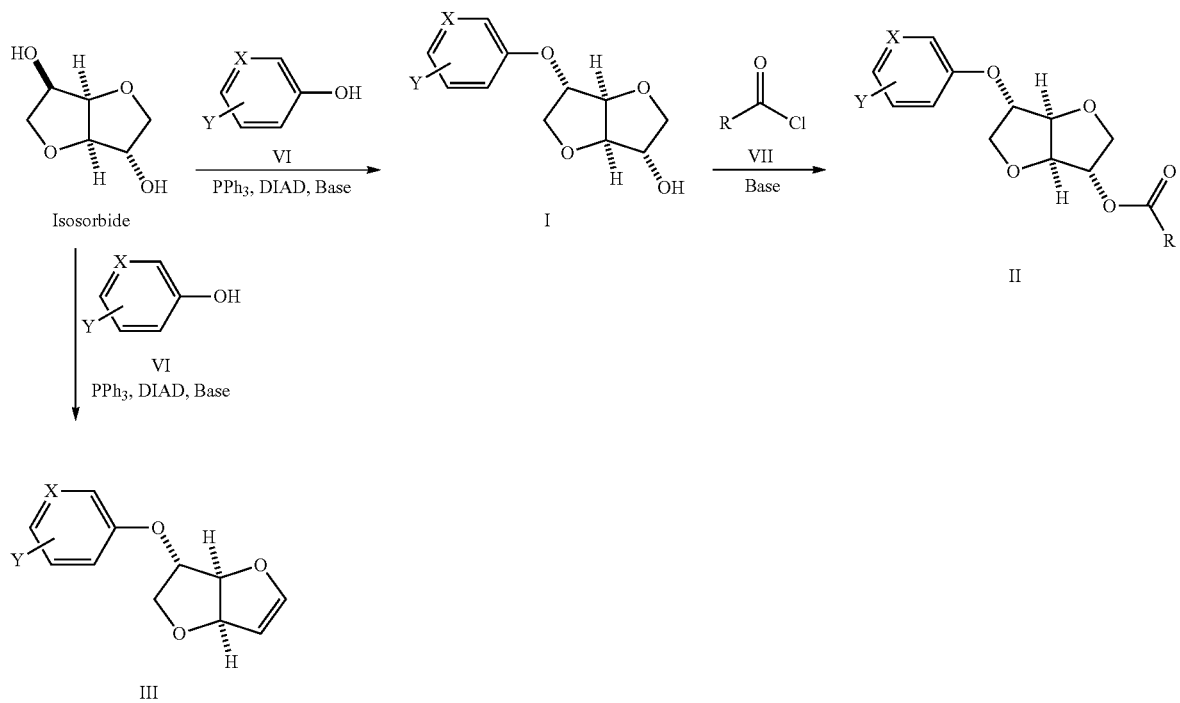

The compounds in the invention of formula I, II, III (above) can be prepared according to Scheme 1. Isosorbide was reacted with a phenol derivative of type VI in the presence of 1.5-3.0 equivalents of triphenylphosphine and diisopropyl azodicarboxylate (DIAD) in the presence of a base such as N,N-diisopropylethylamine (DIPEA) or triethylamine (TEA) in an inert solvent such as tetrahydrofuran (THF) in an inert atmosphere. The reactions can be performed at temperatures between 0° C. and room temperature or 0° C. to 65° ° C. for several hours. As reported (Synthesis, 1981, 1), under these conditions the inversion of stereochemistry occurred at endo hydroxyl position to provide the (3S,3aR,6S,6aR)-2,3,3a,5,6,6a-hexahydrofuro[3,2-b]furan-3,6-diol derivatives (isoidide type, exo, exo) of the compound of general formula I which are rarely available.

The stereochemistry of the product was confirmed by preparation of endo-mono-benzyl ether and exo-mono-benzyl ether isosorbide derivatives following the literature procedure (Carbohydrate Research, 1994, 261, 255-266), it was then found that the exo-mono-benzyl ether isosorbide reacted under these conditions. On the other hand, the time, 6-7 days. This observation is in contrary to the literature report (Synlett, 2003, 11, 1683-1687) where the endo-TBS protected isosorbide reacted with 3-cyanophenol in the presence of DEAD, triphenylphosphine in THF to provide the ether derivative. The current conditions may be different than regular Mitsunobu conditions. The double bond in the compound of the invention of formula III can be a very useful intermediate for further transformations that should be explored in the future.

Scheme 2

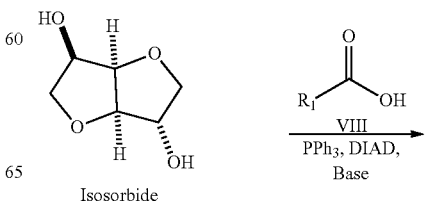

-continued

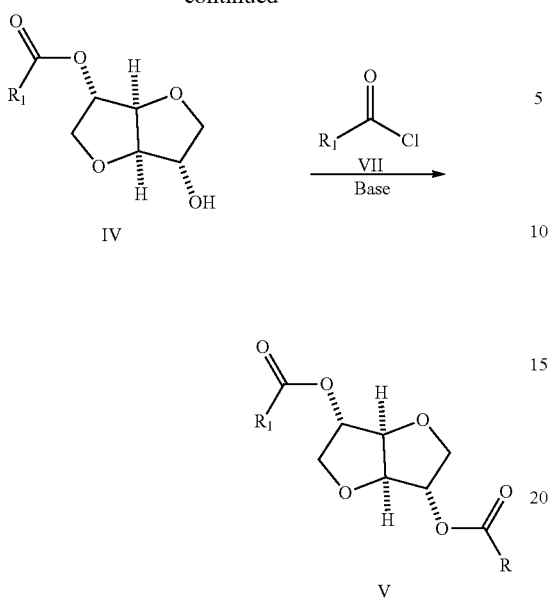

Compounds of the invention of general formula IV and V (above) can be prepared according to Scheme 2. In some instances the isoidide portion can act as a prodrug and the active acid can be released in the in vivo studies. In some cases the isoidide portion behaves as a part of the molecule. Isosorbide was treated with an alkyl, substituted alkyl, aromatic, substituted aromatic, heteroaromatic or substituted heteroaromatic carboxylic acid derivative of type VIII in the presence of 1.5 equivalents of triphenylphosphine and diisopropyl azodicarboxylate in the presence of a base such as DIPEA or TEA in a convenient solvent such as THF in an inert atmosphere. The reactions may be performed at temperatures between 0° C. and room temperature for several hours. Again, under these conditions, the inversion of stereochemistry occurred at the endo hydroxyl position to provide the 3-mono substituted ester derivatives of type (3S,3aR,6S,6aR)-2,3,3a,5,6,6a-hexahydrofuro[3,2-b]furan-3,6-diol (isoidide type, 3-exo and 6-exo) of compound IV.

The esterification reaction of compound IV to provide compound V may be carried out in the presence of an alkyl, substituted alkyl, aromatic or substituted aromatic acid chloride in the presence of a base such as DIPEA or TEA in an inert solvent such as methylene chloride in an inert atmosphere. The reactions may be performed at temperatures between 0° C. and room temperature for several hours.

Scheme 3

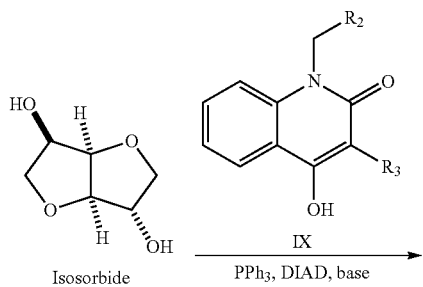

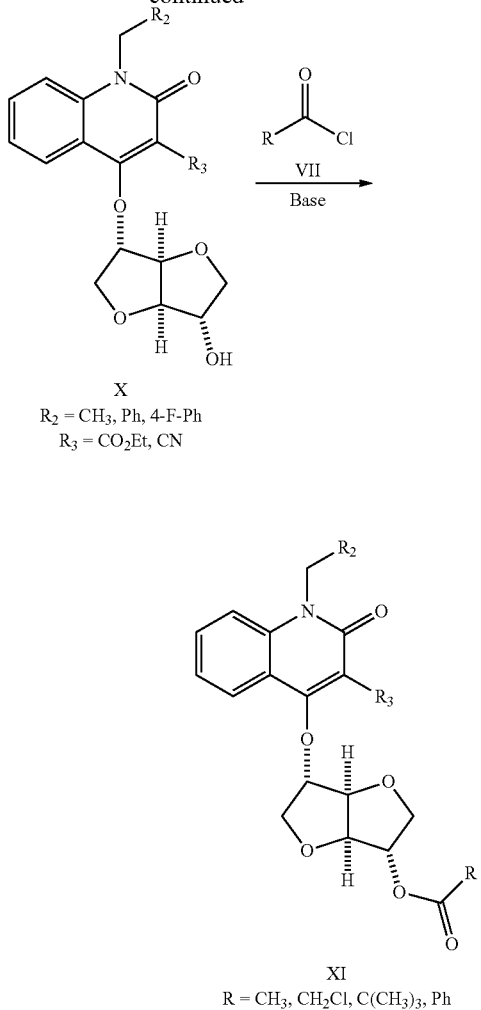

Compounds of the invention of general formula X can be prepared according to Scheme 3 and these targets can act as MIF inhibitors. Isosorbide was reacted with a reactive 1-substituted-4-hydroxy-2-oxo-1,2-dihydroquinoline derivative of type IX (where $R_2$ is methyl, phenyl, or 4-fluorophenyl and $R_3$ is $CO_2Et$ or CN) to provide compound X in the presence of 1.5 equivalents of triphenylphosphine and DIAD in the presence of a base such as DIPEA or TEA in an inert solvent such as THF and an inert atmosphere. The reactions may be performed at temperatures between 0° C. and room temperature or 0° C. and 65° C. in the case of $R_3$ is CN for several hours.

The reactive 4-hydroxy-2-oxo-1,2-dihydroquinoline derivative of type IX (where $R_2$ is methyl, phenyl, or 4-fluorophenyl and $R_3$ is $CO_2Et$ or CN) may be prepared following the literature procedures as described in a patent (WO 2007/109251 A2) and literature (Organic Process Research & Development 2004, 8, 802-807).

The esterification reaction of compound X to provide compounds of the invention of formula XI can be carried out in the presence of an acid chloride such as VII (where R is $CH_3$, $CH_2Cl$, $C(CH_3)_3$, or phenyl) in the presence of a base such as DIPEA or TEA in a convenient solvent such as methylene chloride in an inert atmosphere. The reactions may be performed between 0° C. and room temperature for several hours.

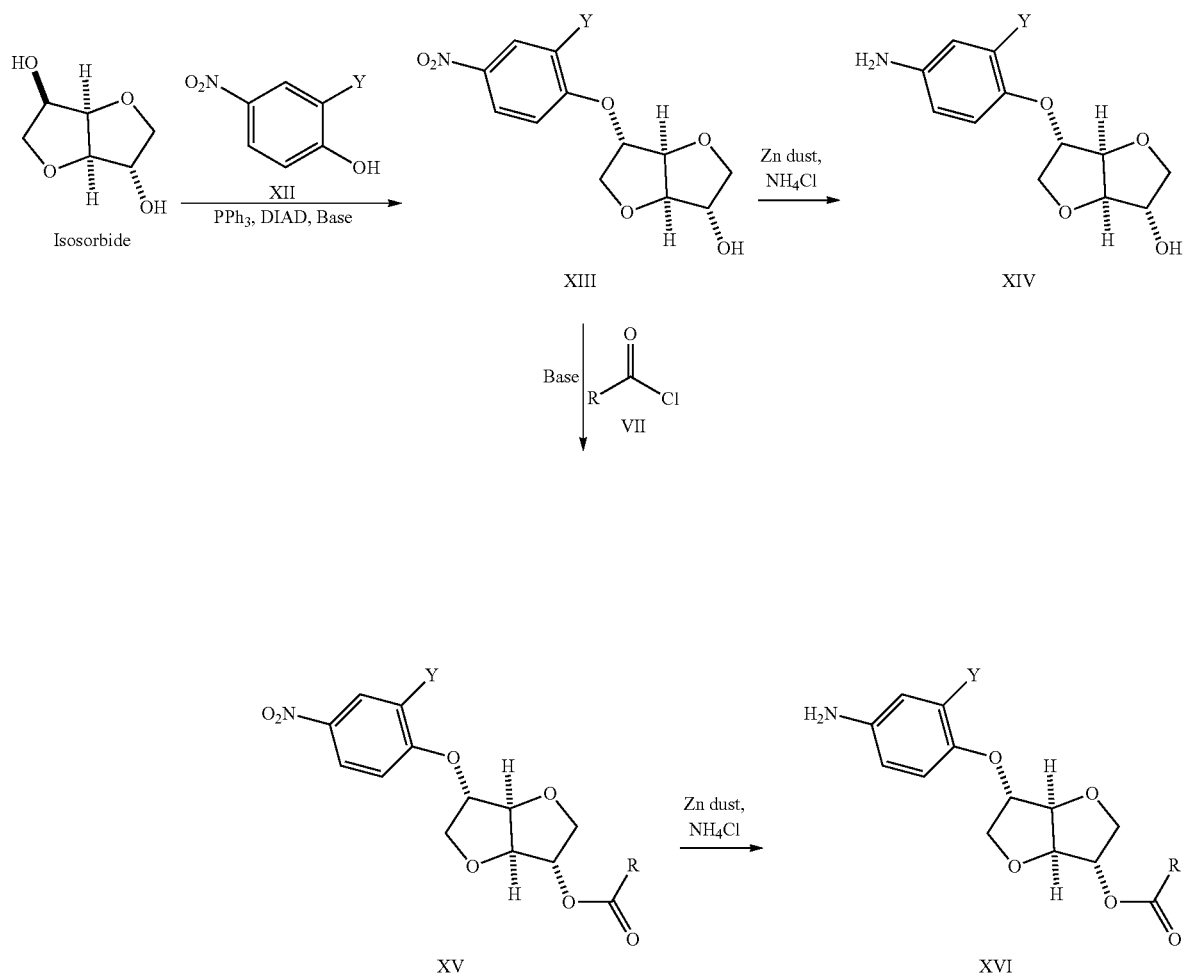

Compounds of the invention of formula XIII can be prepared from isosorbide and 4-nitrophenol or 2-substituted-4-nitrophenol of type XII (where Y is hydrogen, chlorine or fluorine) under the above mentioned Mitsunobu reaction conditions according to Scheme 4. The reduction of the nitro group of compound XIII to provide compound XIV can be carried out in the presence of excess zinc dust and ammonium chloride in a mixture of solvents such as methanol and water. The reaction may be performed at room temperature and 60° C. for several hours.

The esterification reaction of compound XIII to provide compound XV can be carried out in the presence of an acid chloride such as VII (R can be as described above) in the presence of a base such as DIPEA or TEA in a convenient solvent such as methylene chloride in an inert atmosphere. The reactions may be performed at temperatures between 0° C. and room temperature for several hours. The reduction of the nitro group of compound XV to give the amine intermediate XVI can be accomplished in the presence of an excess zinc dust and ammonium chloride. The reaction may be carried out in a mixture of solvents such as methanol and water at room temperature to 60° C. for several hours. Most importantly, these reduction reaction conditions are tolerable in the presence of a chloride substituent on the aromatic ring.

Compounds of the invention of formula XIV are versatile intermediates while a few applications of the amine intermediate are shown in Scheme 5 to prepare compounds of the interest of invention such as XVIII, XX, XXII and XXIV for the treatment of cancer and inflammatory diseases.

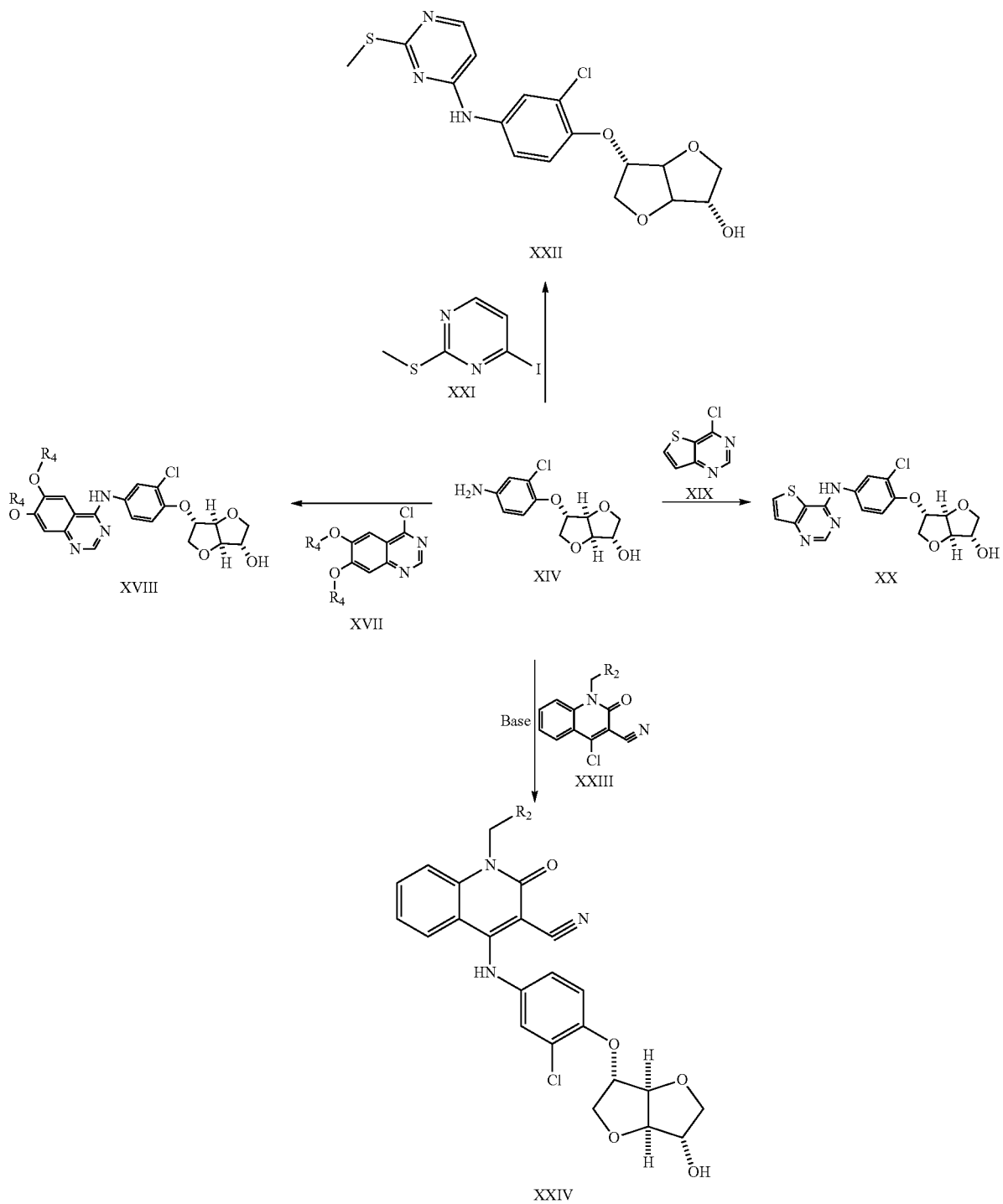

Scheme 5

Compounds of the invention of formula XVIII are novel EGFR inhibitors that can be prepared from aniline intermediate such as compound XIV and 4-chloro-6,7-dialkoxyquinazoline such as XVII. The reactions may be carried out in a convenient solvent such as iso-propanol. The reactions may be performed at elevated temperatures between 85° C. and 110° C. for several hours.

Similarly, compounds of invention of the formula XX can be prepared from aniline intermediates such as compound XIV and 4-chlorothieno[3,2-d]pyrimidines such as XIX. The reactions can be carried out in a convenient solvent such as iso-propanol. The reactions may be carried out at elevated temperatures between 85° C. and 110° C. for several hours. These derivatives may be novel kinase inhibitors.

Also, compounds of invention of the formula XXII can be prepared from aniline intermediates such as compound XIV and 4-iodo-2-methylsulfanylpyrimidines such as XXI. The reactions can be carried out in a convenient solvent such as iso-propanol and the reactions can be conducted at elevated temperatures between 85° C. and 110° C. for several hours. These derivatives may be novel kinase inhibitors.

Compounds of invention of the formula XXIV can be prepared from aniline intermediates such as compound XIV and reactive 1-substituted-4-chloro-2-oxo-3-cyano-1,2-dihydroquinoline intermediate such as XXIII. The reactions can be carried out in a convenient solvent such as iso-propanol and acetonitrile in the presence of a base such as TEA. The reactions can be carried out at elevated temperatures between 85° C. and 110° C. for several hours.

These derivatives can be novel MIF inhibitors.

pound XVI and 4-chlorothieno[3,2-d]pyrimidines such as XIX. The reactions may be conducted in a convenient solvent such as iso-propanol and the reactions may be carried out at temperatures between 85° C. and 110° C. for several hours. These derivatives may be novel kinase inhibitors.

Also, compounds of invention of the formula XXVII can be prepared from aniline intermediates such as compound XVI and 4-iodo-2-methylsulfanylpyrimidines such as XXI. The reactions can be performed in a convenient solvent such as iso-propanol and the reactions may be conducted at elevated temperatures between 85° C. and 110° C. for several hours. These derivatives may be novel kinase inhibitors.

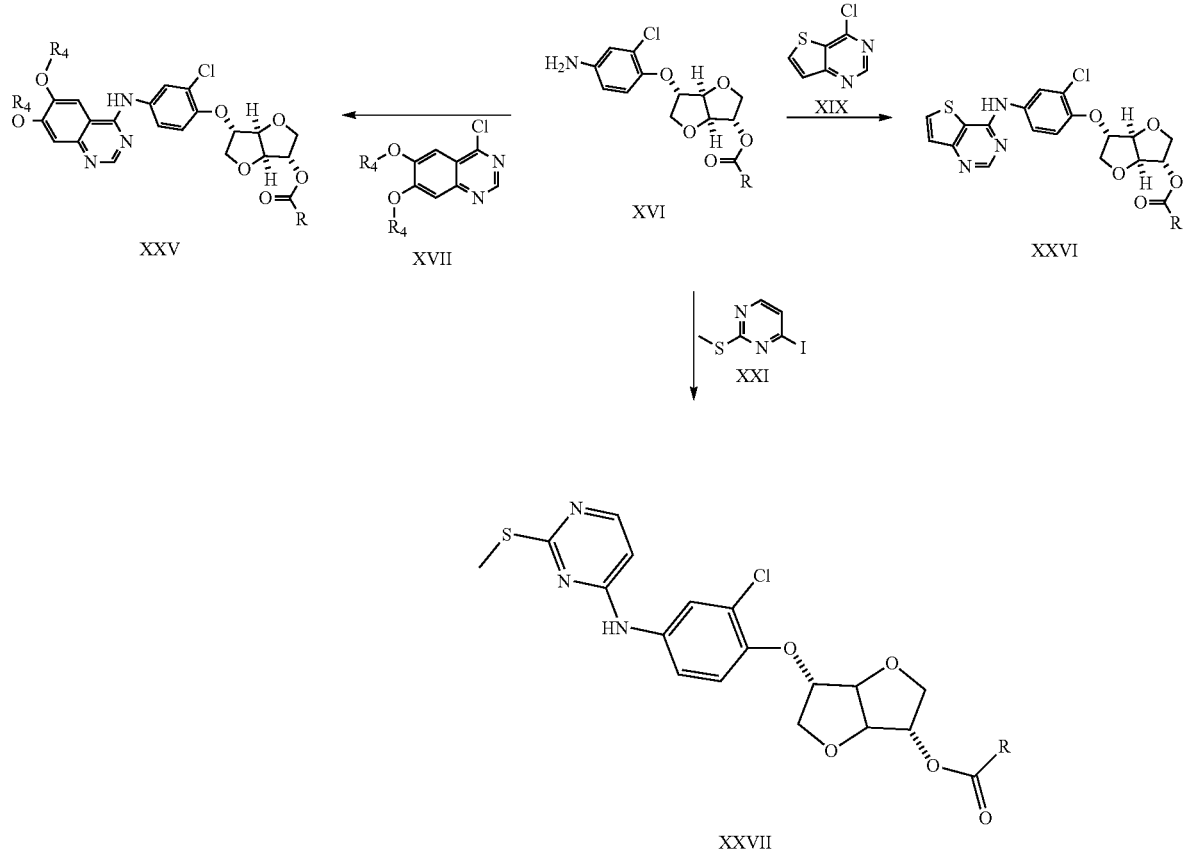

Compounds of the invention of formula XVI are also versatile intermediates while a few applications of one amine intermediate are shown in Scheme 6 above to prepare compounds of the invention of interest such as XXV, XXVI and XXVII for the treatment of cancer. Compounds of the invention of formula XXV are novel EGFR inhibitors and they can be prepared from aniline intermediate such as compound XVI and 4-chloro-6,7-dialkoxyquinazolines such as XVII. The reactions can be carried out in a convenient solvent such as iso-propanol. The reactions may be performed at elevated temperatures between 85° C. and 110° C. for several hours.

Similarly, compounds of invention of the formula XXVI can be prepared from aniline intermediates such as com-

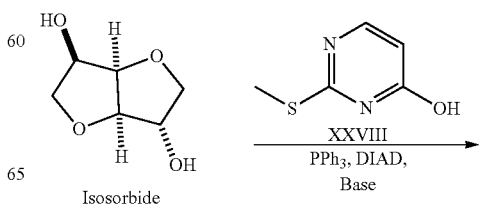

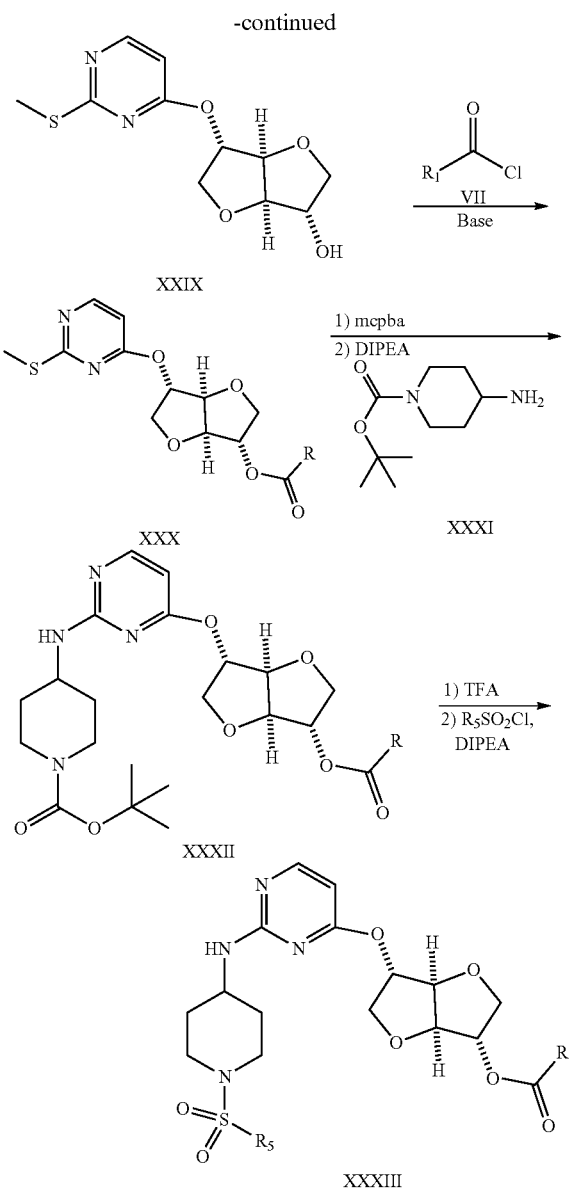

XXIX

XXX

XXXII

XXXIII

Compounds of the invention of formula XXIX can be prepared from isosorbide and 2-methylsulfanylpyrimidine-4-ol of type XXVIII under above described Mitsunobu reaction conditions according to Scheme 7. The esterification reaction of compound XXIX to provide compound XXX can be carried out in the presence of an acid chloride such as VII (R can be as described above) in the presence of a base such as DIPEA or TEA in an inert solvent such as methylene chloride in an inert atmosphere. The reactions may be performed at temperatures between 0° C. and room temperature for several hours.

The oxidation of methylsulfide of intermediate XXX to provide the methylsulfoxide of an intermediate can be performed in the presence of mcpba (m-chloroperbenzoic acid). The reaction may be conducted in an inert solvent such as methylene chloride at 0° C. and room temperature for several hours.

The nucleophilic substitution of methylsulfoxide in intermediate XXX to provide compound XXXII can be performed with 4-amino-1-Boc-piperidine such as XXXI in the presence of a base such as DIPEA or TEA. The reaction can be carried out in a convenient solvent such as DMF or NMP. The reactions may be conducted at elevated temperatures between 120° C. and 140° C. for several hours.

Removal of the tert-butylcarbamate protective group in the compounds of formula XXXII to give a secondary piperidine intermediate can be carried out by treating the compound of formula XXXII with trifluoroacetic acid in an inert solvent such as methylene chloride. The reactions can be conducted at temperatures 0° C. and room temperature for several hours. Sulfonamides of the invention of formula XXXIII are conveniently prepared by treating the secondary piperidine intermediate with alkyl or arylsulfonyl chlorides such as $R_5SO_2Cl$ in the presence of a base such as DIPEA or TEA in an inert solvent such as tetrahydrofuran or methylene chloride. The reactions may be conducted at 0° C. and room temperature for several hours.

Scheme 8

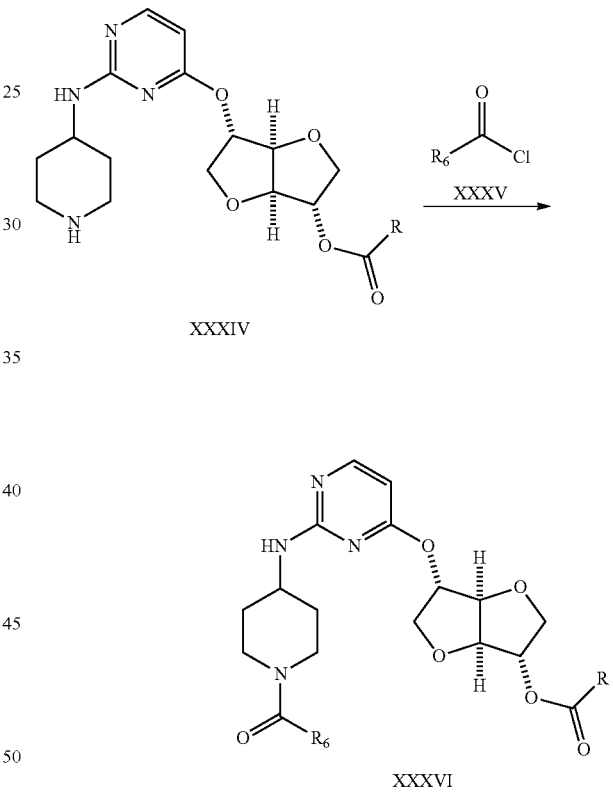

XXXIV

XXXVI

Compounds of the invention of formula XXXVI (where $R_6$ is lower alkyl, substituted lower alkyl, phenyl, or substituted phenyl) can be prepared according to Scheme 8 above. In this process, the reaction of secondary piperidine of compound XXXIV with acid chloride of type XXXV to provide the amide derivatives of type XXXVI in the presence of a base such as DIPEA or TEA in an inert solvent such as methylene chloride. The reactions may be conducted at 0° C. and room temperature for several hours.

Scheme 9

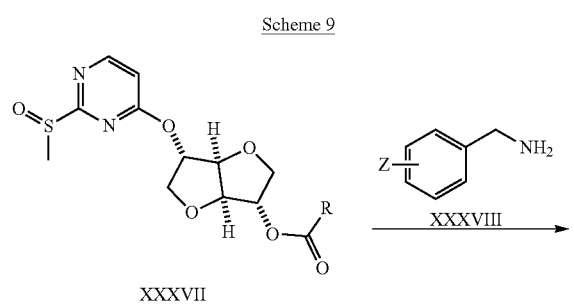

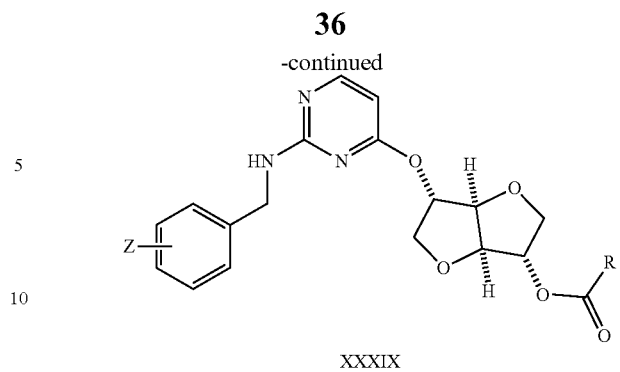

Compounds of the invention of formula XXXIX (where Z is halogen, preferably chlorine or fluorine, lower alkoxy, or lower alkylsulfonyl) can be prepared according to Scheme 9 above. In this process, the methylsulfoxide intermediate of compound XXXVII is reacted with the benzyl amine of type XXXVIII to produce the compounds of the formula XXXIX in the presence of a base such as DIPEA or TEA in a convenient solvent such as NMP or DMF. The reactions may be conducted at 120° C. and 140° C. for several hours.

Scheme 10

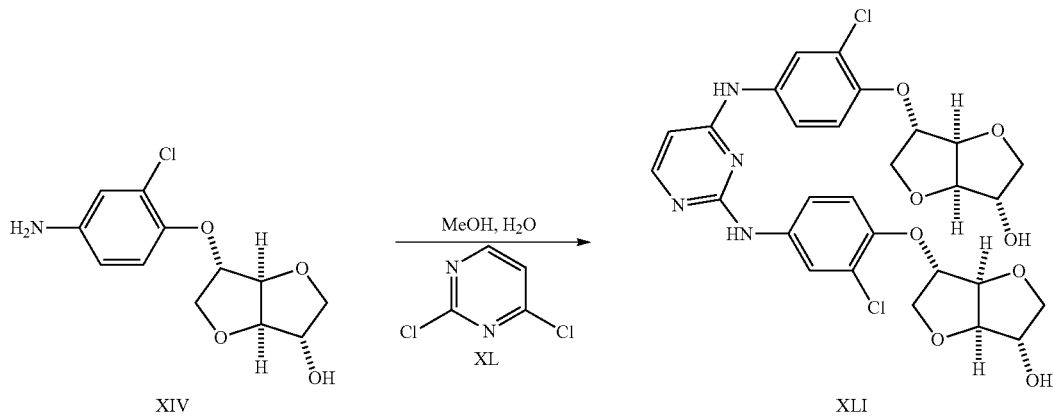

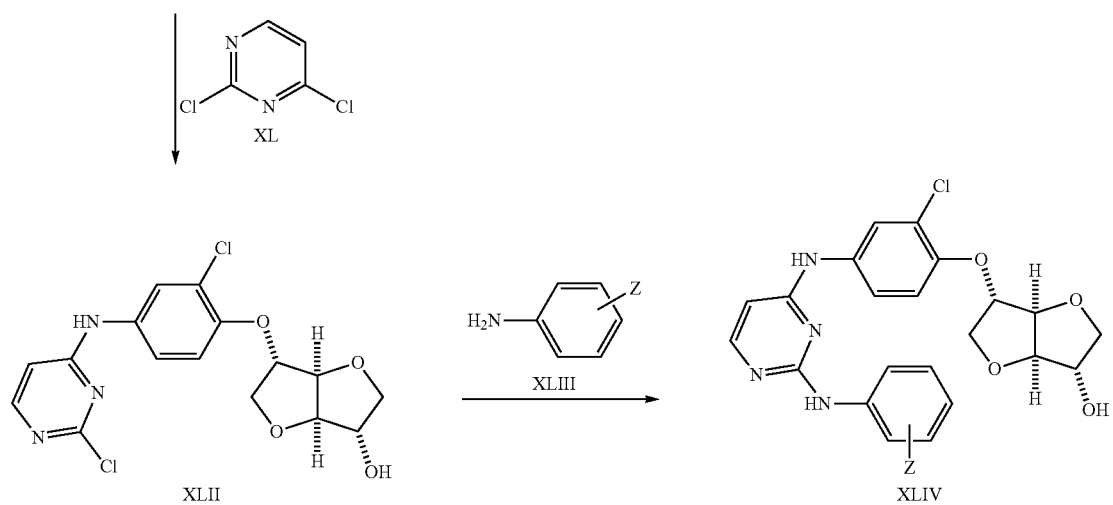

Compounds of the invention of formula XIV are also versatile intermediates and another such application is shown in Scheme 10 above to prepare novel compounds of the invention of interest such as XLI and XLIV for the treatment of cancer and inflammation.

Compounds of invention of the formula XLI can be prepared by the reaction of 2-3 equivalents of aniline intermediates such as compound XIV and 2,4-dichloropyrimidines such as XL. The reactions can be performed in a convenient solvent system such as methanol and water in 1:1 ratio. The reactions may be conducted at elevated temperatures between 120° C. and 140° C. for several hours.

Compounds of the intermediates of formula XLII can also be prepared by the reaction of 1.1 equivalents of aniline intermediates such as compound XIV and 1.0 equivalent of 2,4-dichloropyrimidines such as XL. The reactions can be conducted in a convenient solvent system such as methanol and water in 1:1 or 1:2 ratios. The reactions can be carried out at room temperature and 60° C. for several hours.

The compounds of the invention of formula XLIV can be obtained by the reaction of intermediates of formula XLII with the substituted anilines or substituted heteroaromatic amines such as formula XLIII. The reactions may be carried out in appropriate solvents such as NMP or DMF or methanol and water. The reactions may be performed at elevated temperatures between 120° C. and 140° C. for several hours. The above mentioned derivatives may be novel kinase inhibitors.

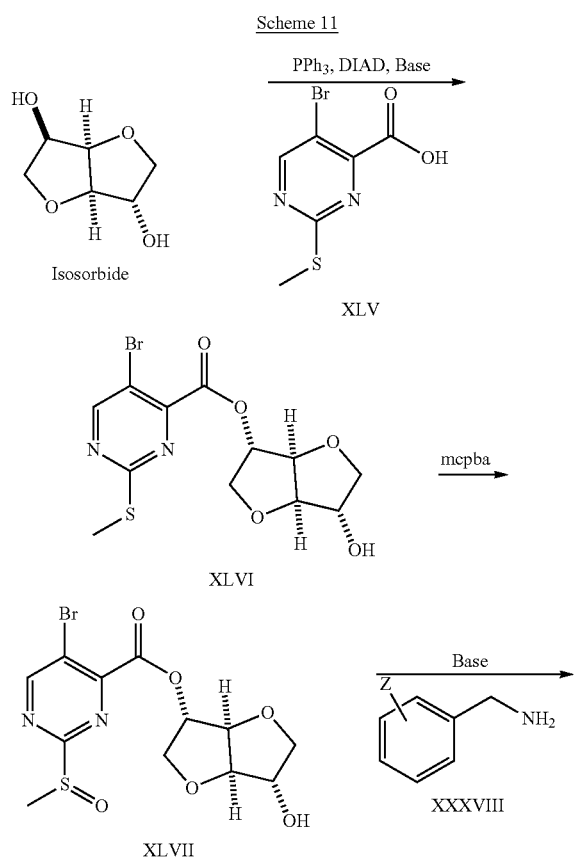

Scheme 11

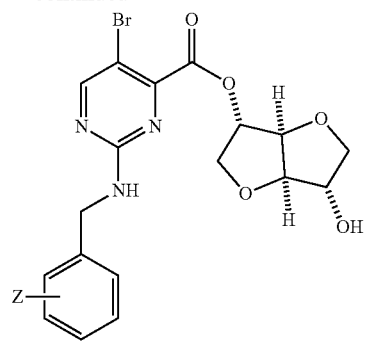

XLVIII

Compounds of the invention of formula XLVI can be prepared from isosorbide and 5-bromo-2-(methylthio)-pyrimidine-4-carboxylic acid XLV under the above mentioned Mitsunobu reaction conditions according to Scheme 11 above.

The oxidation of the methylsulfide of intermediate XLVI to provide the methylsulfoxide of intermediate XLVII can be performed in the presence of mcpba. The reaction may be carried out in an inert solvent such as methylene chloride at 0° C. and room temperature for several hours.

The compounds of the invention of formula XLVIII can be prepared by the reaction of the methylsulfoxide intermediate XLVII with the benzyl amine of type XXXVIII (where Z is chlorine, fluorine, methylsulfonyl) in the presence of a base such as DIPEA or TEA in a convenient solvent such as NMP or DMF. The reactions may be performed at 120° C. and 140° C. temperature for several hours.

Scheme 12

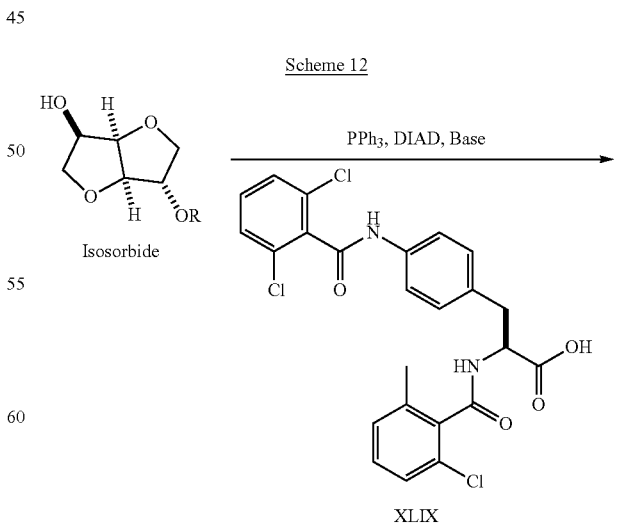

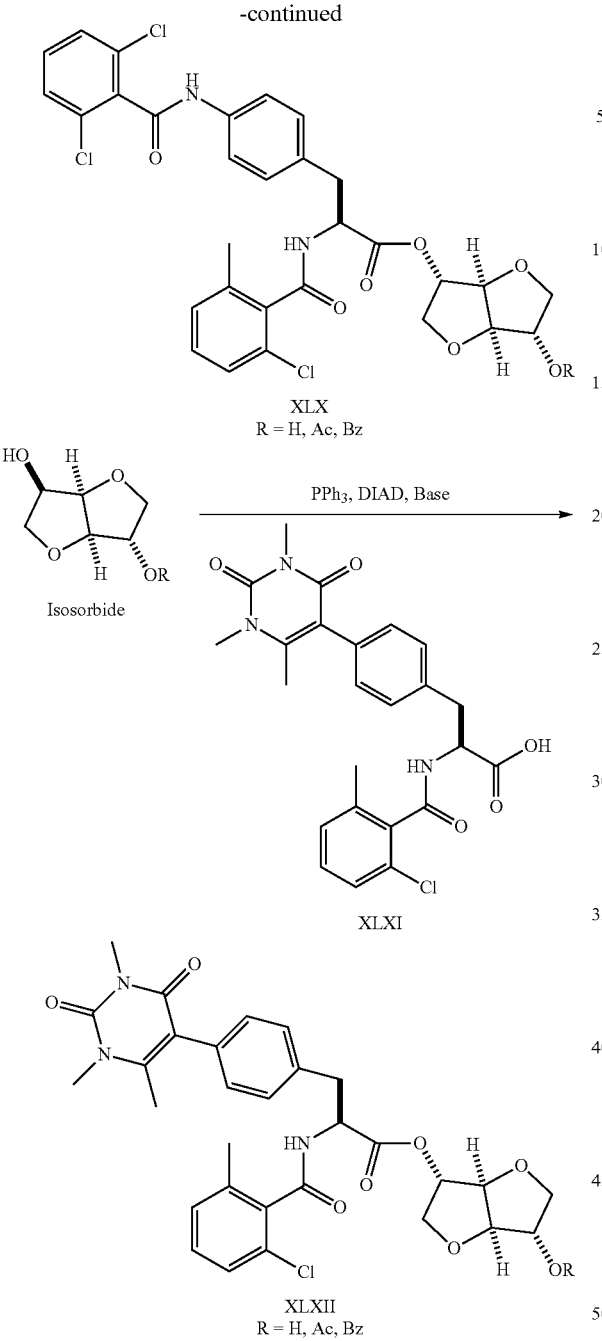

XLX
R = H, Ac, Bz

Isosorbide

PPh₃, DIAD, Base

XLXI

XLXII
R = H, Ac, Bz

Compounds of the invention of formula XLX or XLXII can be prepared from isosorbide or isosorbide 2-acetate or isosorbide 2-benzyl ether and (2S)-2-[(2-chloro-5-methyl-benzoyl)amino]-3-[4-[(2,6-dichlorobenzoyl)amino]phenyl] propanoic acid XLIX (for preparation, see WO1999/10312) or (2S)-2-[(2-chloro-6-methyl-benzoyl)amino]-3-[4-(1,3,4-trimethyl-2,6-dioxo-pyrimidin-5-yl)phenyl]propanoic acid XLXI (For preparation, see U.S. Ser. No. 00/638,0387B 1) under the above mentioned Mitsunobu reaction conditions according to Scheme 12 above.

In this invention of formula XLX and XLXII, the isoidide derivative can act as a prodrug moiety and the active compound can be released in the body by esterases and the active compounds XLIX and XLXI are potent alpha4 beta1 and alpha4 beta7 integrin antagonists (see the patents (WO1999/10312 and U.S. Ser. No. 00/638,0387B 1).

General Methods for Compound Synthesis

Example A

Synthesis of ethyl 4-[[(3S,3aR,6S,6aR)-3-hydroxy-2,3,3a,5,6,6a-hexahydrofuro[3,2-b]furan-6-yl]oxy]-1-ethyl-2-oxo-1,2-dihydroquinoline-3-carboxylate

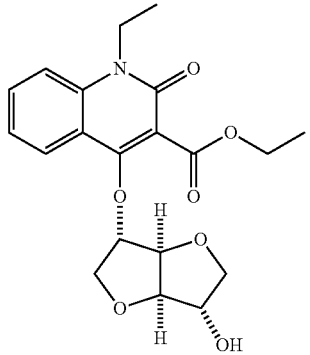

Step 1: Preparation of 1-ethyl-isatoic anhydride

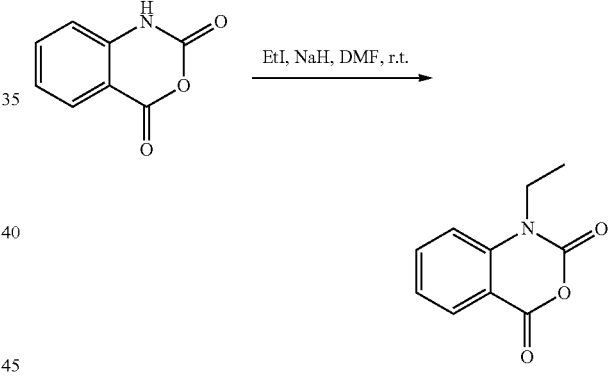

A 250 mL 2-neck round bottom flask was charged with isatoic anhydride (16.3 g, 100 mmol) and then DMF (100 mL) was added followed by portion wise (2 times) addition of sodium hydride (4.4 g, 183 mmol, 60% dispersion in oil) for 5 minutes under an argon atmosphere. During addition of NaH, the reaction was exothermic and lot of gas evolved with foam.

The resulting brown suspension was stirred for 1 h and then neat iodoethane (15.6 g, 8.04 mL, 110 mmol) was added drop-wise over 5 minutes. The resulting light brown thick slurry was stirred at room temperature for 15 h at which time a lot of solids precipitated (paste). Then, water was added drop-wise for 10 minutes after which another 100 mL of water was added and the resulting slurry was stirred for 1 h. Then, it was poured into 500 mL of water and stirred for 30 minutes. The resulting solids were collected by filtration and washed with water and hexanes.

After air drying, 15 g (79%) of 1-ethyl isatoic anhydride was isolated as an off-white solid.

Step 2: Preparation of ethyl 1-ethyl-4-hydroxy-2-oxo-1,2-dihydroquinoline-3-carboxylate

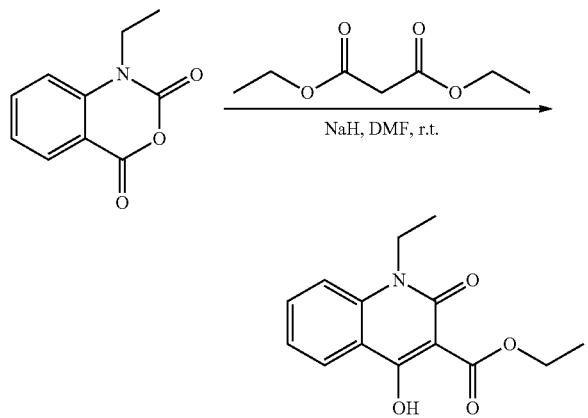

A 250 mL 2-neck round bottom flask was charged with 1-ethyl isatoic anhydride (7.64 g, 40 mmol) and DMF (80 mL) was added followed by diethylmalonate (7.05 g, 6.7 mL, 44 mmol). Then, the solid sodium hydride (3.87 g, 161.33 mmol, 60% dispersion in oil) was added in two portions during 15 minute intervals at room temperature under an argon atmosphere. The resulting light yellowish foam suspension was stirred for 5 h. During this period, foam like solids formed that floated on the top. After 5 h at room temperature, TLC analysis of the reaction mixture indicated the absence of starting material.

Then, water (5 mL) was added very slowly which produced a lot of foam. After 10 minutes of stirring, the light yellow suspension was poured into 1.0N HCl (20 mL) and diluted with water (100 mL).

Then, the organic compound was extracted into EA (2×100 mL). The combined extracts were washed with water (2×100 mL), brine solution (100 mL), and dried over anhydrous $MgSO_4$. Filtration of the drying agent and concentration produced crude brown oil which was dissolved in EA (~5 mL) and then diluted with hexanes. The resulting brown solution was stored in the refrigerator overnight. The resulting solids were collected by decanting the mother liquor and the desired ethyl 1-ethyl-4-hydroxy-2-oxo-1,2-dihydroquinoline-3-carboxylate (3.0 g) was isolated as off-white solids. The mother liquor was purified using an ISCO (330 g) column chromatography to obtain another 4 g with a total of 7.0 g (70%) of ethyl 1-ethyl-4-hydroxy-2-oxo-1,2-dihydroquinoline-3-carboxylate. LC/MS calcd. for $C_{14}H_{15}NO_4$ [(M+H)$^+$] 262, obsd. 262.

Step 3: Preparation of ethyl 4-[[(3S,3aR,6S,6aR)-3-hydroxy-2,3,3a,5,6,6a-hexahydrofuro[3,2-b]furan-6-yl]oxy]-1-ethyl-2-oxo-1,2-dihydroquinoline-3-carboxylate

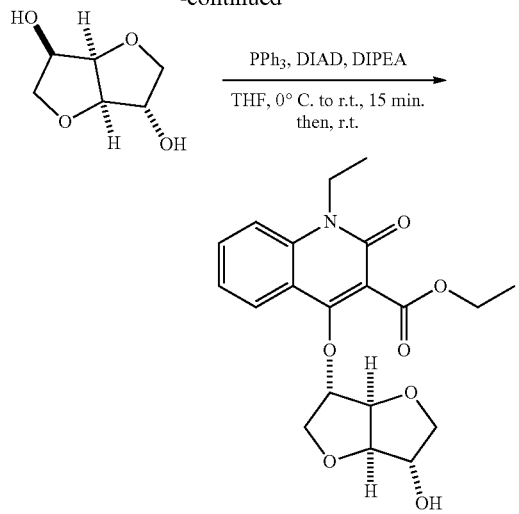

To a solution of triphenylphosphine (393 mg, 1.5 mmol) in THF (10 mL) in a 25 mL 2-neck RB flask was added di-isopropylazodicarboxylate (303 mg, 295 uL, 1.5 mmol) at 0-5° C. (ice+water) for 2-3 minutes under an argon atmosphere. The resulting light yellow suspension was stirred for 10 minutes at this temperature. Then, a solution of ethyl 1-ethyl-4-hydroxy-2-oxo-1,2-dihydroquinoline-3-carboxylate (260 mg, 1.0 mmol) in THF (6 mL) was added dropwise for 5 minutes. After 2 minutes, the cooling bath was removed to allow the reaction mixture to warm to room temperature where it was stirred for 10 minutes.

Then, a solution of isosorbide (176 mg, 1.2 mmol) in THF (5 mL) was slowly added followed by the neat DIPEA (194 mg, 261 uL, 1.5 mmol) at room temperature. The resulting light yellow suspension was stirred for 48 h and TLC (1:1, Hex:EA) analysis of the reaction mixture indicated the appearance of a new spot. Then, the solvent was removed under vacuum and the crude residue was purified using an ISCO (120 g) column chromatography to obtain 350 mg (90%) ethyl 4-[[(3S,3aR,6S,6aR)-3-hydroxy-2,3,3a,5,6,6a-hexahydrofuro[3,2-b]furan-6-yl]oxy]-1-ethyl-2-oxo-1,2-dihydroquinoline-3-carboxylate as a colorless paste. $^1$H-NMR (CDCl$_3$): δ 8.04 (d, J=7.3 Hz, 1H), 7.56 (t, J=7.3 Hz, 1H), 7.25 (d, J=7.8 Hz, 1H), 7.15 (t, J=7.4 Hz, 1H), 5.02 (d, J=2.8 Hz, 1H), 4.93 (d, J=3.4 Hz, 1H), 4.64 (d, J=3.4 Hz, 1H), 4.5-4.25 (m, 5H), 4.15 (d, J=10.1 Hz, 1H), 3.92-3.75 (m, 3H), 1.45-1.25 (m, 6H). LC/MS calcd. for $C_{20}H_{23}NO_7$ [(M+H)$^+$] 390, obsd. 390.

Example B

Preparation of ethyl 4-[[(3S,3aR,6S,6aR)-6-acetoxy-2,3,3a,5,6,6a-hexahydrofuro[3,2-b]furan-3-yl]oxy]-1-ethyl-2-oxo-1,2-dihydroquinoline-3-carboxylate

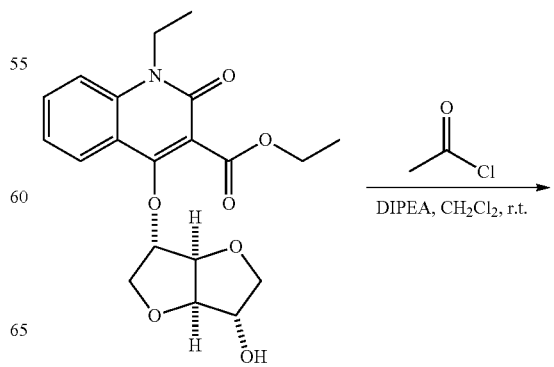

-continued

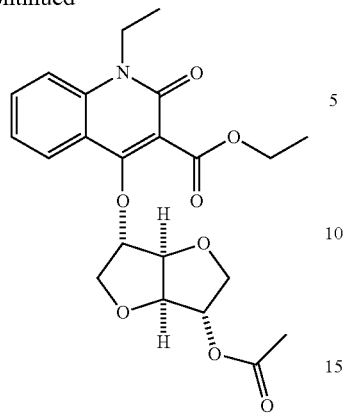

To a colorless solution of ethyl 4-[[(3S,3aR,6S,6aR)-3-hydroxy-2,3,3a,5,6,6a-hexahydrofuro[3,2-b]furan-6-yl]oxy]-1-ethyl-2-oxo-1,2-dihydroquinoline-3-carboxylate (155 mg, 0.4 mmol) in dichloromethane (10 mL) in a 25 mL 2-neck RB flask were added first acetyl chloride (79 mg, 72 uL, 1.0 mmol) then followed by the neat DIPEA (258 mg, 348 uL, 2.0 mmol) at 0-5° C. under an argon atmosphere. After addition of DIPEA, the reaction mixture turned into a light brown solution. The resulting light brown solution was allowed to warm to room temperature without removing the cooling bath and stirred for 15 h.

Then, it was diluted with water and the organic compound was extracted into dichloromethane. The combined extracts were washed with brine solution and dried over anhydrous magnesium sulfate. Filtration and concentration resulted in a crude dark brown oil that was purified using an ISCO (80 g) column chromatography to yield 138 mg (80%) of ethyl 4-[[(3S,3aR,6S,6aR)-6-acetoxy-2,3,3a,5,6,6a-hexahydrofuro[3,2-b]furan-3-yl]oxy]-1-ethyl-2-oxo-1,2-dihydroquinoline-3-carboxylate as a white solid. $^1$H-NMR (CDCl$_3$): δ 8.04 (d, J=7.3 Hz, 1H), 7.56 (t, J=7.3 Hz, 1H), 7.25 (d, J=7.8 Hz, 1H), 7.15 (t, J=7.3 Hz, 1H), 5.15 (d, J=2.8 Hz, 1H), 5.01 (d, J=3.4 Hz, 1H), 4.81 (d, J=3.4 Hz, 1H), 4.68 (d, J=3.9 Hz, 1H), 4.4 (q, J=6.2 Hz, 2H), 4.22 (q, J=6.3 Hz, 2H), 4.12 (d, J=10.1 Hz, 1H), 3.95-3.85 (m, 2H), 3.81 (dd, J=8.4, 3.4 Hz, 1H), 2.04 (s, 3H), 1.32 (t, J=7.5 Hz, 3H), 1.25 (t, J=7.5 Hz, 3H). LC/MS calcd. for C$_{22}$H$_{25}$NO$_8$ [(M+H)$^+$] 432, obsd. 432.

Example C

Preparation of ethyl 4-[[(3S,3aR,6S,6aR)-6-(2-chloroacetyl)oxy-2,3,3a,5,6,6a-hexahydrofuro[3,2-b]furan-3-yl]oxy]-1-ethyl-2-oxo-1,2-dihydroquinoline-3-carboxylate

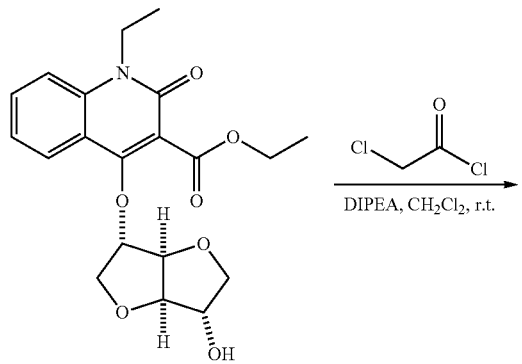

-continued

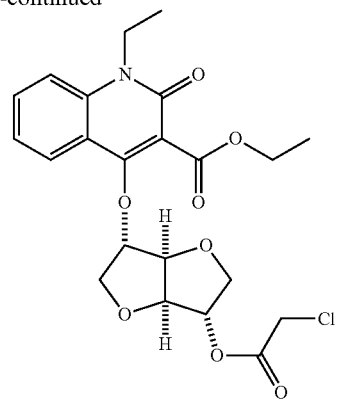

To a colorless solution of ethyl 4-[[(3S,3aR,6S,6aR)-3-hydroxy-2,3,3a,5,6,6a-hexahydrofuro[3,2-b]furan-6-yl]oxy]-1-ethyl-2-oxo-1,2-dihydroquinoline-3-carboxylate (195 mg, 0.5 mmol) in dichloromethane (10 mL) in a 25 mL 2-neck RB flask were added first 2-chloroacetyl chloride (113 mg, 80 uL, 1.0 mmol) then followed by the neat DIPEA (258 mg, 348 uL, 2.0 mmol) at 0-5° C. under an argon atmosphere. After addition of DIPEA, the reaction mixture turned into a dark brown solution. The resulting dark brown solution was allowed to warm to room temperature without removing the cooling bath and stirred for 15 h.

Then, it was diluted with water and the organic compound was extracted into dichloromethane. The combined extracts were washed with brine solution and dried over anhydrous magnesium sulfate. Filtration and concentration gave the crude dark brown oil which was purified using an ISCO (80 g) column chromatography to afford 198 mg (85%) of ethyl 4-[[(3S,3aR,6S,6aR)-6-(2-chloroacetyl)oxy-2,3,3a,5,6,6a-hexahydrofuro[3,2-b]furan-3-yl]oxy]-1-ethyl-2-oxo-1,2-dihydroquinoline-3-carboxylate as a light brown viscous oil. $^1$H-NMR (CDCl$_3$): δ 7.98 (d, J=7.3 Hz, 1H), 7.71 (t, J=7.3 Hz, 1H), 7.42 (d, J=7.8 Hz, 1H), 7.24 (t, J=8.4 Hz, 1H), 5.28 (d, J=2.8 Hz, 1H), 5.05 (d, J=3.4 Hz, 1H), 4.76 (d, J=3.4 Hz, 1H), 4.65 (d, J=3.4 Hz, 1H), 4.42 (q, J=6.4 Hz, 2H), 4.31 (q, J=6.4 Hz, 2H), 4.18 (d, J=10.1 Hz, 1H), 4.01 (s, 2H), 3.95-3.85 (m, 2H), 3.81 (dd, J=8.4, 3.4 Hz, 1H), 1.5-1.15 (m, 6H). LC/MS calcd. for C$_{22}$H$_{24}$ClNO$_8$ [(M+H)$^+$] 466, obsd. 466.

Example D

Preparation of ethyl 4-[[(3S,3aS,6aR)-2,3,3a,6a-tetrahydrofuro[3,2-b]furan-3-yl]oxy]-1-ethyl-2-oxo-1,2-dihydroquinoline-3-carboxylate

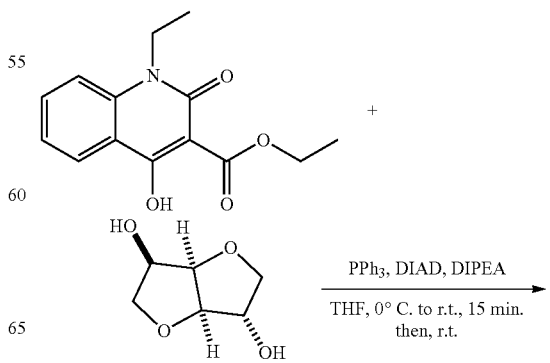

-continued

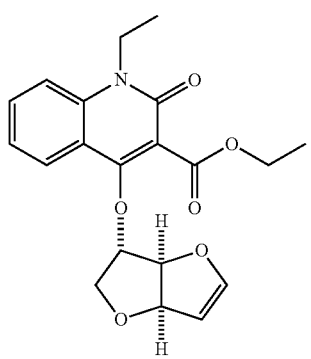

To a solution of triphenylphosphine (787 mg, 3.0 mmol) in THF (5 mL) in a 25 mL 2-neck RB flask was added di-isopropylazodicarboxylate (606 mg, 591 uL, 3.0 mmol) at 0-5° C. (ice+water) for 2-3 minutes under an argon atmosphere. The resulting light yellow suspension was stirred for 10 minutes at this temperature. Then, a solution of ethyl 1-ethyl-4-hydroxy-2-oxo-1,2-dihydroquinoline-3-carboxylate (261 mg, 1.0 mmol) in THF (6 mL) was added dropwise for 5 minutes. After 2 minutes, the cooling bath was removed to allow the reaction mixture to warm to room temperature where it was stirred for 10 minutes.

Then, a solution of isosorbide (88 mg, 0.6 mmol) in THF (2 mL) was slowly added followed by the neat DIPEA (388 mg, 522 uL, 1.5 mmol) at room temperature. The resulting thick yellow suspension was stirred for 15 h after which it was still a yellow suspension, but less viscous compared to the initial appearance. After another 24 h of stirring it became a light orange colored solution and after being stirred for another 48 h by which time it turned to a light yellow solution. After total 72 h, TLC (1:1, Hex:EA) analysis of the reaction mixture indicated the appearance of a new and less polar spot. The solvent was removed under vacuum and the crude residue was purified using an ISCO (80 g) column chromatography to provide 220 mg (99%, based on the amount of isosorbide used) of ethyl 4-[[(3S,3aS,6aR)-2,3,3a,6a-tetrahydrofuro[3,2-b]furan-3-yl]oxy]-1-ethyl-2-oxo-1,2-dihydroquinoline-3-carboxylate as a light yellow amorphous solid. $^1$H-NMR (CDCl$_3$): δ 8.0 (d, J=7.3 Hz, 1H), 7.56 (t, J=7.8 Hz, 1H), 7.32 (d, J=7.3 Hz, 1H), 7.24 (t, J=8.4 Hz, 1H), 6.5 (d, J=3.3 Hz, 1H), 5.55 (dd, J=4.9, 2.8 Hz, 1H), 5.1-5.01 (m, 3H), 4.49 (q, J=6.4 Hz, 2H), 4.28 (q, J=6.4 Hz, 2H), 4.18 (d, J=10.1 Hz, 1H), 3.49 (dd, J=9.8, 3.4 Hz, 1H), 1.5-1.2 (m, 6H). LC/MS calcd. for C$_{20}$H$_{21}$NO$_6$ [(M+H)$^+$] 372, obsd. 372.

Example E

Synthesis of ethyl 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carboxylate

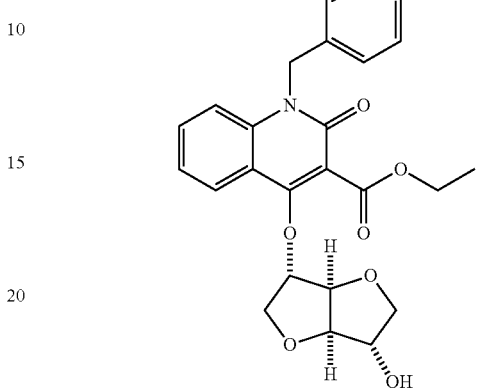

Step 1: Preparation of 1-benzyl isatoic anhydride

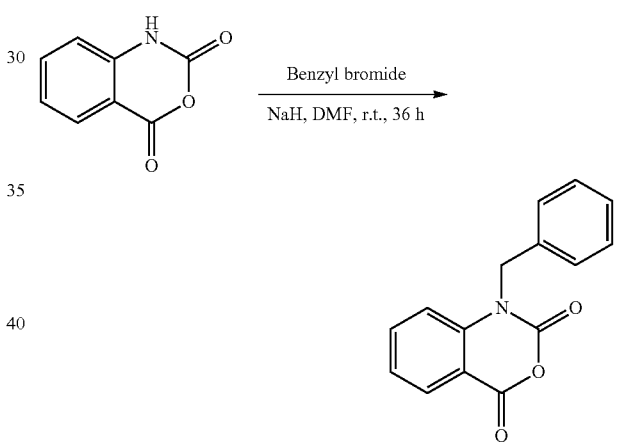

A 250 mL 2-neck round bottom flask was charged with isatoic anhydride (14.69 g, 90 mmol) and then DMF (100 mL) was added followed by the addition of sodium hydride (3.99 g, 166 mmol, 60% dispersion in oil) in 2-portions at 15 minute intervals under an argon atmosphere. During addition of NaH, the reaction was exothermic and lot of gas evolved with foam. The resulting brown suspension was stirred for 1 h and then the neat benzyl bromide (16.93 g, 11.77 mL, 99 mmol) was added for 5-10 minutes. The resulting light brown thick slurry was stirred at room temperature for 36 h.

Then, the brown reaction mixture was quenched by dropwise addition of water (10 mL) for 2 minutes and the reaction mixture was stirred for 10 minutes. Then, more water (~50 mL) was added and the resulting brown oil was poured into 500 mL of water while stirring with spatula. The precipitated brown solids were collected by filtration and washed with water and hexanes. After air drying, 21.48 g (94%) of 1-benzyl isatoic anhydride was isolated as an off-white solid.

Step 2: Preparation of ethyl 1-benzyl-4-hydroxy-2-oxo-1,2-dihydroquinoline-3-carboxylate Step 3: Preparation of ethyl 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carboxylate

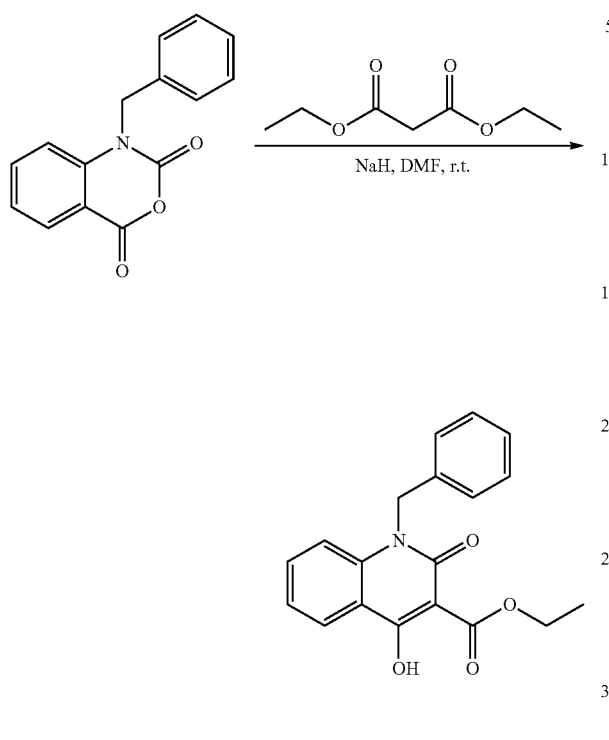

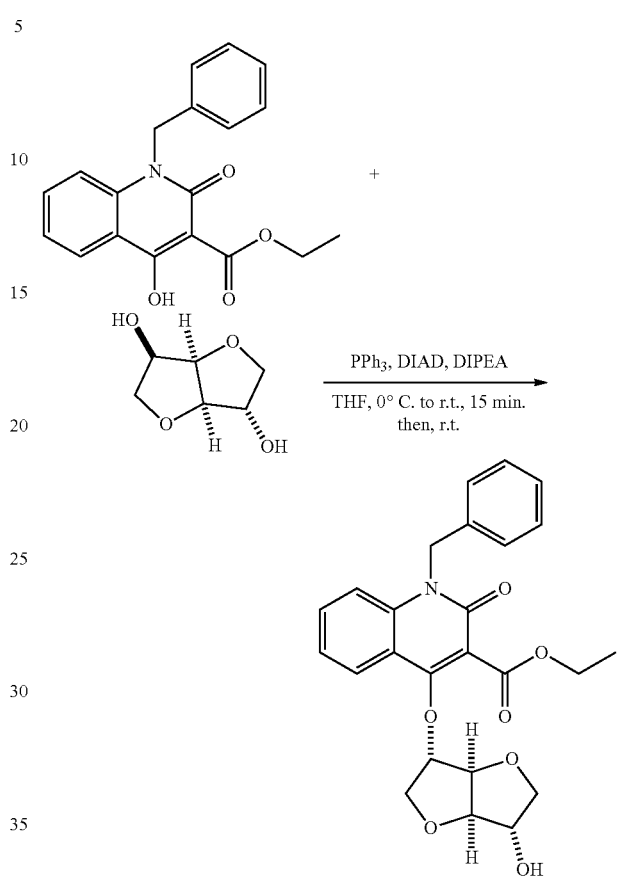

A 250 mL 2-neck round bottom flask was charged with 1-benzyl isatoic anhydride (10.13 g, 40 mmol) and then DMF (80 mL) was added followed by diethylmalonate (7.05 g, 6.7 mL, 44 mmol) at room temperature under an argon atmosphere. Then, the solid sodium hydride (3.87 g, 161.33 mmol, 60% dispersion in oil) was added in 2-portions at 20 minute intervals at room temperature. The resulting light yellowish foam suspension was stirred for 15 h and then the reaction mixture was quenched slowly with ~10 mL of water (lot of foam formed). After 15 minutes stirring, another 10 mL of water was added. After 15 minutes stirring, the foam suspension was poured into 500 mL of water while stirring with spatula. The neutral organic impurities were extracted into EA (2×250 mL) and the basic aqueous layer was neutralized with 1.0N HCl and the resulting white suspension was extracted into EA (2×150 mL).

The combined extracts were washed with brine solution (100 mL) and dried over anhydrous $MgSO_4$. Filtration of the drying agent and concentration yielded crude viscous oil which was dissolved in EA (20-30 mL) in hot conditions and then diluted with hexanes (50-60 mL) until a light precipitate appeared. The resulting yellow solution was stored in the freezer for 2 days. The resulting light brown solids were collected by filtration and washed with hexanes. After air drying, 6.0 g (46%) of ethyl 1-benzyl-4-hydroxy-2-oxo-1,2-dihydroquinoline-3-carboxylate was isolated as off-white solids. LC/MS calcd. for $C_{19}H_{17}NO_4$ [(M+H)$^+$] 324, obsd. 324.

To a solution of triphenylphosphine (3.93 g, 15 mmol) in THF (100 mL) in a 500 mL 3-neck RB flask was added di-isopropylazodicarboxylate (3.03 g, 2.95 mL 15 mmol) at 0-5° C. (ice+water) for 5-7 minutes under an argon atmosphere. The resulting light yellow suspension was stirred for 10-15 minutes at this temperature. Then, a solution of ethyl 1-benzyl-4-hydroxy-2-oxo-1,2-dihydroquinoline-3-carboxylate (3.23 g, 10 mmol) in THF (100 mL) was added drop-wise for 10 minutes. After 2 minutes, the cooling bath was removed to allow the reaction mixture to warm to room temperature where it was stirred for 10-15 minutes.

Then, a solution of isosorbide (1.75 g, 12 mmol) in THF (70 mL) was slowly added followed by the neat DIPEA (1.94 g, 2.61 mL, 15 mmol) at room temperature. The resulting light yellow solution was stirred for 36 h at which time TLC (1:1, Hex:EA) analysis of the reaction mixture indicated the appearance of a new spot. Then, the solvent was removed under vacuum and the crude residue was purified using an ISCO (330 g) column chromatography to obtain 3.43 g (76%) of ethyl 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carboxylate as a white solid. $^1$H-NMR (CDCl$_3$): δ 7.98 (d, J=7.3 Hz, 1H), 7.51 (t, J=7.3 Hz, 1H), 7.3-7.15 (m, 7H), 5.51 (s, 2H), 5.21 (d, J=2.8 Hz, 1H), 4.98 (d, J=3.4 Hz, 1H), 4.62 (d, J=3.4 Hz, 1H), 4.42 (q, J=6.5 Hz, 2H), 4.3 (d, J=3.3 Hz, 1H), 4.25 (d, J=10.1 Hz, 1H), 3.99-3.9 (m, 3H), 1.48 (t, J=7.5 Hz, 3H). LC/MS calcd. for $C_{25}H_{25}NO_7$ [(M+H)$^+$] 452, obsd. 452.

Example F

Preparation of ethyl 4-[[(3S,3aR,6S,6aR)-6-acetoxy-2,3,3a,5,6,6a-hexahydrofuro[3,2-b]furan-3-yl]oxy]-1-benzyl-2-oxo-1,2-dihydroquinoline-3-carboxylate

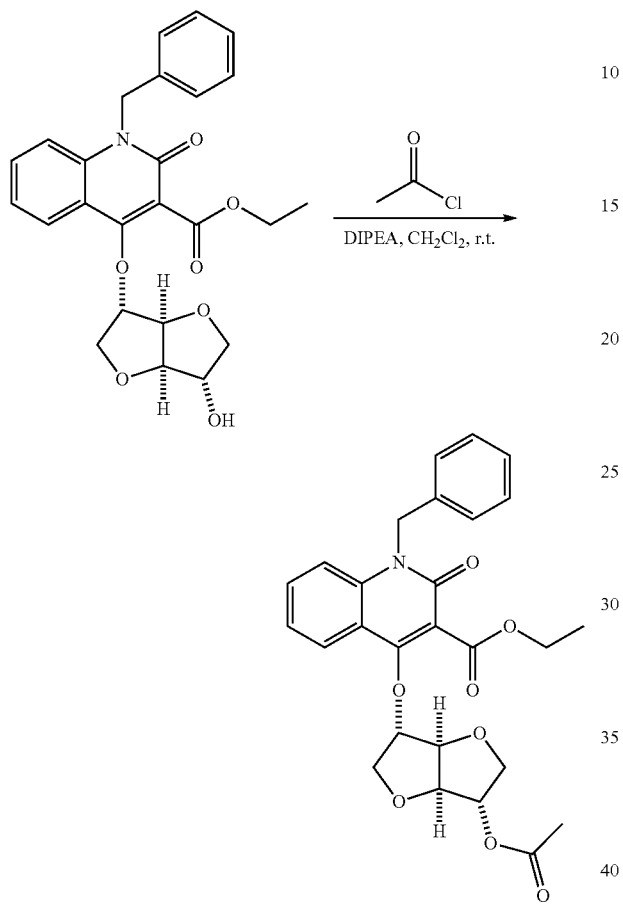

To a colorless solution of ethyl 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carboxylate (113 mg, 0.25 mmol) in dichloromethane (5 mL) in a 25 mL 2-neck RB flask were added first 2-acetyl chloride (39 mg, 35 uL, 0.5 mmol) followed by the neat DIPEA (129 mg, 174 uL, 1.0 mmol) at room temperature under an argon atmosphere. After the addition of DIPEA, the reaction mixture became a light brown solution. The resulting light brown solution was stirred for 48 h at which time TLC (1:1, Hex:EA) analysis of the reaction mixture indicated the appearance of a new less polar spot.

Then, it was diluted with water and the organic compound was extracted into dichloromethane (2×50 mL). The combined organic extracts were washed with brine solution and dried over anhydrous MgSO$_4$. Filtration and concentration gave the crude residue which was purified using an ISCO (80 g) column chromatography to afford 99 mg (80%) of ethyl 4-[[(3S,3aR,6S,6aR)-6-acetoxy-2,3,3a,5,6,6a-hexahydrofuro[3,2-b]furan-3-yl]oxy]-1-benzyl-2-oxo-1,2-dihydroquinoline-3-carboxylate as an amorphous off-white solid. $^1$H-NMR (CDCl$_3$): δ 7.98 (d, J=7.3 Hz, 1H), 7.51 (t, J=7.3 Hz, 1H), 7.34-7.2 (m, 7H), 5.52 (s, 2H), 5.25 (d, J=2.8 Hz, 1H), 5.15 (d, J=3.4 Hz, 1H), 5.0 (d, J=3.4 Hz, 1H), 4.83 (d, J=3.4 Hz, 1H), 4.52 (q, J=6.2 Hz, 2H), 4.32 (d, J=10.1 Hz, 1H), 4.2-4.1 (m, 2H), 4.01 (dd, J=8.4, 3.4 Hz, 1H), 2.15 (s, 3H), 1.51 (t, J=7.5 Hz, 3H). LC/MS calcd. for C$_{27}$H$_{27}$NO$_8$ [(M+H)$^+$] 494, obsd. 494.

Example G

Preparation of ethyl 4-[[(3S,3aR,6S,6aR)-6-(2-chloroacetyl)oxy-2,3,3a,5,6,6a-hexahydrofuro[3,2-b]furan-3-yl]oxy]-1-benzyl-2-oxo-1,2-dihydroquinoline-3-carboxylate

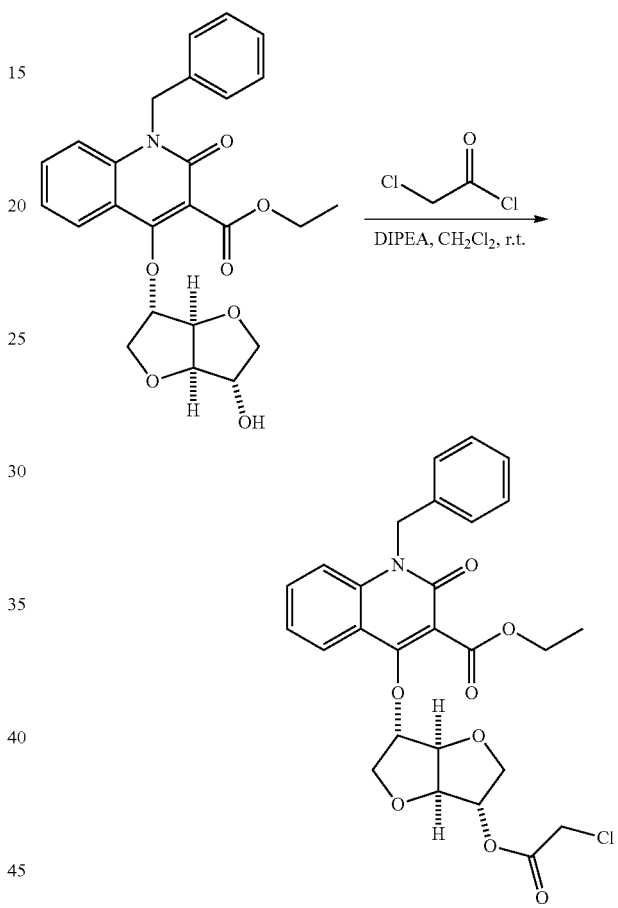

To a colorless solution of ethyl 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carboxylate (3.24 g, 7.2 mmol) in dichloromethane (100 mL) in a 250 mL 2-neck RB flask were added first 2-chloroacetyl chloride (972 mg, 685 uL, 8.6 mmol) followed by the neat triethylamine (1.81 g, 2.49 mL, 18 mmol) at 0-5° C. under an argon atmosphere. The resulting light brown solution was allowed to warm to room temperature without removing the cooling bath and stirred for 36 h.

Then, it was diluted with water and the organic compound was extracted into dichloromethane (2×100 mL). The combined organic extracts were washed with brine solution and dried over anhydrous MgSO$_4$. Filtration and concentration provided a crude residue that was purified using an ISCO (330 g) column chromatography to afford 1.89 g (50%) of ethyl 4-[[(3S,3aR,6S,6aR)-6-(2-chloroacetyl)oxy-2,3,3a,5,6,6a-hexahydrofuro[3,2-b]furan-3-yl]oxy]-1-benzyl-2-oxo-1,2-dihydroquinoline-3-carboxylate as an amorphous white solid. ¹H-NMR (CDCl₃): δ 7.95 (d, J=8.4 Hz, 1H), 7.63 (t, J=8.4 Hz, 1H), 7.45 (d, J=8.9 Hz, 1H), 7.33-7.3 (m, 3H), 7.24 (t, J=6.7 Hz, 1H), 7.21 (d, J=7.3 Hz, 2H), 5.5 (s, 2H), 5.2 (d, J=3.4 Hz, 1H), 4.96 (d, J=2.3 Hz, 1H), 4.84 (d, J=3.9 Hz, 1H), 4.81 (d, J=3.4 Hz, 1H), 4.42 (s, 2H), 4.3 (q, J=6.2 Hz, 2H), 4.12 (d, J=10.6 Hz, 1H), 3.97 (dd, J=10.6, 3.4 Hz, 1H), 3.92 (d, J=10.1 Hz, 1H), 3.89 (dd, J=10.6, 3.4 Hz, 1H), 1.45 (t, J=7.5 Hz, 3H). LC/MS calcd. for $C_{27}H_{26}ClNO_8$ [(M−H)⁻] 526, obsd. 526.

Example H

Preparation of ethyl 4-[[(3S,3aS,6aR)-2,3,3a,6a-tetrahydrofuro[3,2-b]furan-3-yl]oxy]-1-benzyl-2-oxo-1,2-dihydroquinoline-3-carboxylate

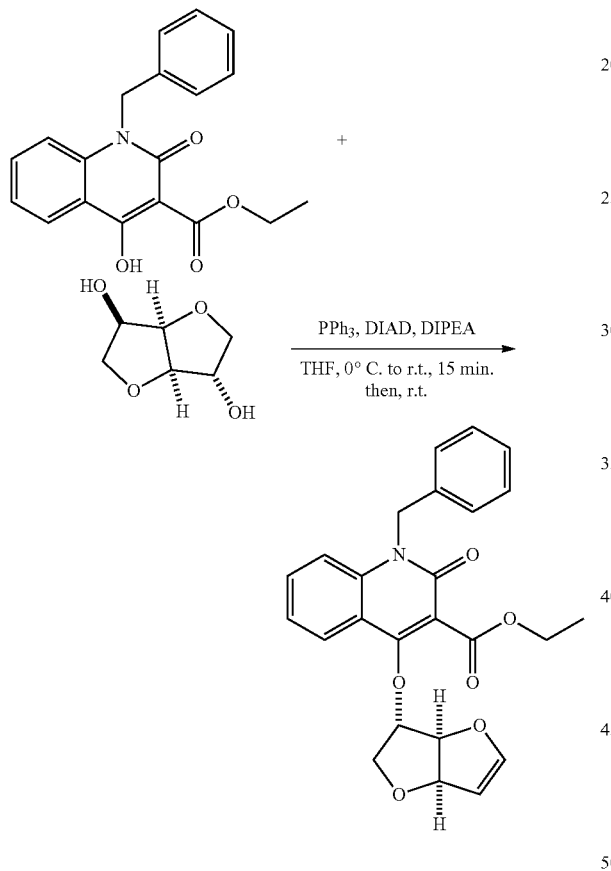

To a solution of triphenylphosphine (787 mg, 3.0 mmol) in THF (10 mL) in a 50 mL 2-neck RB flask was added di-isopropylazodicarboxylate (606 mg, 591 uL, 3.0 mmol) at 0-5° C. (ice+water) for 2-3 minutes under an argon atmosphere. The resulting light yellow suspension was stirred for 10 minutes at this temperature. Then, a solution of ethyl 1-benzyl-4-hydroxy-2-oxo-1,2-dihydroquinoline-3-carboxylate (323 mg, 1.0 mmol) in THF (6 mL) was added drop-wise for 5 minutes. After 2 minutes, the cooling bath was removed to allow the reaction mixture to warm to room temperature and it was stirred for 10 minutes.

Then, a solution of isosorbide (146 mg, 1.0 mmol) in THF (5 mL) was slowly added followed by the neat DIPEA (388 mg, 522 uL, 3.0 mmol) at room temperature. The resulting thick yellow suspension was stirred for 15 h when it became an orange color suspension after it was stirred for 7 days. Then, the solvent was removed under vacuum and the crude mixture was purified using an ISCO (80 g) column chromatography to afford 364 mg (84%) of ethyl 4-[[(3S,3aS,6aR)-2,3,3a,6a-tetrahydrofuro[3,2-b]furan-3-yl]oxy]-1-benzyl-2-oxo-1,2-dihydroquinoline-3-carboxylate as a light yellow amorphous solid. ¹H-NMR (CDCl₃): δ 8.0 (d, J=8.3 Hz, 1H), 7.5 (t, J=8.5 Hz, 1H), 7.34-7.2 (m, 7H), 6.56 (s, 1H), 5.56 (d, J=3.5 Hz, 1H), 5.5 (s, 2H), 5.2-5.02 (m, 2H), 4.5 (q, J=6.4 Hz, 2H), 4.2 (d, J=10.1 Hz, 1H), 4.15-4.05 (m, 1H), 3.51 (dd, J=10.1, 3.4 Hz, 1H), 1.4 (t, J=7.5 Hz, 3H). LC/MS calcd. for $C_{25}H_{23}NO_6$ [(M+H)⁺] 434, obsd. 434.

Example I

Synthesis of ethyl 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carboxylate

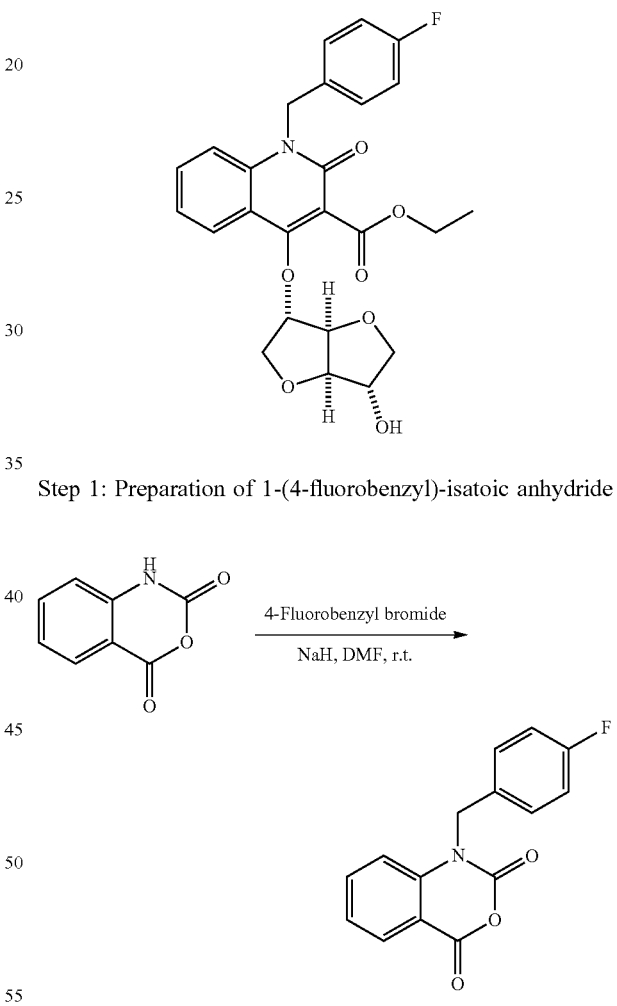

Step 1: Preparation of 1-(4-fluorobenzyl)-isatoic anhydride

A 250 mL 2-neck round bottom flask was charged with isatoic anhydride (14.69 g, 90 mmol) and then DMF (100 mL) was added followed by the addition of sodium hydride (3.99 g, 166 mmol, 60% dispersion in oil) in 2-portions at 15 minute intervals under an argon atmosphere. During addition of NaH, the reaction was exothermic and lot of gas evolved with foam. The resulting brown suspension was stirred for 1 h and then the neat 4-fluorobenzyl bromide (18.71 g, 12.33 mL, 99 mmol) was added for 10 minutes. The light brown foam suspension was stirred at room temperature for 48 h.

Then, the brown reaction mixture was quenched by dropwise addition of water (~5 mL) for 2 minutes and the reaction mixture was stirred for 10 minutes. Then, the brown solution was poured into 600 mL of water while stirring with spatula. The resulting solids were crushed and collected by filtration. The mother liquor was extracted one time with EA. The filtered solids were dissolved in EA (~200 mL) in hot conditions after which it was combined with the extracted EA. It contained some water that separated. The EA layer was dried over MgSO$_4$, filtered and concentrated to obtain the crude product which was dissolved again in ~100 mL of EA in hot conditions then diluted with hexanes.

The solution was cooled to room temperature. The resulting solids were collected by filtration and washed with hexanes. After air drying, 16.7 g (68%) of 1-(4-fluorobenzyl)-isatoic anhydride was isolated as off-white solid.

Step 2: Preparation of ethyl 1-[(4-fluorophenyl)methyl]-4-hydroxy-2-oxo-1,2-dihydroquinoline-3-carboxylate

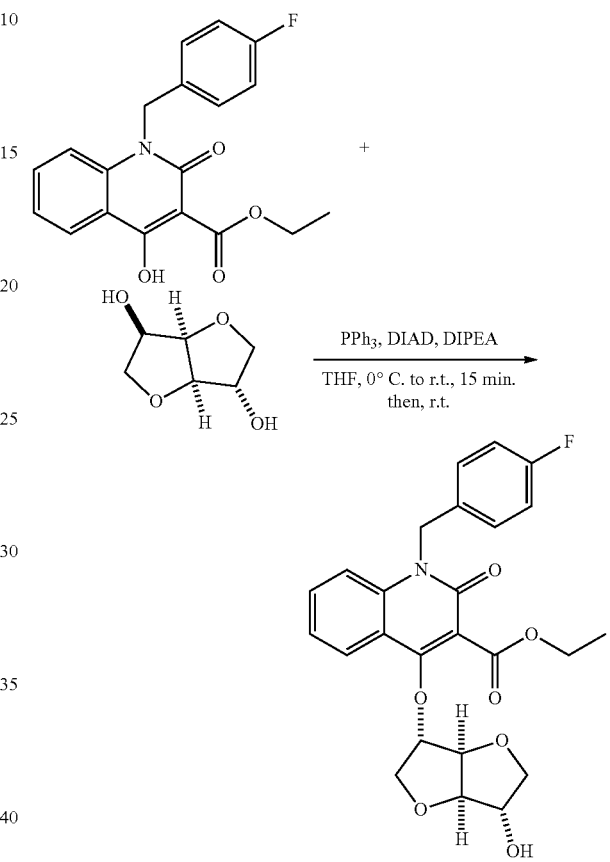

A 100 mL 2-neck round bottom flask was charged with 1-[(4-fluorophenyl)methyl]-isatoic anhydride (5.42 g, 20 mmol) and then DMF (40 mL) was added followed by diethylmalonate (3.52 g, 3.34 mL, 22 mmol) at room temperature under an argon atmosphere. Then, the solid sodium hydride (1.94 g, 80.6 mmol, 60% dispersion in oil) was added in two portions during 20 minute intervals at room temperature. The resulting light yellowish foam suspension was stirred for 15 h and then the reaction mixture was quenched slowly with ~10 mL of water (lot of foam was formed). After 15 minutes of stirring, the foam suspension was poured into 200 mL of water while stirring with a spatula.

The neutral organic impurities were extracted into EA (2×100 mL) and the basic aqueous layer was neutralized with 1.0N HCl while the resulting white suspension was extracted into EA (2×150 mL). The combined extracts were washed with brine solution (100 mL) and dried over anhydrous MgSO$_4$. Filtration of the drying agent and concentration yielded a crude viscous oil that was dissolved in EA (10 mL) at hot condition and then diluted with hexanes (25 mL). A precipitate started to form at room temperature, and it was stored in the freezer for 1 h. The resulting light brown solids were collected by filtration and washed with hexanes. After air drying, 4.33 g (63%) of ethyl 1[(4-fluorophenyl)methyl]-4-hydroxy-2-oxo-1,2-dihydroquinoline-3-carboxylate was isolated as white solids. LC/MS calcd. for $C_{19}H_{16}FNO_4$ [(M−H)$^-$] 340, obsd. 340.

Step 3: Preparation of ethyl 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carboxylate

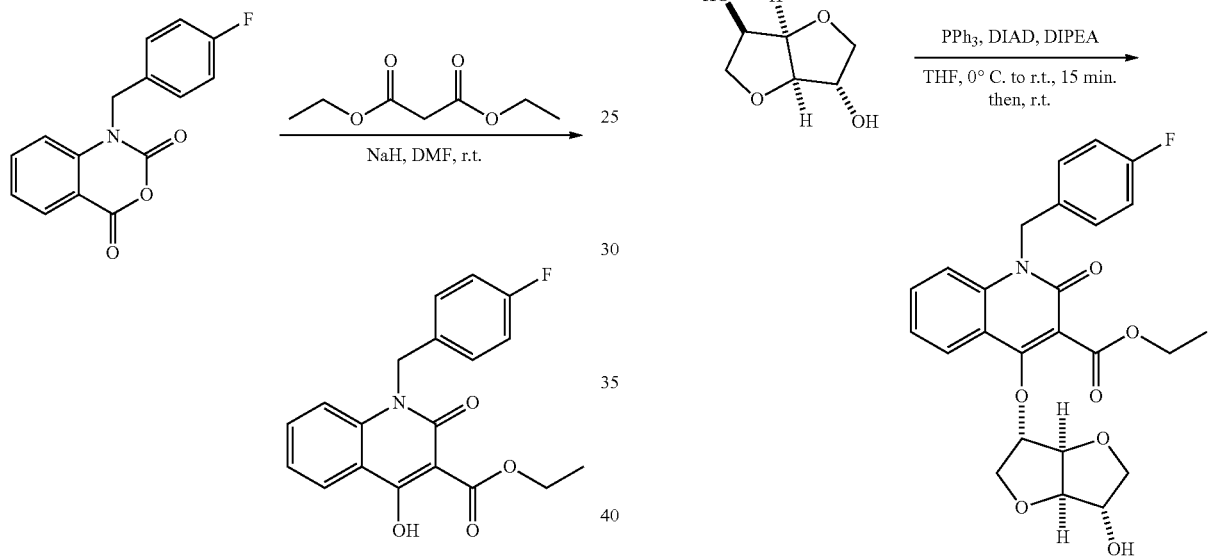

To a solution of triphenylphosphine (787 mg, 3 mmol) in THF (20 mL) in a 100 mL 2-neck RB flask was added di-isopropylazodicarboxylate (607 mg, 591 uL, 3 mmol) at 0-5° C. (ice+water) for 5-7 minutes under an argon atmosphere. The resulting light yellow suspension was stirred for 10-15 minutes at this temperature. Then, a solution of ethyl 1-[(4-fluorophenyl)methyl]-4-hydroxy-2-oxo-1,2-dihydroquinoline-3-carboxylate (683 mg, 2 mmol) in THF (15 mL) was added drop-wise for 5 minutes. After 2 minutes, the cooling bath was removed to allow the reaction mixture to warm to room temperature where it was stirred for 10-15 minutes.

Then, a solution of isosorbide (452 mg, 2.4 mmol) in THF (10 mL) was slowly added followed by the neat DIPEA (388 mg, 522 uL, 3 mmol) at room temperature. The resulting light yellow suspension was stirred for 36 h at which time TLC (1:1, Hex:EA) analysis of the reaction mixture indicated the appearance of a new spot. Then, the solvent was removed under vacuum and the crude residue was purified using an ISCO (220 g) column chromatography to obtain 713 mg (76%) of ethyl 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carboxylate as a white solid. $^1$H-NMR (DMSO-d6): δ 7.93 (d, J=7.3

Hz, 1H), 7.65-7.54 (m, 2H), 7.47 (d, J=7.8 Hz, 1H), 7.32 (t, J=7.3 Hz, 1H), 7.28-7.25 (m, 2H), 7.16 (t, J=8.4 Hz, 1H), 5.47 (s, 2H), 5.29 (d, J=3.4 Hz, 1H), 4.89 (d, J=2.8 Hz, 1H), 4.76 (d, J=3.4 Hz, 1H), 4.56 (d, J=3.4 Hz, 1H), 4.34 (q, J=6.2 Hz, 2H), 4.13 (s, 1H), 4.05-4.02 (m, 1H), 3.8 (dd, J=10.1, 2.8 Hz, 1H), 3.73 (dd, J=8.4, 3.4 Hz, 1H), 3.72 (d, J=8.4 Hz, 1H), 1.3 (t, J=7.5 Hz, 3H). LC/MS calcd. for $C_{25}H_{24}FNO_7$ [(M+H)$^+$] 470, obsd. 470.

Example J

Preparation of ethyl 4-[[(3S,3aR,6S,6aR)-6-(2-chloroacetyl)oxy-2,3,3a,5,6,6a-hexahydrofuro[3,2-b]furan-3-yl]oxy]-1-[(4-fluorophenol)methyl]-2-oxo-1,2-dihydroquinoline-3-carboxylate

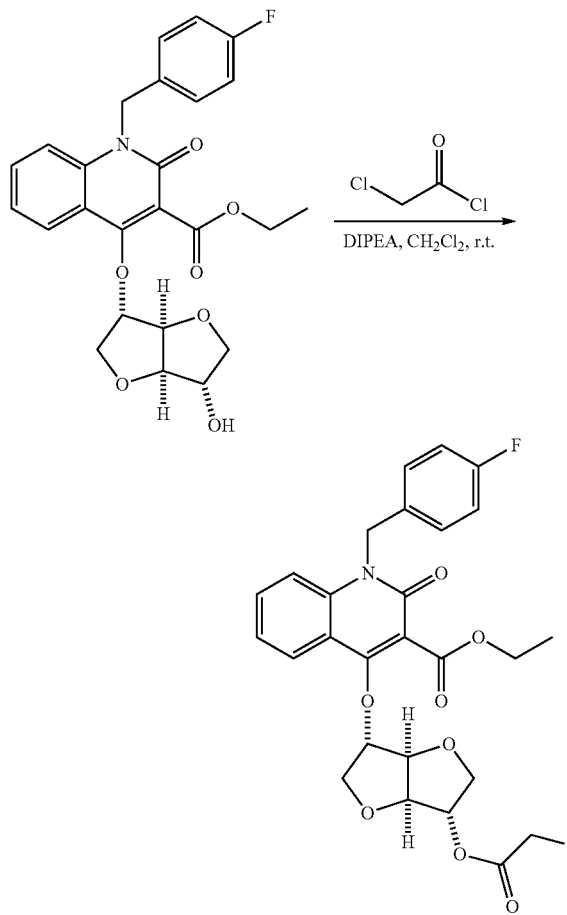

To a colorless solution of ethyl 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carboxylate (519 mg, 1.1 mmol) in dichloromethane (30 mL) in a 100 mL 2-neck RB flask were added first 2-chloroacetyl chloride (155 mg, 110 uL, 1.38 mmol) followed by the neat triethylamine (279 mg, 385 uL, 2.76 mmol) at 0-5° C. under an argon atmosphere. The resulting light brown solution was allowed to warm to room temperature without removing the cooling bath and stirred for 15 h.
Then, it was diluted with water and the organic compound was extracted into dichloromethane (2×50 mL). The combined organic extracts were washed with brine solution and dried over anhydrous MgSO$_4$. Filtration and concentration gave the crude residue which was purified using an ISCO (220 g) column chromatography to afford 240 mg (40%) of ethyl 4-[[(3S,3aR,6S,6aR)-6-(2-chloroacetyl)oxy-2,3,3a,5,6,6a-hexahydrofuro[3,2-b]furan-3-yl]oxy]-1-[(4-fluorophenyl)methyl]-2-oxo-1,2-dihydroquinoline-3-carboxylate as an amorphous white solid. $^1$H-NMR (DMSO-d6): δ 7.94 (d, J=7.8 Hz, 1H), 7.65-7.62 (m, 2H), 7.47 (d, J=8.4 Hz, 1H), 7.32 (t, J=7.3 Hz, 1H), 7.27-7.26 (m, 2H), 7.15 (t, J=8.9 Hz, 1H), 5.47 (s, 2H), 5.19 (d, J=2.8 Hz, 1H), 4.95 (d, J=2.3 Hz, 1H), 4.84-4.74 (m, 2H), 4.41 (s, 2H), 4.34 (q, J=7.3 Hz, 2H), 4.12 (d, J=10.6 Hz, 1H), 3.96 (dd, J=10.1, 3.4 Hz, 1H), 3.91 (d, J=10.6 Hz, 1H), 3.88 (dd, J=10.6, 3.4 Hz, 1H), 1.28 (t, J=7.5 Hz, 3H). LC/MS calcd. for $C_{27}H_{25}ClFNO_8$ [(M+H)$^+$] 546, obsd. 546.

Example K

Synthesis of 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carbonitrile

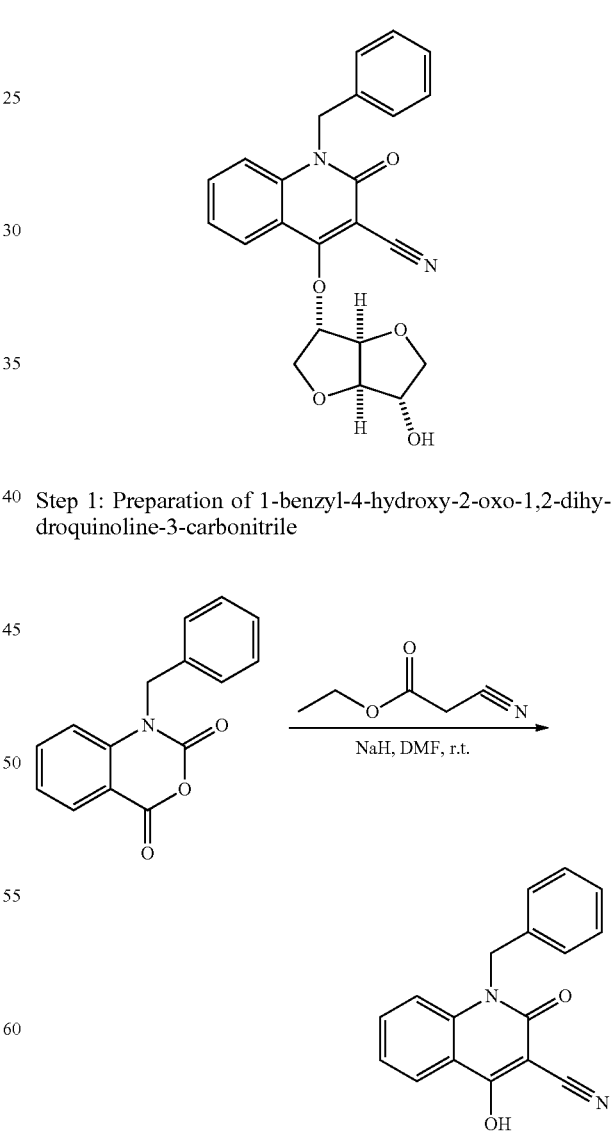

Step 1: Preparation of 1-benzyl-4-hydroxy-2-oxo-1,2-dihydroquinoline-3-carbonitrile A 250 mL 2-neck round bottom flask was charged with 1-benzyl isatoic anhydride (5.06 g, 20 mmol) and then DMF (45 mL) was added followed by ethyl cyanoacetate (2.375 g, 2.23 mL, 21 mmol) at room temperature under an argon atmosphere. Then, the solid sodium hydride (1.95 g, 80.66 mmol, 60% dispersion in oil) was added in two portions at 20 minute periods at room temperature. The resulting pale yellow foam suspension was stirred for 36 h at room temperature under an argon atmosphere by which time it turned into a very thick black viscous suspension.

Then, it was slowly quenched by adding a few drops of water though it was not exothermic. The suspension was poured into 500 mL of water while stirring with spatula. The neutral organic impurities were extracted into EA (2×250 mL) and the basic aqueous layer was neutralized with 1.0N HCl while the resulting white suspension was extracted into EA (2×150 mL). A lot of solid precipitated in the combined extracts which were cooled with ice. The resulting off-white solids were collected by filtration and washed with hexanes. After air drying, 3.75 g (68%) of 1-benzyl-4-hydroxy-2-oxo-1,2-dihydroquinoline-3-carbonitrile was isolated as an off-white solid. LC/MS calcd. for $C_{17}H_{12}N_2O_2$ $[(M-H)^-]$ 275, obsd. 275.

Step 2: Preparation of 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carbonitrile To a solution of triphenylphosphine (1.97 g, 7.5 mmol) in THF (50 mL) in a 250 mL 3-neck RB flask was added di-isopropylazodicarboxylate (1.52 g, 1.48 mL, 7.5 mmol) at 0-5° C. (ice+water) for 3-5 minutes under an argon atmosphere. The resulting light yellow suspension was stirred for 10-15 minutes at this temperature. Then, a solution of 1-benzyl-4-hydroxy-2-oxo-1,2-dihydroquinoline-3-carbonitrile (1.38 g, 5.0 mmol) in THF (50 mL, heated to dissolve) was added drop-wise for 5 minutes. After 2 minutes, the cooling bath was removed to allow the reaction mixture to warm to room temperature and it was stirred for 10-15 minutes.

Then, a solution of isosorbide (877 mg, 6.0 mmol) in THF (30 mL) was slowly added followed by the neat DIPEA (970 mg, 1.31 mL, 7.5 mmol) at room temperature. After 3 h stirring, it gave a light yellow solution which was stirred for 15 h at which time TLC analysis of the reaction mixture indicated the absence of any new spot.

Then, it was heated to 65° C. and stirred for 15 h while TLC analysis indicated the presence of lot of starting material, but a new spot appeared and it was continued for another 36 h. Then, the reaction mixture was cooled to room temperature and the solvent was removed under vacuum. The crude residue was purified using an ISCO (330 g) column chromatography to afford 1.61 g (80%) of 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carbonitrile as a white solid. $^1$H-NMR (DMSO-d6): δ 8.01 (d, J=7.3 Hz, 1H), 7.69 (t, J=7.3 Hz, 1H), 7.43 (d, J=8.4 Hz, 1H), 7.35-7.3 (m, 3H), 7.26-7.24 (m, 3H), 5.74 (d, J=2.3 Hz, 1H), 5.51 (s, 2H), 5.35 (d, J=3.9 Hz, 1H), 4.92 (d, J=3.9 Hz, 1H), 4.65 (d, J=3.4 Hz, 1H), 4.26 (d, J=10.6 Hz, 1H), 4.18 (br, s, 1H), 3.93 (dd, J=10.6, 2.8 Hz, 1H), 3.81 (dd, J=9.0, 3.4 Hz, 1H), 3.76 (d, J=9.0 Hz, 1H). LC/MS calcd. for $C_{23}H_{20}N_2O_5$ $[(M+H)^+]$ 405, obsd. 405.

Example L

Preparation of [(3S,3aR,6S,6aR)-3-[(1-benzyl-3-cyano-2-oxo-4-quinolyl)oxy]-2,3,3a,5,6,6a-hexahydrofuro[3,2-b]furan-6-yl] acetate

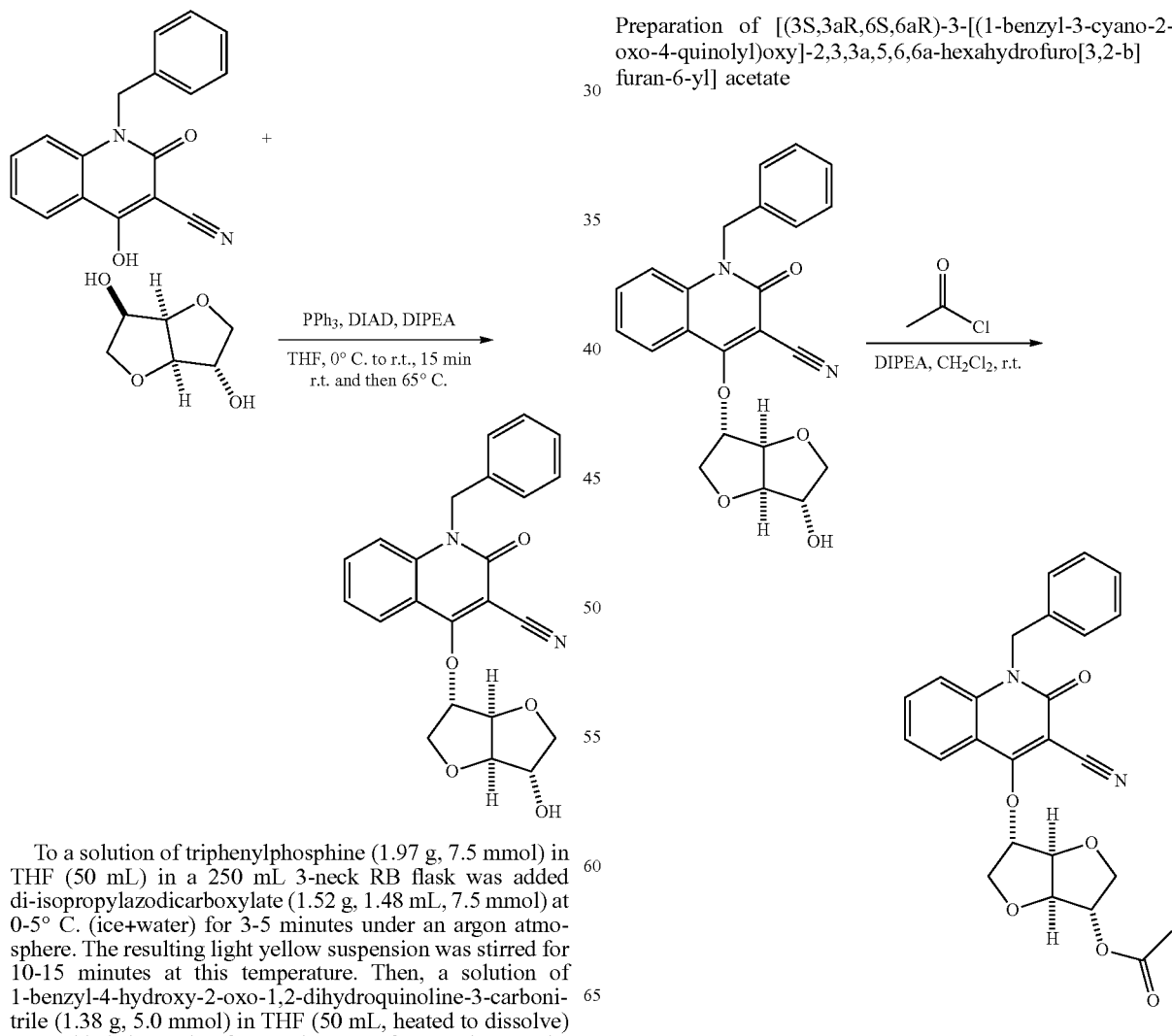

To a colorless solution of 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carbonitrile (101 mg, 0.25 mmol) in dichloromethane (5 mL) in a 25 mL 2-neck RB flask were added first 2-acetyl chloride (39 mg, 35 uL, 0.5 mmol) followed by the neat DIPEA (129 mg, 174 uL, 1.0 mmol) at 0-5° C. under an argon atmosphere. After addition of DIPEA, the reaction mixture turned into a light brown solution that warmed to room temperature without removing the cooling bath and was stirred for 48 h by which time TLC (1:1, Hex:EA) analysis of the reaction mixture indicated the appearance of a new less polar spot.

Then, it was diluted with water and the organic compound was extracted into dichloromethane (2×50 mL). The combined organic extracts were washed with brine solution and dried over anhydrous MgSO$_4$. Filtration and concentration resulted in crude residue that was purified using an ISCO (120 g) column chromatography to isolate 106 mg (95%) of [(3S,3aR,6S,6aR)-3-[(1-benzyl-3-cyano-2-oxo-4-quinolyl)oxy]-2,3,3a,5,6,6a-hexahydrofuro[3,2-b]furan-6-yl] acetate as an amorphous white solid. $^1$H-NMR (CDCl$_3$): δ 8.01 (d, J=7.3 Hz, 1H), 7.68 (t, J=7.3 Hz, 1H), 7.38-7.2 (m, 7H), 5.98 (d, J=2.3 Hz, 1H), 5.5 (s, 2H), 5.22 (d, J=3.9 Hz, 1H), 4.95 (d, J=3.9 Hz, 1H), 4.86 (d, J=3.4 Hz, 1H), 4.41 (d, J=10.6 Hz, 1H), 4.18 (dd, J=10.6, 2.8 Hz, 1H), 4.0-3.97 (m, 2H), 2.05 (s, 3H). LC/MS calcd. for C$_{25}$H$_{22}$N$_2$O$_6$ [(M+H)$^+$] 447, obsd. 447.

Example M

Preparation of [(3S,3aR,6S,6aR)-3-[(1-benzyl-3-cyano-2-oxo-4-quinolyl)oxy]-2,3,3a,5,6,6a-hexahydrofuro[3,2-b]furan-6-yl] 2-chloroacetate

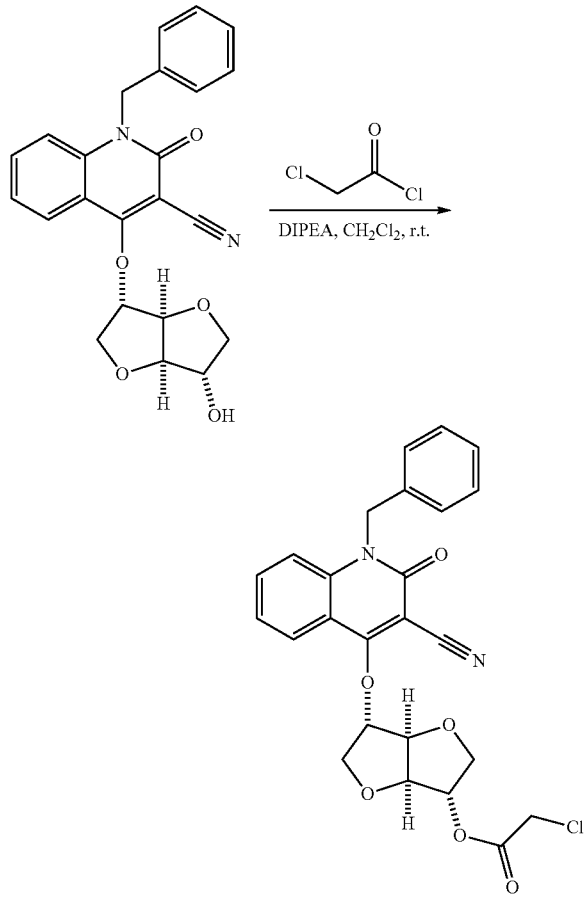

To a colorless solution of 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carbonitrile (101 mg, 0.25 mmol) in dichloromethane (5 mL) in a 25 mL 2-neck RB flask were added first 2-chloroacetyl chloride (112 mg, 80 uL, 1.0 mmol) then followed by the neat DIPEA (388 mg, 522 uL, 3.0 mmol) at room temperature under an argon atmosphere. After addition of DIPEA, the reaction mixture turned into a dark brown solution. The resulting solution was stirred for 48 h by which time TLC (1:1, Hex:EA) analysis of the reaction mixture indicated the appearance of a new less polar spot.

Then, it was diluted with water and the organic compound was extracted into dichloromethane (2×50 mL). The combined organic extracts were washed with brine solution and dried over anhydrous MgSO$_4$. Filtration and concentration gave the crude residue which was purified by using an ISCO (120 g) column chromatography to isolate 105 mg (87%) of [(3S,3aR,6S,6aR)-3-[(1-benzyl-3-cyano-2-oxo-4-quinolyl)oxy]-2,3,3a,5,6,6a-hexahydrofuro[3,2-b]furan-6-yl] 2-chloroacetate as an amorphous off-white solid. $^1$H-NMR (CDCl$_3$): δ 8.05 (d, J=7.4 Hz, 1H), 7.52 (t, J=7.4 Hz, 1H), 7.38-7.1 (m, 7H), 5.91 (d, J=2.3 Hz, 1H), 5.5 (s, 2H), 5.35 (d, J=3.9 Hz, 1H), 5.0 (d, J=3.9 Hz, 1H), 4.94 (d, J=3.4 Hz, 1H), 4.42 (d, J=10.6 Hz, 1H), 4.21-4.0 (m, 5H). LC/MS calcd. for C$_{25}$H$_{21}$ClN$_2$O$_6$ [(M+H)$^+$] 481, obsd. 481.

Example N

Synthesis of 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carbonitrile

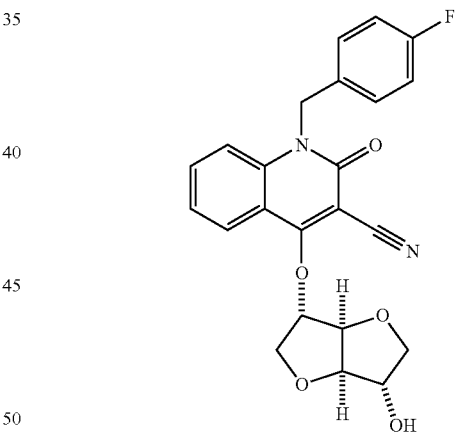

Step 1: Preparation of 1-[(4-fluorophenyl)methyl]-4-hydroxy-2-oxo-1,2-dihydroquinoline-3-carbonitrile

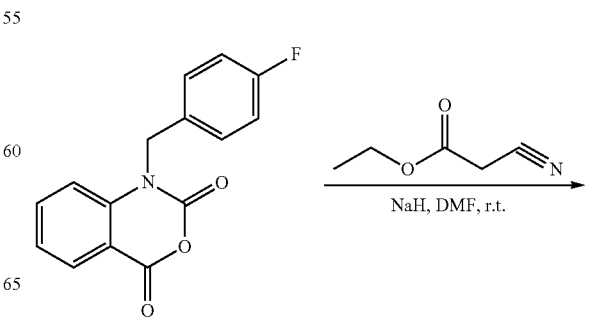

61
-continued

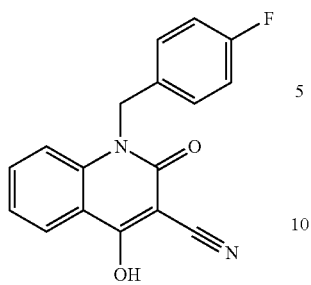

A 250 mL 3-neck round bottom flask was charged with 1-[(4-fluorophenyl)methyl]-isatoic anhydride (11.77 g, 40 mmol) and DMF (90 mL) was added followed by ethyl cyanoacetate (4.75 g, 4.47 mL, 42 mmol) under an argon atmosphere. Then, the solid sodium hydride (3.87 g, 161.32 mmol, 60% dispersion in oil) was added in two portions at 20 minute intervals at room temperature. During the addition, a lot of gas evolved resulting in a light yellowish foam suspension. It was stirred for 48 h at room temperature under an argon atmosphere by which time it became a black suspension.

Then, it was slowly quenched by the addition of a few drops of water and it was slightly exothermic. The suspension was poured into 500 mL of water while stirred with the spatula. The neutral organic compounds were extracted into EA (250 mL) and the basic aqueous layer was neutralized with 1.0N HCl though the resulting white precipitate was not a filterable solid. Then, it was diluted with ~30% EA in hexane solution and as a result some nice solids were formed after being stirred with a spatula. The solids were collected by filtration and washed with water and hexanes. After air drying, 11.7 g (99%) of 1-[(4-fluorophenyl)methyl]-4-hydroxy-2-oxo-1,2-dihydroquinoline-3-carbonitrile was isolated as a light brown solids. LC/MS calcd. for $C_{17}H_{11}FN_2O_2[(M-H)^-]$ 293, obsd. 293.

Step 2: Preparation of 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carbonitrile

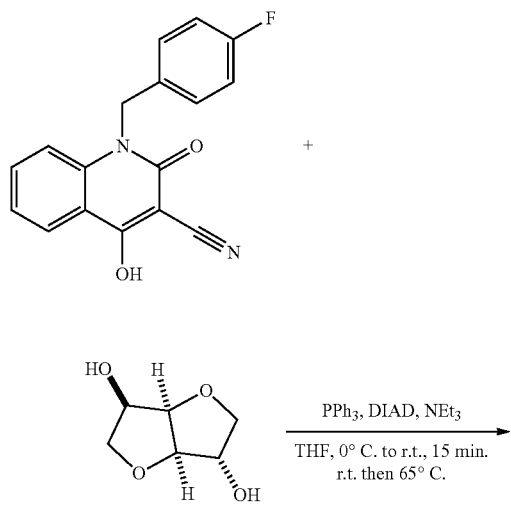

62
-continued

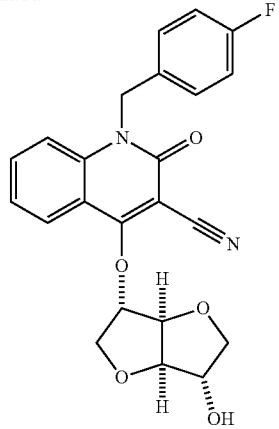 [SMILES: N#Cc1c(O[C@H]2CO[C@H]3[C@@H]2OC[C@@H]3O)c2ccccc2n(Cc2ccc(F)cc2)c1=O]

To a solution of triphenylphosphine (3.93 g, 15 mmol) in THF (100 mL) in a 500 mL 3-neck RB flask was added di-isopropylazodicarboxylate (3.03 g, 2.95 mL, 15 mmol) at 0-5° C. (ice+water) for 10 minutes under an argon atmosphere. Within 2 minutes, a light yellow suspension was formed which was stirred for 10 minutes at this temperature. Then, a solution of 1-[(4-fluorophenyl)methyl]-4-hydroxy-2-oxo-1,2-dihydroquinoline-3-carbonitrile (2.94 g, 10 mmol) in THF (100 mL, dissolved at r.t.) was added drop-wise for 15 minutes. After 2 minutes, the cooling bath was removed to allow the reaction mixture to warm to room temperature and stirred for 10-15 minutes.

Then, a solution of isosorbide (1.75 g, 12 mmol) in THF (60 mL) was slowly added followed by the neat triethylamine (1.52 g, 2.09 mL, 15 mmol) at room temperature. The resulting light brown solution was stirred for 3 h at room temperature. Then, it was heated to 65° C. and stirred for 36 h by which time TLC analysis indicated the presence of a new polar spot. The reaction mixture was cooled to room temperature and the solvent was removed under vacuum. Then, the crude residue was purified using an ISCO (220 g) column chromatography to afford 4.1 g of a white solid. However, TLC analysis of this solid indicated the presence of some triphenylphosphine oxide impurity. A 1.5 g of this material was crystallized from hot acetonitrile to obtain 906 mg. The remaining material was crystallized from hot EA and hexanes to obtain 2.1 g with a total of 3.06 g (72%) of pure 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carbonitrile as a white solid. $^1$H-NMR (DMSO-d6): δ 8.01 (d, J=7.3 Hz, 1H), 7.70 (t, J=7.8 Hz, 1H), 7.46 (d, J=8.4 Hz, 1H), 7.35-7.3 (m, 3H), 7.14 (t, J=8.4 Hz, 2H), 5.74 (d, J=2.3 Hz, 1H), 5.49 (s, 2H), 5.35 (d, J=3.4 Hz, 1H), 4.92 (d, J=3.9 Hz, 1H), 4.65 (d, J=3.4 Hz, 1H), 4.26 (d, J=11.2 Hz, 1H), 4.19 (br, s, 1H), 3.93 (dd, J=10.6, 3.4 Hz, 1H), 3.81 (dd, J=9.0, 3.4 Hz, 1H), 3.76 (d, J=9.0 Hz, 1H). LC/MS calcd. for $C_{23}H_{19}FN_2O_5$ [(M+H)$^+$] 423, obsd. 423.

Example O

Preparation of [(3S,3aR,6S,6aR)-3-[[3-cyano-1-[(4-fluorophenyl)methyl]-2-oxo-4-quinolyl]oxy]-2,3,3a,5,6,6a-hexahydrofuro[3,2-b]furan-6-yl] acetate

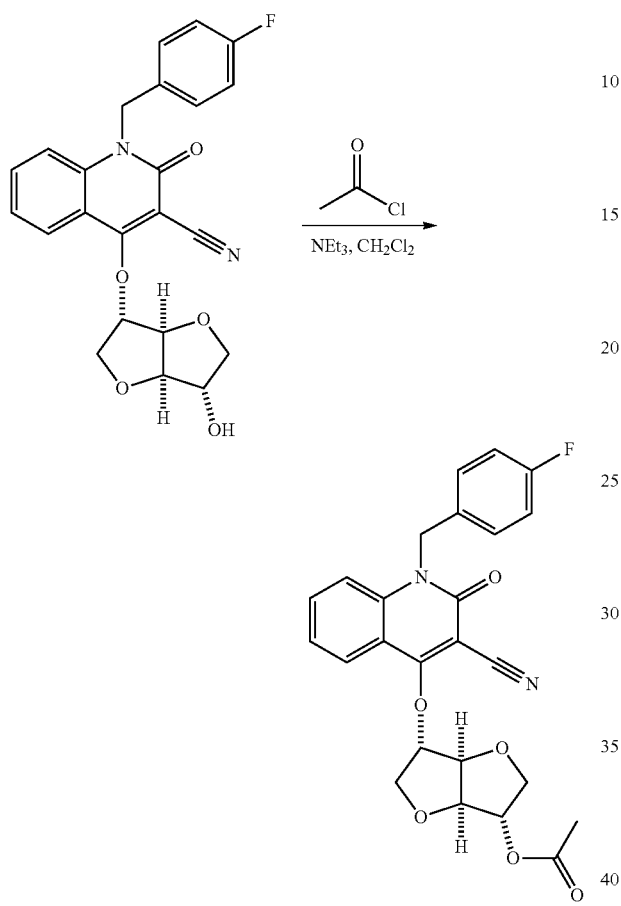

To a light brown solution of 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carbonitrile (1.05 g, 2.48 mmol) in dichloromethane (50 mL) in a 100 mL 2-neck RB flask were added first acetyl chloride (243 mg, 220 uL, 3.1 mmol) followed by the neat NEt$_3$ (627 mg, 864 uL, 6.2 mmol) at 0-5° C. under an argon atmosphere. There was no color change so the light brown solution was allowed to warm to room temperature without removing the cooling bath and stirred for 15 h by which time TLC (1:1, Hex:EA) analysis of the reaction mixture indicated the appearance of a new less polar spot.

Then, it was diluted with water and the organic compound was extracted into dichloromethane. The combined organic extracts were washed with brine solution and dried over anhydrous MgSO$_4$. Filtration and concentration gave the crude residue which was purified by using an ISCO (220 g) column chromatography to isolate 657 mg (57%) of [(3S,3aR,6S,6aR)-3-[[3-cyano-1-[(4-fluorophenyl)methyl]-2-oxo-4-quinolyl]oxy]-2,3,3a,5,6,6a-hexahydrofuro[3,2-b]furan-6-yl] acetate as an amorphous white solid. $^1$H-NMR (DMSO-d6): δ 8.05 (d, J=7.8 Hz, 1H), 7.70 (t, J=8.4 Hz, 1H), 7.46 (d, J=8.4 Hz, 1H), 7.34-7.3 (m, 3H), 7.14 (t, J=9.0 Hz, 2H), 5.80 (d, J=2.3 Hz, 1H), 5.49 (s, 2H), 5.13 (d, J=3.4 Hz, 1H), 4.99 (d, J=3.9 Hz, 1H), 4.86 (d, J=3.9 Hz, 1H), 4.32 (d, J=10.6 Hz, 1H), 4.03-3.98 (m, 2H), 3.92 (d, J=10.1 Hz, 1H), 2.05 (s, 3H). LC/MS calcd. for C$_{25}$H$_{21}$FN$_2$O$_6$ [(M+H)$^+$] 465, obsd. 465.

Example P

Preparation of [(3S,3aR,6S,6aR)-3-[[3-cyano-1-[(4-fluorophenyl)methyl]-2-oxo-4-quinolyl]oxy]-2,3,3a,5,6,6a-hexahydrofuro[3,2-b]furan-6-yl] benzoate

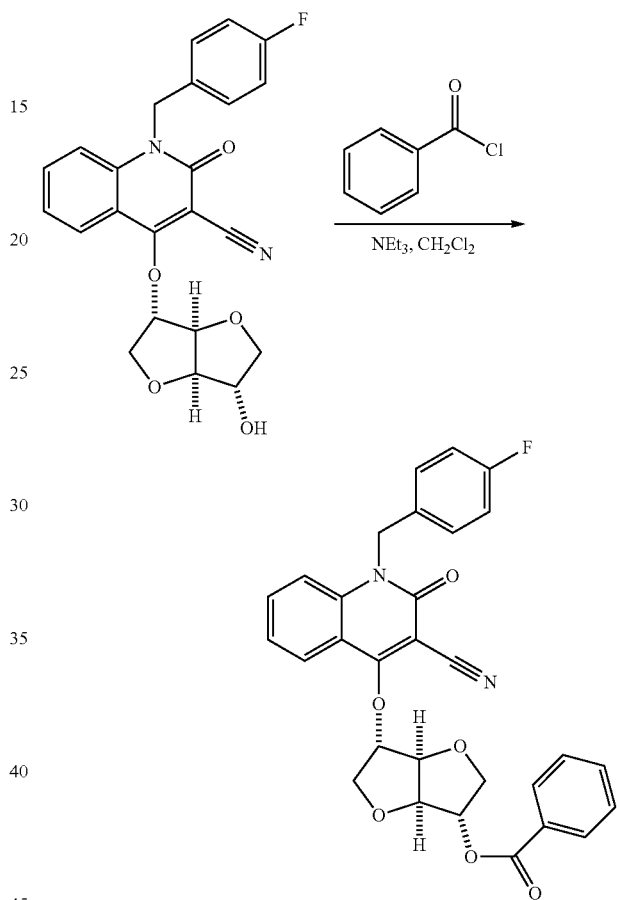

To a colorless solution of 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carbonitrile (435 mg, 1.03 mmol) in dichloromethane (15 mL) in a 50 mL 2-neck RB flask were added first benzoyl chloride (174 mg, 144 uL, 1.24 mmol) followed by the neat triethylamine (253 mg, 348 uL, 2.5 mmol) at 0-5° C. under an argon atmosphere. The resulting light yellow solution was allowed to warm to room temperature without removing the cooling bath and stirred for 15 h by which time TLC (1:1, Hex:EA) analysis of the reaction mixture indicated the appearance of a new less polar spot.

Then, it was diluted with water and the organic compound was extracted into dichloromethane (2×50 mL). The combined organic extracts were washed with brine solution and dried over anhydrous MgSO$_4$. Filtration and concentration yielded a crude residue that was purified using an ISCO (80 g) column chromatography to obtain 360 mg (66%) of [(3S,3aR,6S,6aR)-3-[[3-cyano-1-[(4-fluorophenyl)methyl]-2-oxo-4-quinolyl]oxy]-2,3,3a,5,6,6a-hexahydrofuro[3,2-b]furan-6-yl] benzoate as an amorphous white solid. $^1$H-NMR (DMSO-d6): δ 8.0-7.93 (m, 3H), 7.68 (t, J=7.6 Hz, 1H), 7.62 (t, J=8.4 Hz, 1H), 7.55-7.4 (m, 3H), 7.42 (d, J=7.5 Hz, 1H), 7.33-7.20 (m, 4H), 5.76 (d, J=2.3 Hz, 1H), 5.49 (s, 2H), 5.12 (d, J=3.9 Hz, 1H), 4.96 (d, J=3.9 Hz, 1H), 4.85 (d, J=3.4 Hz, 1H), 4.32 (d, J=10.6 Hz, 1H), 4.03-3.98 (m, 2H), 3.92 (d, J=10.1 Hz, 1H). LC/MS calcd. for $C_{30}H_{23}FN_2O_6$ [(M+H)$^+$] 527, obsd. 527.

Example Q

Preparation of [(3S,3aR,6S,6aR)-3-[[3-cyano-1-[(4-fluorophenyl)methyl]-2-oxo-4-quinolyl]oxy]-2,3,3a,5,6,6a-hexahydrofuro[3,2-b]furan-6-yl] 2-chloroacetate

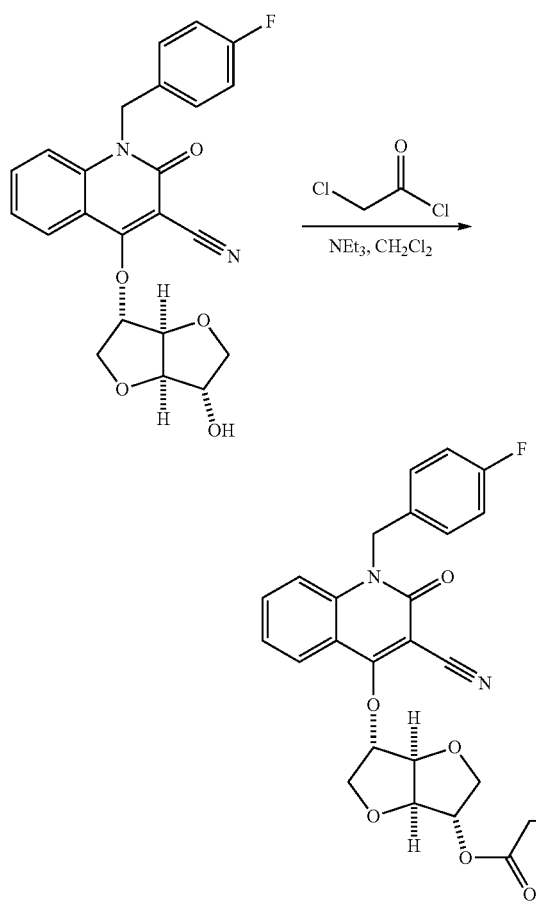

To a light brown solution of 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carbonitrile (1.05 g, 2.48 mmol) in dichloromethane (50 mL) in a 100 mL 2-neck RB flask were added first 2-chloroacetyl chloride (351 mg, 248 uL, 3.1 mmol) followed by the neat NEt$_3$ (627 mg, 864 uL, 6.2 mmol) at 0-5° C. under an argon atmosphere. There was no color change and the light brown solution was allowed to warm to room temperature itself and stirred for 15 h at room temperature by which time TLC (1:1, Hex:EA) analysis of the reaction mixture indicated the appearance of a new less polar spot.

Then, it was diluted with water and the organic compound was extracted into dichloromethane (2×50 mL). The combined organic extracts were washed with brine solution and dried over anhydrous MgSO$_4$. Filtration and concentration produced a crude residue that was purified using an ISCO (220 g) column chromatography to afford 390 mg (32%) of [(3S,3aR,6S,6aR)-3-[[3-cyano-1-[(4-fluorophenyl)methyl]-2-oxo-4-quinolyl]oxy]-2,3,3a,5,6,6a-hexahydrofuro[3,2-b]furan-6-yl] 2-chloroacetate as an amorphous white solid. $^1$H-NMR (DMSO-d6): δ 8.03 (d, J=6.7 Hz, 1H), 7.72 (t, J=7.3 Hz, 1H), 7.46 (d, J=7.8 Hz, 1H), 7.35-7.31 (m, 3H), 7.15 (t, J=7.8 Hz, 2H), 5.81 (d, J=2.3 Hz, 1H), 5.49 (s, 2H), 5.23 (d, J=3.9 Hz, 1H), 4.98 (d, J=3.9 Hz, 1H), 4.90 (d, J=3.4 Hz, 1H), 4.44 (s, 2H), 4.33 (d, J=10.6 Hz, 1H), 4.03-34.01 (m, 2H), 3.97 (d, J=10.6, 1H). LC/MS calcd. for $C_{25}H_{20}ClFN_2O_6$ [(M+H)$^+$] 499, obsd. 499.

Example R

Preparation of 4-[4-[[(3S,3aR,6S,6aR)-3-hydroxy-2,3,3a,5,6,6a-hexahydrofuro[3,2-b]furan-6-yl]oxy]-3-chloro-anilino]-1-benzyl-2-oxo-1,2-dihydroquinoline-3-carbonitrile

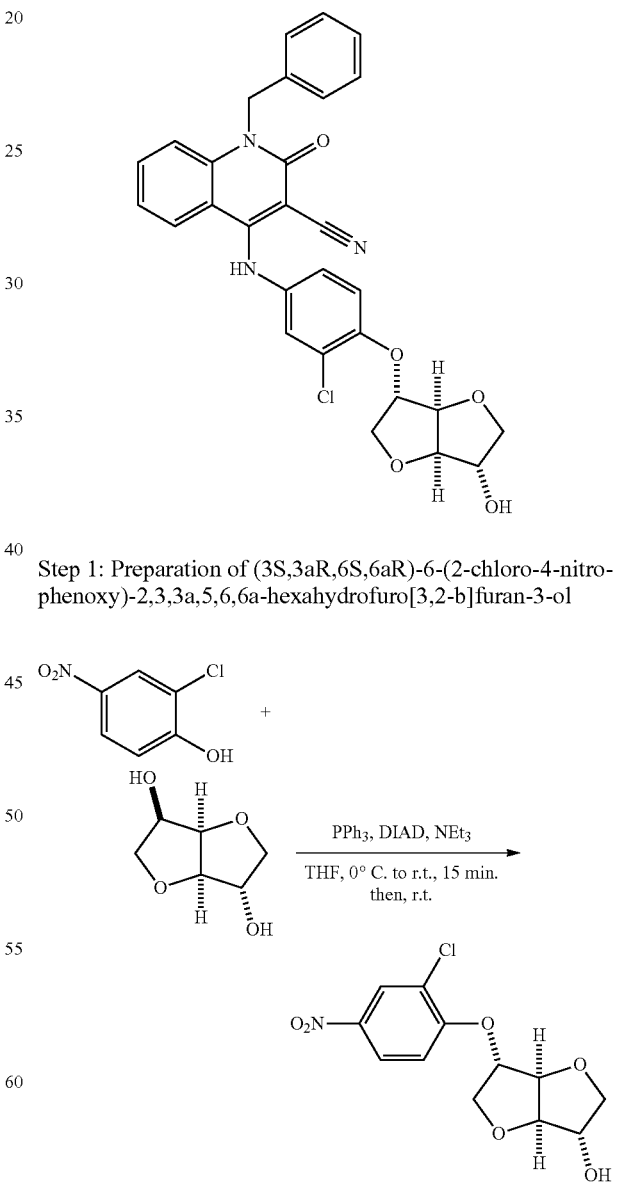

Step 1: Preparation of (3S,3aR,6S,6aR)-6-(2-chloro-4-nitrophenoxy)-2,3,3a,5,6,6a-hexahydrofuro[3,2-b]furan-3-ol To a solution of triphenylphosphine (7.87 g, 30 mmol) in THF (200 mL) in a 500 mL 3-neck RB flask was added di-isopropylazodicarboxylate (6.06 g, 5.9 mL, 30 mmol) at 0-5° C. (ice+water) for 10 minutes under an argon atmosphere. The resulting light yellow suspension was stirred for 10-15 minutes at this temperature. Then, a clear solution of 2-chloro-4-nitrophenol (3.47 g, 20 mmol) in THF (100 mL) was added drop-wise over 10-15 minutes. After 2 minutes, the cooling bath was removed to allow the reaction mixture to warm to room temperature where it was stirred for 10-15 minutes.

Then, a solution of isosorbide (3.51 g, 24 mmol) in THF (60 mL) was slowly added followed by the neat DIPEA (3.87 g, 5.22 mL, 30 mmol) at room temperature. It produced a light yellow color solution after the addition of isosorbide solution. Then, the resulting light yellow solution was stirred for 36 h and the cloudy reaction mixture was heated to 65° C. and stirred for 4 h by which time TLC (1:1, Hex:EA) analysis of the reaction mixture indicated the appearance of a new spot.

Then, the reaction mixture was cooled to room temperature and the solvent was removed under vacuum. The crude residue was dissolved in a minimum amount of EA at hot condition and then diluted with hexanes. The resulting solution was stored in the freezer over the weekend. The resulting off-white solids were collected by filtration and washed with hexanes. After air drying, 20.05 g of solid was isolated as a mixture of the desired product and triphenylphosphine oxide based on the TLC. This solid was dissolved in acetonitrile (~30 mL) in hot conditions and then stored in the freezer. The resulting triphenylphosphine oxide solids were collected by filtration and the filtration was removed under vacuum which mostly contained the desired product.

Then, the residue was again dissolved in minimum EA at hot condition and diluted with hexanes and the clear solution was stored in the freezer. The remaining triphenylphosphine oxide precipitated which was removed by filtration under vacuum to obtain 5.56 g (92%) of (3S,3aR,6S,6aR)-6-(2-chloro-4-nitro-phenoxy)-2,3,3a,5,6,6a-hexahydrofuro[3,2-b]furan-3-ol as a light brown paste. $^{1}$H-NMR (DMSO-d6): δ 8.34 (d, J=2.3 Hz, 1H), 8.23 (dd, J=8.4, 2.8 Hz, 1H), 7.46 (d, J=8.4 Hz, 1H), 5.30 (d, J=3.9 Hz, 1H), 5.16 (d, 2.8 Hz, 1H), 4.64 (d, J=3.9 Hz, 1H), 4.48 (d, J=3.9 Hz, 1H), 4.15 (br, s, 1H), 4.02 (dd, J=10.1, 3.9 Hz, 1H), 3.93 (d, J=10.1 Hz, 1H), 3.81 (dd, J=8.4, 3.4 Hz, 1H), 3.74 (d, J=9.0 Hz, 1H). LC/MS calcd. for $C_{12}H_{12}ClNO_6$ [(M–H)$^{-}$]300, obsd. 300.

Step 2: Preparation of (3S,3aR,6S,6aR)-6-(4-amino-2-chloro-phenoxy)-2,3,3a,5,6,6a-hexahydrofuro[3,2-b]furan-3-ol To a solution of (3S,3aR,6S,6aR)-6-(2-chloro-4-nitro-phenoxy)-2,3,3a,5,6,6a-hexahydrofuro[3,2-b]furan-3-ol (3.01 g, 10 mmol) in methanol (100 mL) in a 250 mL single neck RB flask were added an excess zinc dust (6.54 g, 100 mmol) and ammonium chloride (8.02 g, 150 mmol) followed by water (50 mL) at room temperature under an argon atmosphere. It was exothermic reaction after the addition of water. Then, the reaction mixture was heated twice with a heat gun.

Then, it was stirred for another 3 h at room temperature by which time TLC analysis of the mixture indicated the absence of starting material. During this period the initial yellow color solution changed into a colorless solution. The excess zinc dust was filtered off using the cotton plug and the solid cake was washed with methanol and water. The filtrate was removed under vacuum and the aqueous layer was saturated with the solid NaCl. Then, the organic compound was extracted with EA (3×100 mL) and the combined extracts were washed with brine solution. The organic layer was dried over anhydrous MgSO$_4$, filtration and concentration gave the crude 2.7 g (100%) of (3S,3aR,6S,6aR)-6-(4-amino-2-chloro-phenoxy)-2,3,3a,5,6,6a-hexahydrofuro[3,2-b]furan-3-ol as a light brown solid which was used directly in the next step without purification. LC/MS calcd. for $C_{12}H_{14}ClNO_4$ [(M–H)$^{-}$] 270, obsd. 270.

Step 3: Preparation of 1-benzyl-4-chloro-2-oxo-1,2-dihydroquinoline-3-carbonitrile

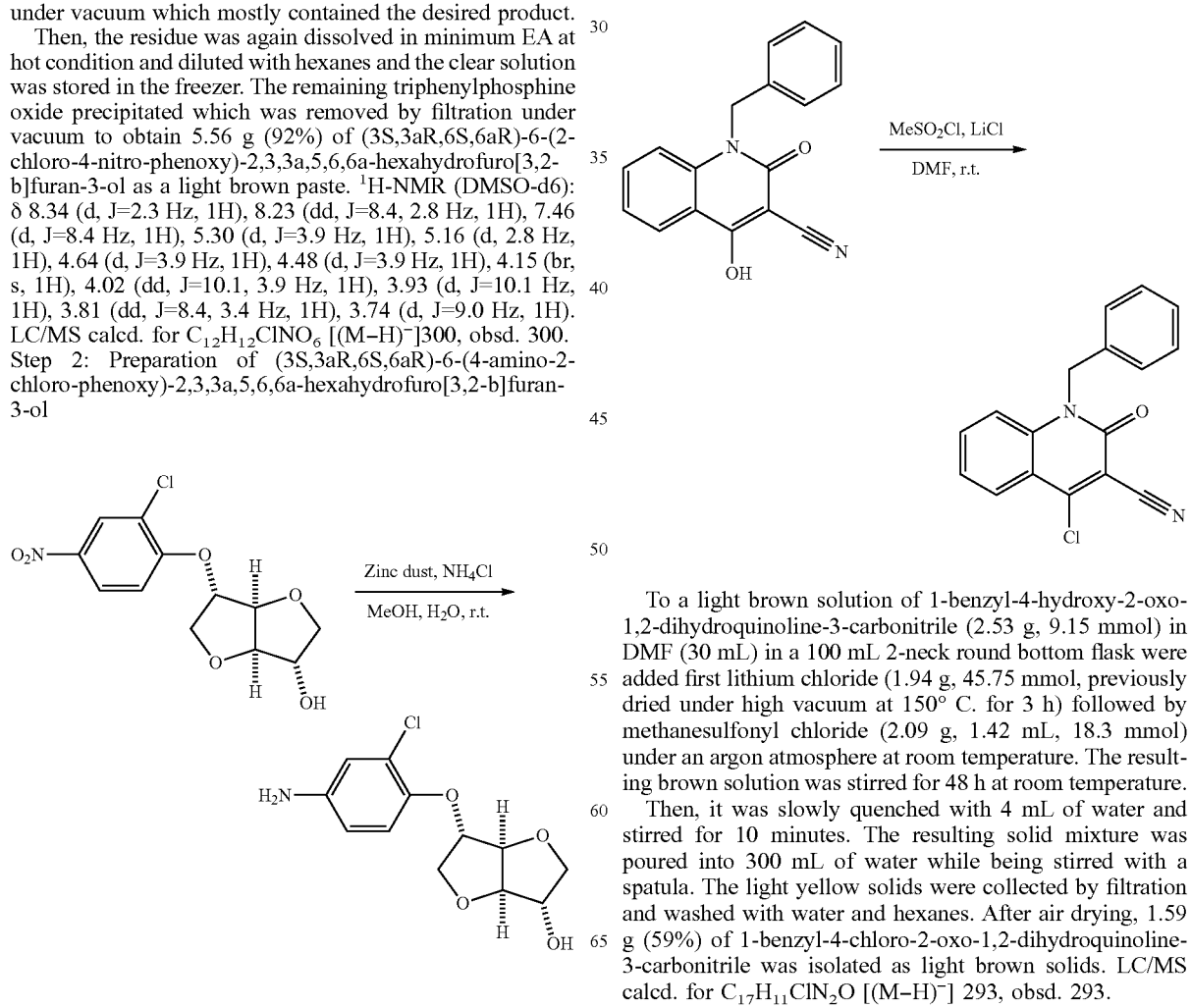

To a light brown solution of 1-benzyl-4-hydroxy-2-oxo-1,2-dihydroquinoline-3-carbonitrile (2.53 g, 9.15 mmol) in DMF (30 mL) in a 100 mL 2-neck round bottom flask were added first lithium chloride (1.94 g, 45.75 mmol, previously dried under high vacuum at 150° C. for 3 h) followed by methanesulfonyl chloride (2.09 g, 1.42 mL, 18.3 mmol) under an argon atmosphere at room temperature. The resulting brown solution was stirred for 48 h at room temperature.

Then, it was slowly quenched with 4 mL of water and stirred for 10 minutes. The resulting solid mixture was poured into 300 mL of water while being stirred with a spatula. The light yellow solids were collected by filtration and washed with water and hexanes. After air drying, 1.59 g (59%) of 1-benzyl-4-chloro-2-oxo-1,2-dihydroquinoline-3-carbonitrile was isolated as light brown solids. LC/MS calcd. for $C_{17}H_{11}ClN_2O$ [(M–H)$^{-}$] 293, obsd. 293.

Step 4: Preparation of 4-[4-[[(3S,3aR,6S,6aR)-3-hydroxy-2,3,3a,5,6,6a-hexahydrofuro[3,2-b]furan-6-yl]oxy]-3-chloro-anilino]-1-benzyl-2-oxo-1,2-dihydroquinoline-3-carbonitrile

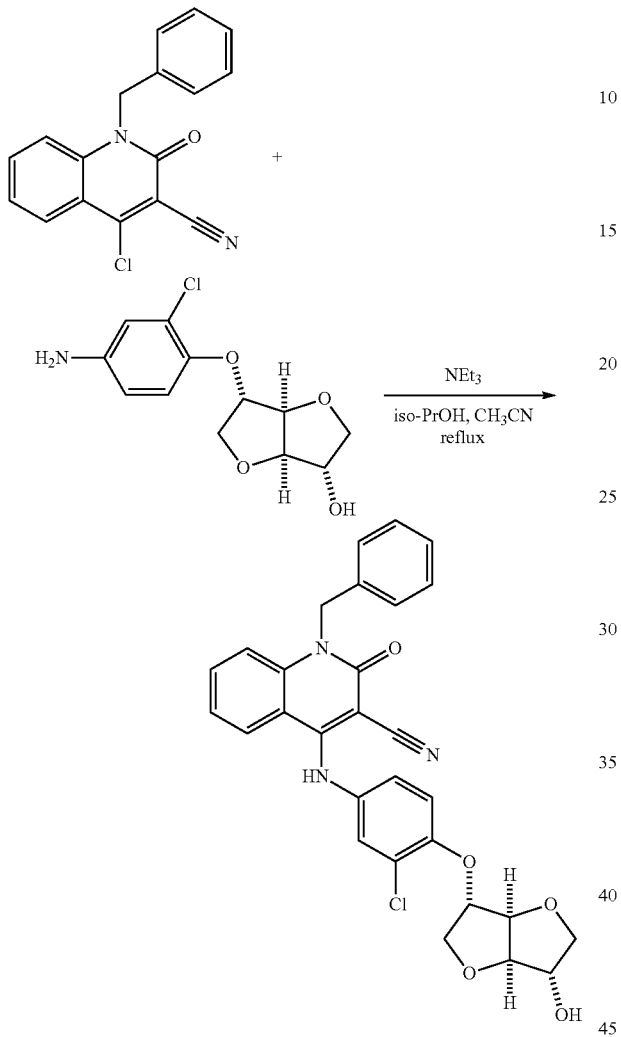

To a mixture of 1-benzyl-4-chloro-2-oxo-1,2-dihydroquinoline-3-carbonitrile (1.47 g, 5.0 mmol) and (3S,3aR,6S,6aR)-6-(4-amino-2-chloro-phenoxy)-2,3,3a,5,6,6a-hexahydrofuro[3,2-b]furan-3-ol (1.66 g, 6.1 mmol) in a 50 mL single neck RB flask was added iso-propanol (35 mL) at room temperature under an argon atmosphere. Then, an excess of triethylamine (1.01 g, 1.39 mL, 10.0 mmol) was added and the resulting light brown suspension was heated to reflux (110° C., bath temperature) for 5 h.

Then, 35 mL of acetonitrile was added to dissolve all solids and the resulting brown solution was refluxed for another 4 days by which time TLC (EA) analysis indicated the presence of a new polar spot. The reaction mixture was cooled to room temperature and the solvent was removed under vacuum. The crude residue was diluted with water and saturated ammonium chloride solution. Then, the organic compound was extracted into ethyl acetate (3×70 mL). The combined extracts were washed with brine solution and the organic layer was dried, filtered and the solvent was removed under vacuum. The crude residue was dissolved in acetonitrile at hot condition and then it was diluted with ethyl acetate. As a result, lot of yellow solids were precipitated which was diluted with hexanes. The suspension was stored in the freezer for 15 h and the solids were collected by filtration and dried to afford 1.31 g (50%) of 4-[4-[[(3S,3aR,6S,6aR)-3-hydroxy-2,3,3a,5,6,6a-hexahydrofuro[3,2-b]furan-6-yl]oxy]-3-chloro-anilino]-1-benzyl-2-oxo-1,2-dihydroquinoline-3-carbonitrile as a light yellow solid. $^1$H-NMR (DMSO-d6): δ 9.78 (s, 1H), 8.32 (d, J=7.3 Hz, 1H), 7.63 (t, J=7.8 Hz, 1H), 7.52 (d, J=2.3 Hz, 1H), 7.38-7.22 (m, 9H), 5.47 (s, 2H), 5.27 (d, J=3.4 Hz, 1H), 4.98 (d, J=2.8 Hz, 1H), 4.60 (d, J=3.4 Hz, 1H), 4.49 (d, J=3.4 Hz, 1H), 4.14 (br, s, 1H), 3.96 (dd, J=10.1, 3.4 Hz, 1H), 3.91 (d, J=10.1 Hz, 1H), 3.80 (dd, J=9.0, 3.4 Hz, 1H), 3.72 (d, J=9.0 Hz, 1H). LC/MS calcd. for $C_{29}H_{24}ClN_3O_5$ [(M+H)$^+$] 530, obsd. 530.

Example S

Synthesis of ethyl 4-[4-[[(3S,3aR,6S,6aR)-3-hydroxy-2,3,3a,5,6,6a-hexahydrofuro[3,2-b]furan-6-yl]oxy]-3-chloro-anilino]-1-benzyl-2-oxo-1,2-dihydroquinoline-3-carboxylate

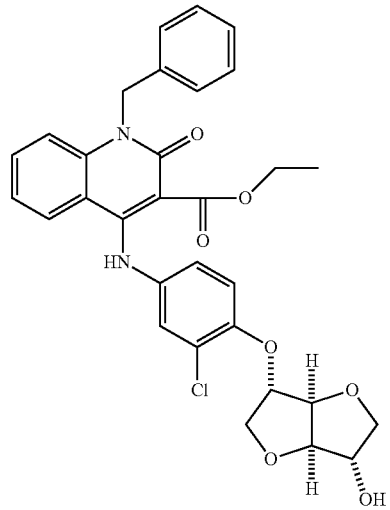 [SMILES: CCOC(=O)c1c(Nc2ccc(O[C@H]3CO[C@H]4[C@@H]3OC[C@@H]4O)c(Cl)c2)c2ccccc2n(Cc2ccccc2)c1=O]

Step 1: Preparation of ethyl 1-benzyl-4-chloro-2-oxo-quinoline-3-carboxylate

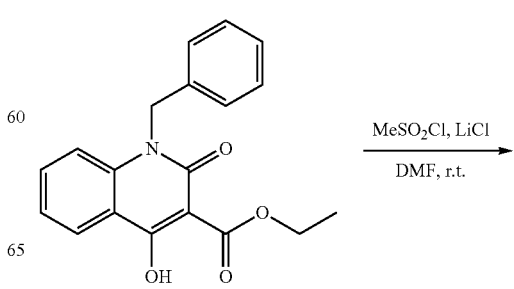

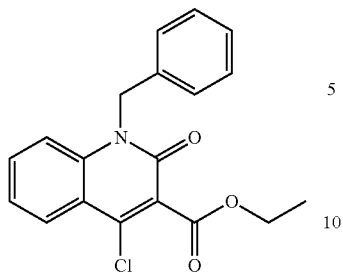

To a light brown solution of ethyl 1-benzyl-4-hydroxy-2-oxo-quinoline-3-carboxylate (2.8 g, 8.6 mmol) in DMF (30 mL) in a 100 mL 2-neck round bottom flask were added first lithium chloride (1.91 g, 45.0 mmol, previously dried under high vacuum at 150° C. for 3 h) followed by methanesulfonyl chloride (2.06 g, 1.39 mL, 18.0 mmol) under an argon atmosphere at room temperature. Within 5 minutes, it gave a clear light brown solution which was stirred for 48 h at room temperature.

Then, it was slowly quenched with 10 mL of water and stirred for 10 minutes. The resulting brown solution was poured into 300 mL of water while being stirred with a spatula. The resulting off-white solids were collected by filtration and washed with water and hexanes. After air drying, 1.91 g (65%) of ethyl 1-benzyl-4-chloro-2-oxo-quinoline-3-carboxylate was isolated as light brown solids. LC/MS calcd. for $C_{19}H_{16}ClNO_3$ [(M−H)−] 340, obsd. 340.

Step 2: Preparation of ethyl 4-[4-[[(3S,3aR,6S,6aR)-3-hydroxy-2,3,3a,5,6,6a-hexahydrofuro[3,2-b]furan-6-yl]oxy]-3-chloro-anilino]-1-benzyl-2-oxo-1,2-dihydroquinoline-3-carboxylate

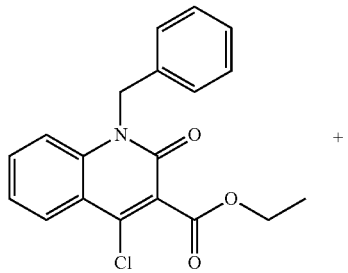

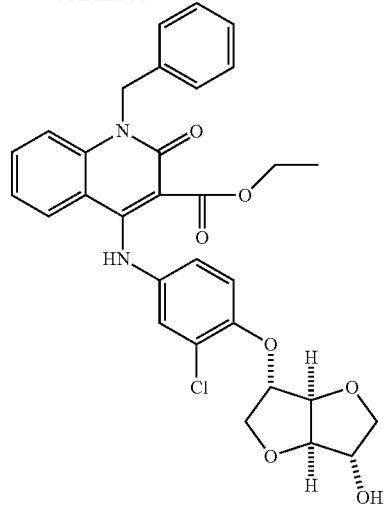

To a mixture of ethyl 1-benzyl-4-chloro-2-oxo-quinoline-3-carboxylate (390 mg, 1.1 mmol) and (3S,3aR,6S,6aR)-6-(4-amino-2-chloro-phenoxy)-2,3,3a,5,6,6a-hexahydrofuro[3,2-b]furan-3-ol (269 mg, 0.9 mmol) in a 50 mL 2-neck RB flask was added iso-propanol (5 mL) at room temperature under an argon atmosphere. Then, an excess of triethylamine (304 mg, 418 uL, 3.0 mmol) was added and the resulting light brown suspension was heated to reflux (110° C., bath temperature) for 6 h. Then, 5 mL of acetonitrile was added and the resulting solution was refluxed for another 48 h by which time TLC (EA) analysis of the mixture indicated the presence of a new polar spot.

The reaction mixture was cooled to room temperature and water was added. The resulting white precipitate was extracted into EA (2×50 mL) and the combined organic extracts were washed with brine solution and dried over anhydrous magnesium sulfate. Filtration and concentration gave the crude paste which was purified using an ISCO (120 g) column chromatography to afford 116 mg (20%) of ethyl 4-[4-[[(3S,3aR,6S,6aR)-3-hydroxy-2,3,3a,5,6,6a-hexahydrofuro[3,2-b]furan-6-yl]oxy]-3-chloro-anilino]-1-benzyl-2-oxo-1,2-dihydroquinoline-3-carboxylate as a light yellow solid. $^1$H-NMR (DMSO-d6): δ 8.85 (s, 1H), 8.29 (d, J=6.7 Hz, 1H), 7.64-7.53 (m, 4H), 7.37 (d, 9.0 Hz, 1H), 7.32-7.2 (m, 5H), 7.07 (dd, J=9.0, 2.8 Hz, 1H), 5.47 (s, 2H), 5.26 (d, J=3.4 Hz, 1H), 4.9 (d, J=3.4 Hz, 1H), 4.56 (d, J=3.4 Hz, 1H), 4.48 (d, J=3.4 Hz, 1H), 4.13 (s, 1H), 3.97 (dd, J=10.8, 4.2 Hz, 1H), 3.89 (d, J=9.6 Hz, 1H), 3.79 (dd, J=9.6, 3.0 Hz, 1H), 3.77 (d, J=9.6 Hz, 1H), 3.56 (q, J=6.6 Hz, 2H), 1.08 (t, J=7.8, 3H). LC/MS calcd. for $C_{31}H_{29}ClN_2O_7$ [(M+H)+] 577, obsd. 577.

Example T

Preparation of (3S,3aR,6S,6aR)-6-[2-chloro-4-[(6,7-dimethoxyquinazolin-4-yl)amino]phenoxy]-2,3,3a,5,6,6a-hexahydrofuro[3,2-b]furan-3-ol

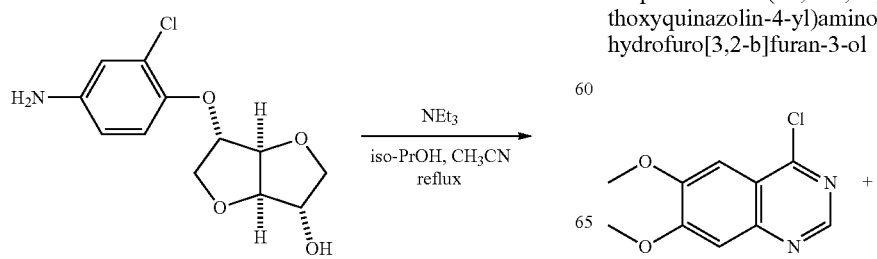

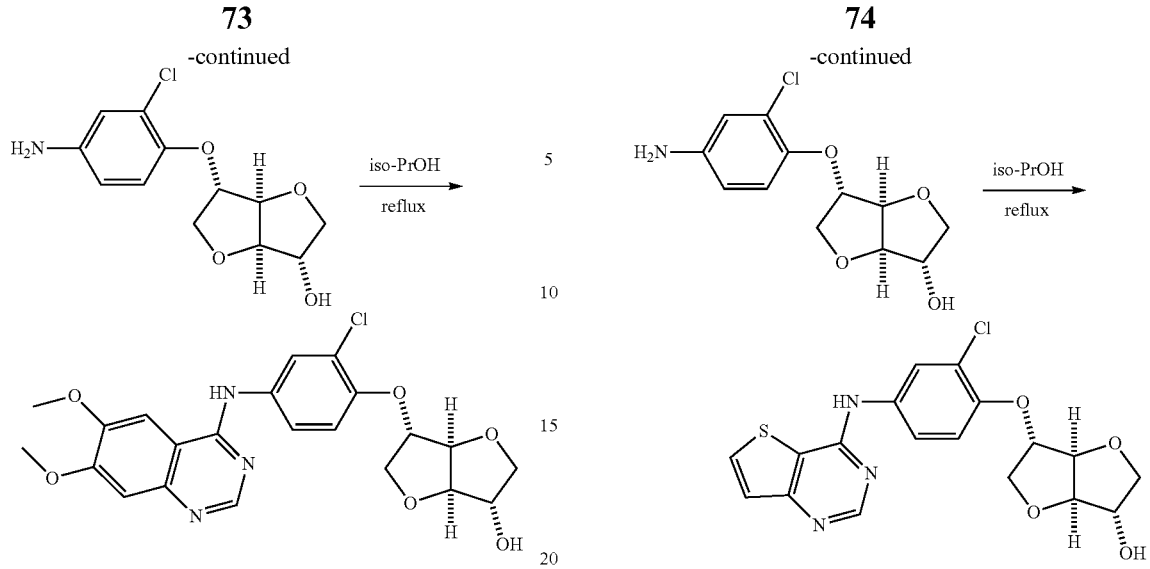

To a mixture of 4-chloro-6,7-dimethoxyquinazoline (449 mg, 2.0 mmol) and (3S,3aR,6S,6aR)-6-(4-amino-2-chlorophenoxy)-2,3,3a,5,6,6a-hexahydrofuro[3,2-b]furan-3-ol (680 mg, 2.5 mmol) in a 100 mL single neck RB flask was added iso-propanol (40 mL) at room temperature under an argon atmosphere. The resulting suspension was heated to reflux (110° C., bath temperature) which produced a clear solution when the temperature reached to 100° C. After 10 minutes reflux, a light yellow precipitate started to form which became a thick suspension during 4 h reflux.

Then, the reaction mixture was diluted with EA at reflux and it was cooled to room temperature. The resulting light yellow solids were collected by filtration and washed with EA. After air drying, 498 mg (54%) of (3S,3aR,6S,6aR)-6-[2-chloro-4-[(6,7-dimethoxyquinazolin-4-yl)amino]phenoxy]-2,3,3a,5,6,6a-hexahydrofuro[3,2-b]furan-3-ol was isolated as a light yellow solid. TLC analysis (EA) of the solids indicated the presence of some impurity. Then, the solids were dissolved in acetonitrile with a small amount of methanol in hot conditions and then stored in the freezer for 1 h. The resulting solids were collected by filtration and washed with acetonitrile. After air drying, 190 mg of pure (3S,3aR,6S,6aR)-6-[2-chloro-4-[(6,7-dimethoxyquinazolin-4-yl)amino]phenoxy]-2,3,3a, 5,6,6a-hexahydrofuro[3,2-b]furan-3-ol was isolated as a light yellow solid. $^1$H-NMR (DMSO-d6): δ 11.55 (s, 1H), 8.84 (s, 1H), 8.32 (s, 1H), 8.0 (d, J=2.2 Hz, 1H), 7.88 (dd, J=8.4, 2.2 Hz, 1H), 7.44-7.43 (m, 2H), 4.98 (d, J=3.4 Hz, 1H), 4.61 (d, J=3.9 Hz, 1H), 4.49 (d, 3.4 Hz, 1H), 4.15 (d, J=2.8 Hz, 1H), 4.02 (s, 3H), 4.01 (br, s, 1H), 3.99 (s, 3H), 3.98 (d, J=5.6 Hz, 1H), 3.91 (d, J=9.5 Hz, 1H), 3.80 (dd, J=8.9, 3.9 Hz, 1H), 3.72 (d, J=8.9 Hz, 1H). LC/MS calcd. for $C_{22}H_{22}ClN_3O_6$ [(M+H)$^+$] 460, obsd. 460.

Example U

Preparation of (3S,3aR,6S,6aR)-6-[2-chloro-4-(thieno[3,2-d]pyrimidin-4-ylamino)phenoxy]-2,3,3a,5,6,6a-hexahydrofuro[3,2-b]furan-3-ol

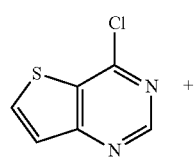

To a mixture of 4-chlorothieno[3,2-d]pyrimidine (171 mg, 1.0 mmol) and (3S,3aR,6S,6aR)-6-(4-amino-2-chlorophenoxy)-2,3,3a,5,6,6a-hexahydrofuro[3,2-b]furan-3-ol (543 mg, 2.0 mmol) in a 50 mL single neck RB flask was added iso-propanol (20 mL) at room temperature under an argon atmosphere. The resulting suspension was heated to reflux (110° C., bath temperature) yielding a clear solution. After 3 h reflux, some light yellow precipitate formed and this mixture was stirred for another 3 h at this temperature. After cooling to 80° C., some EA was added and the reaction suspension was allowed to cool to room temperature.

Then, the solids were collected by filtration and washed with EA. After air drying, 317 mg (78%) of (3S,3aR,6S, 6aR)-6-[2-chloro-4-(thieno[3,2-d]pyrimidin-4-ylamino) phenoxy]-2,3,3a,5,6,6a-hexahydrofuro[3,2-b]furan-3-ol was isolated as a light yellow solid. $^1$H-NMR (DMSO-d6): δ 11.27 (s, 1H), 8.85 (s, 1H), 8.46 (d, J=5.6 Hz, 1H), 7.89 (d, J=2.8 Hz, 1H), 7.63 (d, J=6.2 Hz, 1H), 7.62 (d, J=5.0 Hz, 1H), 7.35 (d, J=8.4 Hz, 1H), 5.3 (d, J=3.4 Hz, 1H), 5.09 (s, 1H), 4.68-4.65 (m, 2H), 4.12-4.0 (m, 5H). LC/MS calcd. for $C_{18}H_{16}ClN_3O_4S$ [(M+H)$^+$] 406, obsd. 406.

Example V

Preparation of (3S,3aR,6S,6aR)-6-[2-chloro-4-[(2-methylsulfanylpyrimidin-4-yl)amino]phenoxy]-2,3,3a,5,6,6a-hexahydrofuro[3,2-b]furan-3-ol

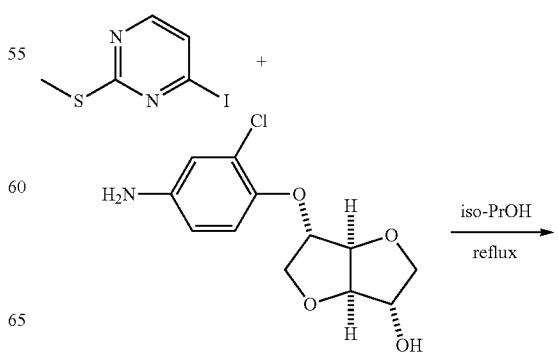

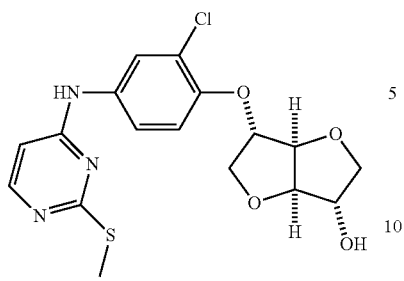

To a mixture of 4-iodo-2-methylthiopyrimidine (504 mg, 2.0 mmol) and (3S,3aR,6S,6aR)-6-(4-amino-2-chloro-phenoxy)-2,3,3a,5,6,6a-hexahydrofuro[3,2-b]furan-3-ol (679 mg, 2.5 mmol) in a 50 mL single neck RB flask was added iso-propanol (30 mL) at room temperature under an argon atmosphere. The resulting suspension was heated to reflux (110° C., bath temperature) which produced a clear solution. After 20 minutes reflux, some light yellow precipitate started to form and it was stirred for another 5 h at this temperature.

Then, it was lowered the temperature to 85° C. and stirred for 15 h. At this time, some EA was added and the reaction suspension was cooled to room temperature. Then, the solids were collected by filtration and washed with EA. After air drying, 522 mg (62%) of (3S,3aR,6S,6aR)-6-[2-chloro-4-[(2-methylsulfanylpyrimidin-4-yl)amino]phenoxy]-2,3,3a,5,6,6a-hexahydrofuro[3,2-b]furan-3-ol was isolated as a light yellow solid. $^1$H-NMR (DMSO-d6): δ 10.55 (s, 1H), 8.16 (d, J=6.2 Hz, 1H), 7.94 (s, 1H), 7.48 (dd, J=8.4, 2.3 Hz, 1H), 7.29 (d, J=8.4 Hz, 1H), 6.58 (d, J=6.2 Hz, 1H), 4.91 (d, J=3.2 Hz, 1H), 4.58 (d, J=3.9 Hz, 1H), 4.46 (d, 3.9 Hz, 1H), 4.13 (d, J=3.4 Hz, 1H), 3.95 (dd, J=10.5, 3.9 Hz, 1H), 3.89 (d, J=9.8 Hz, 1H), 3.78 (dd, J=9.5, 3.4 Hz, 1H), 3.77 (d, J=9.5 Hz, 1H), 2.56 (s, 3H). LC/MS calcd. for $C_{17}H_{18}ClN_3O_4S$ [(M+H)$^+$] 396, obsd. 396.

Example W

Preparation of (3S,3aR,6S,6aR)-6-[4-[[2-[4-[[(3S,3aR,6S,6aR)-3-hydroxy-2,3,3a,5,6,6a-hexahydrofuro[3,2-b]furan-6-yl]oxy]-3-chloro-anilino]pyrimidin-4-yl]amino]-2-chloro-phenoxy]-2,3,3a,5,6,6a-hexahydrofuro[3,2-b]furan-3-ol

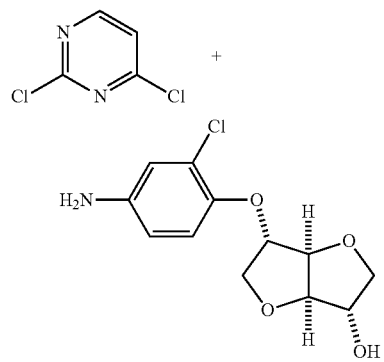

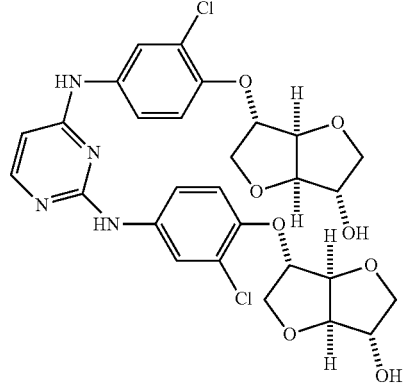

To a solution of (3S,3aR,6S,6aR)-6-(4-amino-2-chloro-phenoxy)-2,3,3a,5,6,6a-hexahydrofuro[3,2-b]furan-3-ol (350 mg, 1.2 mmol) in MeOH (2.0 mL) in a 25 mL sealed tube were added 2,4-dichloropyrimidine (75 mg, 0.5 mmol) and water (2 mL) at room temperature under an argon atmosphere. Then, the rubber septum was replaced with a screw cap and the resulting clear colorless solution was heated to 120° C. (bath temperature). After 3 h at this temperature, it became a cloudy solution which was stirred for another 2 h. Then, it was cooled to room temperature as a result some white paste formed.

Then, it was diluted with water and the resulting white solid was collected by filtration and washed with water and hexanes. After air drying, 230 mg of off-white solid was isolated. TLC analysis of this solid that was dissolved in methanol was indicated the presence of some impurity. Then, the solid was suspended in EA and acetonitrile in hot condition and the suspension was stored in the freezer for overnight. The white solid was collected by filtration and washed with EA. After air drying, 171 mg (55%) of (3S, 3aR,6S,6aR)-6-[4-[[2-[4-[[(3S,3aR,6S,6aR)-3-hydroxy-2,3, 3a,5,6,6a-hexahydrofuro[3,2-b]furan-6-yl]oxy]-3-chloro-anilino]pyrimidin-4-yl]amino]-2-chloro-phenoxy]-2,3,3a,5, 6,6a-hexahydrofuro[3,2-b]furan-3-ol was isolated as a white solid. $^1$H-NMR (DMSO-d6): δ 11.07 (s, 1H), 10.6 (s, 1H), 7.96 (d, J=6.2 Hz, 1H), 7.78 (s, 1H), 7.64 (s, 1H), 7.49 (s, 1H), 7.38 (d, J=7.8 Hz, 1H), 7.27 (d, J=8.6 Hz, 1H), 7.22 (d, J=9.0 Hz, 1H), 6.49 (d, J=5.6 Hz, 1H), 4.9 (s, 1H), 4.89 (s, 1H), 4.58 (d, J=3.2 Hz, 1H), 4.56 (d, J=3.2 Hz, 1H), 4.47-4.46 (m, 2H), 4.13 (s, 2H), 3.96-3.94 (m, 2H), 3.88-3.85 (m, 2H), 3.79-3.77 (m, 2H), 3.71-3.70 (m, 2H), 3.41 (br, s, 2H). LC/MS calcd. for $C_{28}H_{28}Cl_2N_4O_8$ [(M+H)$^+$] 619, obsd. 619.

Example X

Synthesis of [(3S,3aR,6S,6aR)-3-[4-[(6,7-dimethoxyquinazolin-4-yl)amino]phenoxy]-2,3,3a,5,6,6a-hexahydrofuro[3,2-b]furan-6-yl] acetate

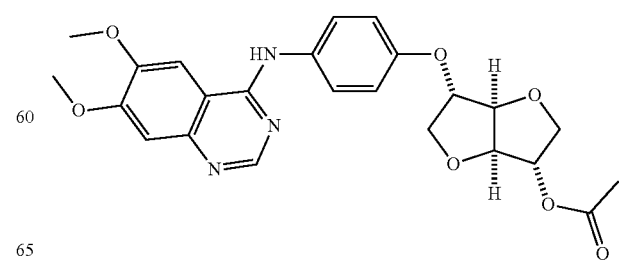

Step 1: Preparation of (3S,3aR,6S,6aR)-6-(4-nitrophenoxy)-2,3,3a,5,6,6a-hexahydrofuro[3,2-b]furan-3-ol

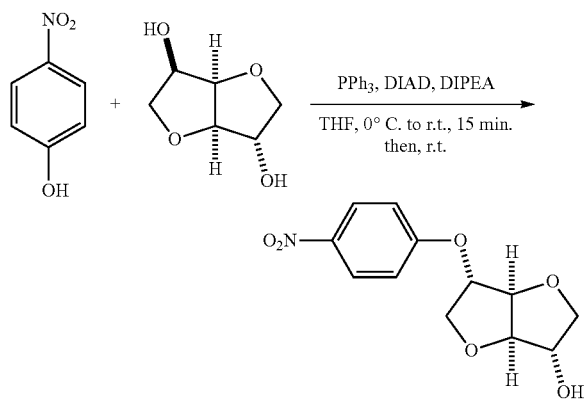

To a solution of triphenylphosphine (1.57 g, 6 mmol) in THF (30 mL) in a 100 mL 2-neck RB flask was added di-isopropylazodicarboxylate (1.21 g, 1.18 mL, 6 mmol) at 0-5° C. (ice+water) for 5 minutes under an argon atmosphere. The resulting light yellow suspension was stirred for 10-15 minutes at this temperature. Then, a clear solution of 4-nitrophenol (556 mg, 4 mmol) in THF (20 mL) was added drop-wise over 5 minutes. After 2 minutes, the cooling bath was removed to allow the reaction mixture to warm to room temperature where it was stirred for 10-15 minutes.

Then, a solution of isosorbide (701 mg, 4.8 mmol) in THF (15 mL) was slowly added followed by the neat DIPEA (775 mg, 1.05 mL, 6 mmol) at room temperature. The resulting light yellow suspension was stirred for 48 h by which time TLC (1:1, Hex:EA) analysis of the reaction mixture indicated the appearance of a new spot. Then, the solvent was removed under vacuum and the crude residue was purified using an ISCO (220 g) column chromatography to afford 1.02 g (96%) of (3S,3aR,6S,6aR)-6-(4-nitrophenoxy)-2,3,3a,5,6,6a-hexahydrofuro[3,2-b]furan-3-ol as a light brown viscous oil. LC/MS calcd. for $C_{12}H_{13}NO_6$ [(M−H)⁻] 266, obsd. 266.

Step 2: Preparation of [(3S,3aR,6S,6aR)-3-(4-nitrophenoxy)-2,3,3a,5,6,6a-hexahydrofuro[3,2-b]furan-6-yl] acetate

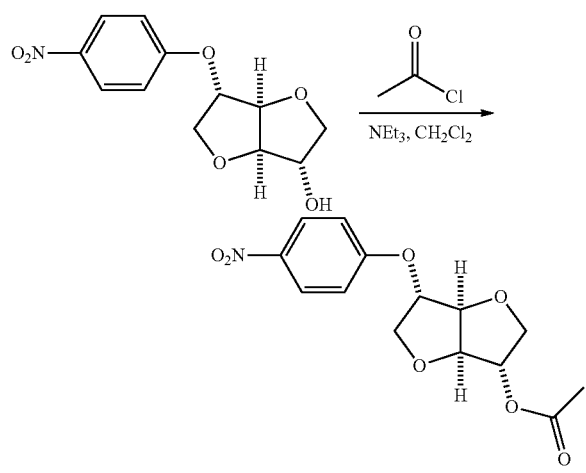

To a colorless solution of (3S,3aR,6S,6aR)-6-(4-nitrophenoxy)-2,3,3a,5,6,6a-hexahydrofuro[3,2-b]furan-3-ol (1.0 g, 3.7 mmol) in dichloromethane (30 mL) in a 100 mL single neck RB flask were added first acetyl chloride (390 mg, 356 uL, 5 mmol) followed by an excess of triethylamine (1.01 g, 1.4 mL, 10 mmol) at 0-5° C. under an argon atmosphere. The resulting light brown solution was allowed to warm to room temperature without removing the cooling bath and then it was stirred for 15 h at room temperature by which time TLC (1:1, Hex:EA) analysis of the reaction mixture indicated the appearance of a new spot. Then, it was diluted with water and the organic compound was extracted into dichloromethane (2×50 mL). The combined organic extracts were washed with brine solution and dried over anhydrous $MgSO_4$. Filtration and concentration provided a crude light brown oil that was purified using an ISCO (120 g) column chromatography to obtain 1.08 g (95%) of [(3S,3aR,6S,6aR)-3-(4-nitrophenoxy)-2,3,3a,5,6,6a-hexahydrofuro[3,2-b]furan-6-yl] acetate as a viscous light yellow oil. LC/MS calcd. for $C_{14}H_{15}NO_7$ [(M−H)⁻] 308, obsd. 308.

Step 3: Preparation of [(3S,3aR,6S,6aR)-3-(4-aminophenoxy)-2,3,3a,5,6,6a-hexahydrofuro[3,2-b]furan-6-yl] acetate

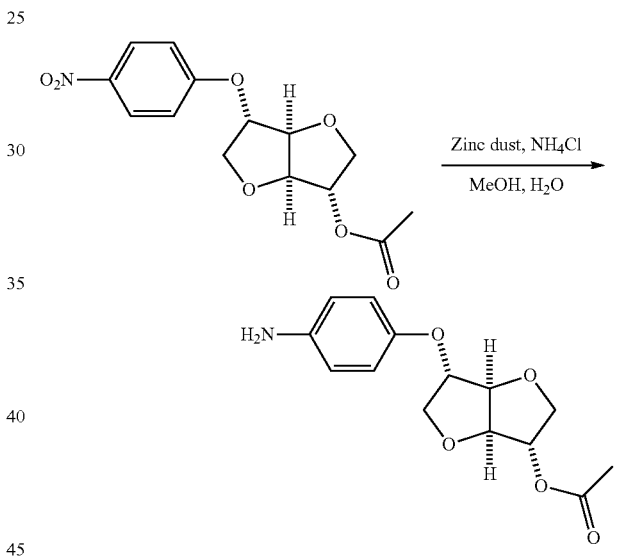

To a mixture of zinc dust (2.28 g, 35 mmol) and ammonium chloride (2.8 g, 52.5 mmol) in a 100 mL 2-neck RB flask was added first a solution of [(3S,3aR,6S,6aR)-3-(4-nitrophenoxy)-2,3,3a,5,6,6a-hexahydrofuro[3,2-b]furan-6-yl] acetate (1.08 g, 3.5 mmol) in methanol (40 mL) followed by water (20 mL) at room temperature under an argon atmosphere. It was exothermic reaction after the addition of methanol solution. Cement colored clusters formed after the addition of water. It was stirred for 1.5 h and then the reaction mixture was heated with a heat gun.

After being stirred for another 1 h at room temperature, TLC analysis of the mixture indicated the absence of starting material. The excess zinc dust was filtered off and the solid cake was washed with methanol and water. The solvent was removed under vacuum and the organic compound was extracted into EA (2×50 mL) while the combined extracts were washed with brine solution. The organic layer was dried over anhydrous $MgSO_4$, filtration and concentration gave the crude oil which was purified using an ISCO (80 g) column chromatography to obtain 685 mg (70%) of [(3S,3aR,6S,6aR)-3-(4-aminophenoxy)-2,3,3a,5,6,6a-hexahydrofuro[3,2-b]furan-6-yl] acetate as a white solid. LC/MS calcd. for $C_{14}H_{17}NO_5$ [(M−H)⁻] 278, obsd. 278.

Step 4: Preparation of [(3S,3aR,6S,6aR)-3-[4-[(6,7-dimethoxyquinazolin-4-yl)amino]phenoxy]-2,3,3a,5,6,6a-hexahydrofuro[3,2-b]furan-6-yl] acetate

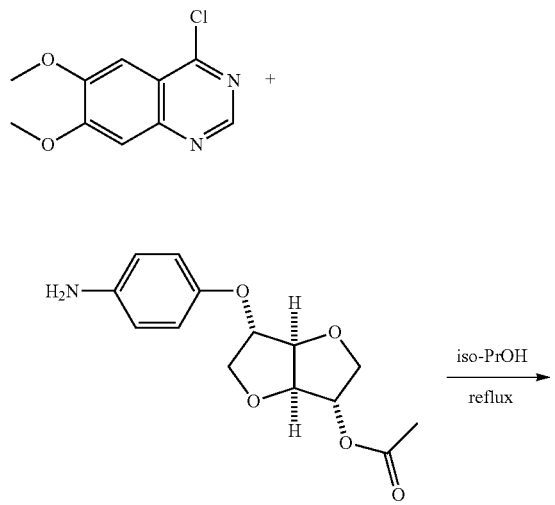

To a mixture of 4-chloro-6,7-dimethoxyquinazoline (112 mg, 0.5 mmol) and [(3S,3aR,6S,6aR)-3-(4-aminophenoxy)-2,3,3a,5,6,6a-hexahydrofuro[3,2-b]furan-6-yl] acetate (251 mg, 0.9 mmol) in a 50 mL 2-neck RB flask was added iso-propanol (10 mL) at room temperature under an argon atmosphere. The resulting suspension was heated to reflux (110° C., bath temperature) which produced a clear solution when the temperature reached ~70° C. Within few minutes some yellow precipitate started to form which was stirred for 8 h at this temperature and 12 h at 85° C.

Then, it was cooled to room temperature and later it was stored in the refrigerator for 5 h. The resulting light yellow solids were collected by filtration and washed with iso-propanol. The solids were dried over weekend to obtain 234 mg (100%) of [(3S,3aR,6S,6aR)-3-[4-[(6,7-dimethoxyquinazolin-4-yl)amino]phenoxy]-2,3,3a,5,6,6a-hexahydrofuro[3,2-b]furan-6-yl]acetate as a light yellow solid. ¹H-NMR (DMSO-d6): δ 11.35 (s, 1H), 8.75 (s, 1H), 8.32 (s, 1H), 7.62-7.6 (m, 2H), 7.34 (s, 1H), 7.09 (d, J=7.8 Hz, 2H), 5.09 (d, J=3.4 Hz, 1H), 4.95 (d, J=3.4 Hz, 1H), 4.66 (d, J=3.9 Hz, 1H), 4.64 (d, J=3.4 Hz, 1H), 4.06 (dd, J=9.5, 3.4 Hz, 1H), 4.01 (s, 3H), 3.99 (s, 3H), 3.97-3.96 (m, 1H), 3.94 (d, J=10.1 Hz, 1H), 3.88 (d, J=10.1 Hz, 1H), 2.03 (s, 3H). LC/MS calcd. for $C_{24}H_{25}N_3O_7$ [(M+H)⁺] 468, obsd. 468.

Example Y

Preparation of [(3S,3aR,6S,6aR)-3-[4-(thieno[3,2-d]pyrimidin-4-ylamino)phenoxy]-2,3,3a,5,6,6a-hexahydrofuro[3,2-b]furan-6-yl] acetate

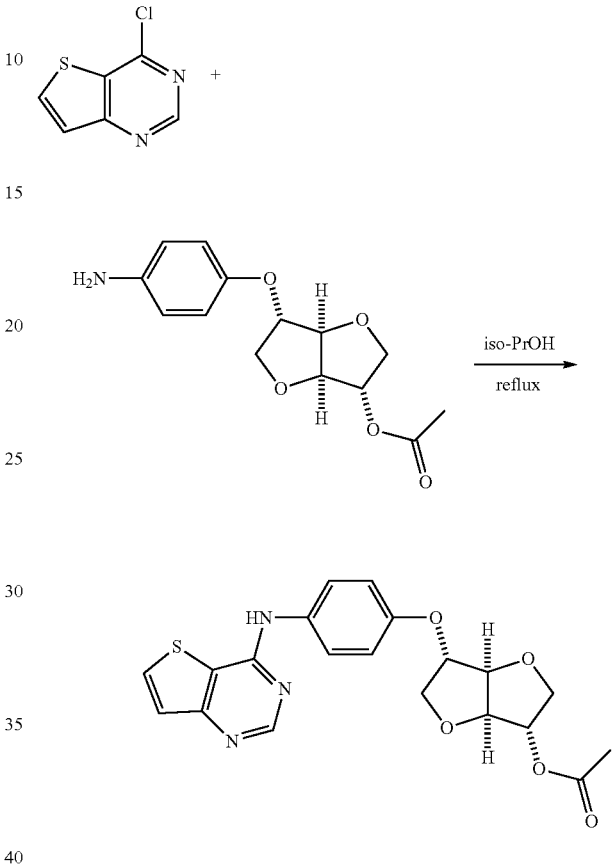

To a mixture of 4-chlorothieno[3,2-d]pyrimidine (85 mg, 0.5 mmol) and [(3S,3aR,6S,6aR)-3-(4-aminophenoxy)-2,3,3a,5,6,6a-hexahydrofuro[3,2-b]furan-6-yl] acetate (149 mg, 0.53 mmol) in a single neck 50 mL RB flask was added iso-propanol (5 mL) at room temperature under an argon atmosphere. The resulting suspension was heated to reflux (110° C., bath temperature) which produced a clear solution at ~60° C. After refluxing for 1 h, some yellow precipitate formed and that was stirred for 4 h. It was cooled to room temperature and the suspension was stored in the refrigerator for 15 h.

The resulting light yellow solids were collected by filtration and washed with EA. The solids were dried over weekend to afford 202 mg (98%) of [(3S,3aR,6S,6aR)-3-[4-(thieno[3,2-d]pyrimidin-4-ylamino)phenoxy]-2,3,3a,5,6,6a-hexahydrofuro[3,2-b]furan-6-yl] acetate as a light yellow solid. ¹H-NMR (DMSO-d6): δ 11.28 (s, 1H), 8.86 (s, 1H), 8.47 (d, J=5.0 Hz, 1H), 7.58-7.55 (m, 3H), 7.09 (d, J=8.4 Hz, 2H), 5.09 (d, J=3.4 Hz, 1H), 4.96 (d, J=2.8 Hz, 1H), 4.66-4.64 (m, 2H), 4.06 (dd, J=9.5, 3.9 Hz, 1H), 3.99 (dd, J=10.1, 3.9 Hz, 1H), 3.92 (d, J=10.2 Hz, 1H), 3.88 (d, J=10.1 Hz, 1H), 2.03 (s, 3H). LC/MS calcd. for $C_{20}H_{19}N_3O_5S$ [(M+H)⁺] 414, obsd. 414.

Example Z

Synthesis of N-[4-[[(3S,3aR,6S,6aR)-3-benzyloxy-2,3,3a,5,6,6a-hexahydrofuro[3,2-b]furan-6-yl]oxy]phenyl]-6,7-dimethoxy-quinazolin-4-amine

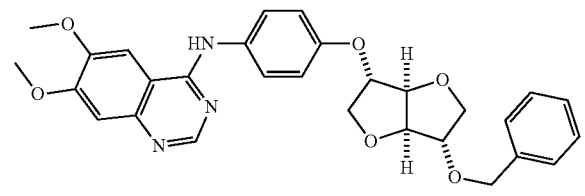 [SMILES: COc1cc2ncnc(Nc3ccc(O[C@H]4CO[C@H]5[C@@H]4OC[C@@H]5OCc4ccccc4)cc3)c2cc1OC]

Step 1: Preparation of (3S,3aR,6S,6aR)-3-benzyloxy-6-(4-nitrophenoxy)-2,3,3a,5,6,6a-hexahydrofuro[3,2-b]furan

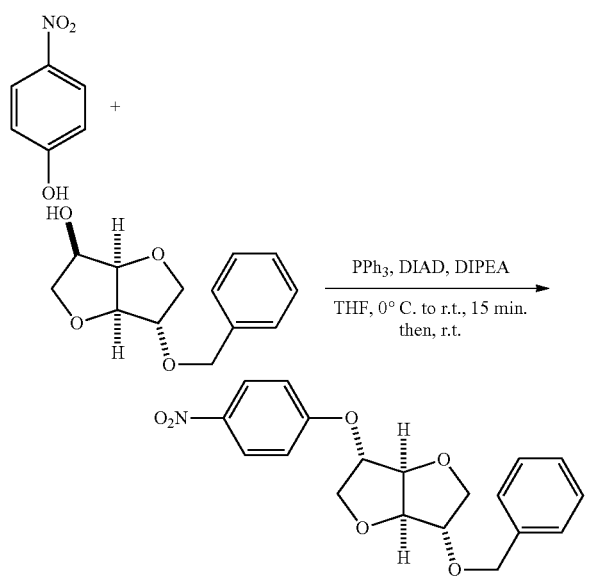

To a solution of triphenylphosphine (1.96 g, 7.5 mmol) in THF (50 mL) in a 250 mL 2-neck RB flask was added di-isopropylazodicarboxylate (1.52 g, 1.48 mL, 7.5 mmol) at 0-5° C. (ice+water) for 5 minutes under an argon atmosphere. The resulting light yellow suspension was stirred for 10-15 minutes at this temperature. Then, a clear solution of 4-nitrophenol (695 mg, 5 mmol) in THF (40 mL) was added drop-wise over 5 minutes. After 2 minutes, the cooling bath was removed to allow the reaction mixture to warm to room temperature where it was stirred for 10-15 minutes.

Then, a solution of isosorbide 2-benzyl ether (1.42 g, 6 mmol) (prepared following the literature procedure, Carbohydrate Research 1994, 261, 255-266) in THF (36 mL) was slowly added followed by the neat triethylamine (759 mg, 1.05 mL, 7.5 mmol) at room temperature. The resulting light yellow suspension was stirred for 48 h by which time TLC (1:1, Hex:EA) analysis of the reaction mixture indicated the appearance of a new spot. Then, the solvent was removed under vacuum and the crude residue was purified using an ISCO (330 g) column chromatography to afford 1.7 g (98%) of (3S,3aR,6S,6aR)-3-benzyloxy-6-(4-nitrophenoxy)-2,3,3a,5,6,6a-hexahydrofuro[3,2-b]furan as a light brown viscous oil. LC/MS calcd. for $C_{19}H_{19}NO_6$ [(M−H)$^-$] 356, obsd. 356.

Step 2: Preparation of 4-[[(3S,3aR,6S,6aR)-3-benzyloxy-2,3,3a,5,6,6a-hexahydrofuro[3,2-b]furan-6-yl]oxy]aniline

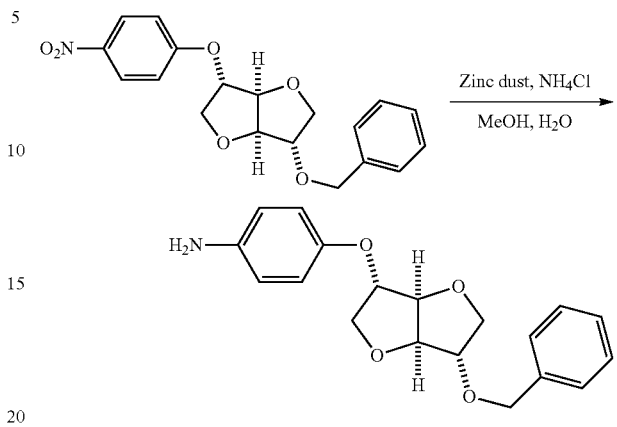

To a mixture of zinc dust (3.3 g, 50 mmol) and ammonium chloride (4.1 g, 75 mmol) in a 250 mL single neck RB flask was added first a solution of (3S,3aR,6S,6aR)-3-benzyloxy-6-(4-nitrophenoxy)-2,3,3a,5,6,6a-hexahydrofuro[3,2-b]furan (1.7 g, 4.75 mmol) in methanol (50 mL) followed by water (25 mL) at room temperature under an argon atmosphere. It was exothermic reaction after the addition of methanol solution. Cement colored clusters formed after the addition of water. It was stirred for 2 h and then the reaction mixture was heated with a heat gun.

After being stirred for another 1 h at room temperature, TLC analysis of the mixture indicated the absence of starting material. The excess zinc dust was filtered off and the solid cake was washed with methanol and water. The solvent was removed under vacuum and the organic compound was extracted into EA (2×50 mL) while the combined extracts were washed with brine solution. The organic layer was dried over anhydrous MgSO$_4$, filtration and concentration gave the crude oil which was purified using an ISCO (120 g) column chromatography to obtain 1.3 g (79%) of 4-[[(3S,3aR,6S,6aR)-3-benzyloxy-2,3,3a,5,6,6a-hexahydrofuro[3,2-b]furan-6-yl]oxy]aniline as a light brown oil. LC/MS calcd. for $C_{19}H_{21}NO_4$ [(M−H)$^-$] 326, obsd. 326.

Step 3: Preparation of N-[4-[[(3S,3aR,6S,6aR)-3-benzyloxy-2,3,3a,5,6,6a-hexahydrofuro[3,2-b]furan-6-yl]oxy]phenyl]-6,7-dimethoxy-quinazolin-4-amine

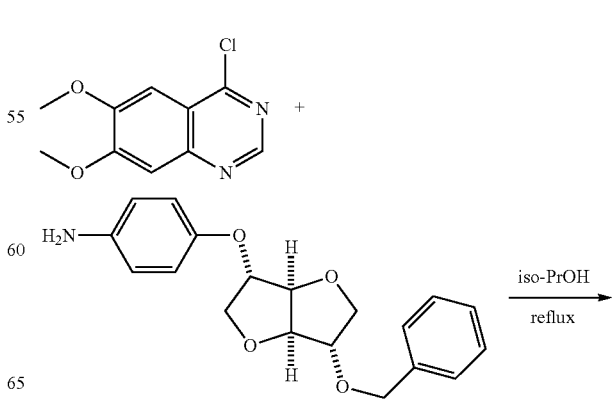

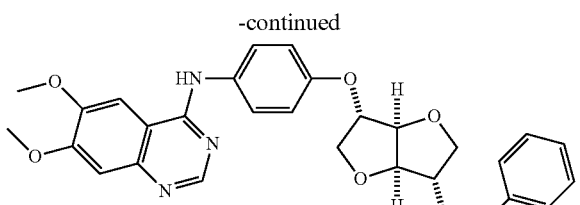

To a suspension of 4-chloro-6,7-dimethoxyquinazoline (336 mg, 1.5 mmol) in a 100 mL single neck RB flask in iso-propanol (30 mL) was added a solution of 4-[[(3S,3aR,6S,6aR)-3-benzyloxy-2,3,3a,5,6,6a-hexahydrofuro[3,2-b]furan-6-yl]oxy]aniline (654 mg, 2 mmol) in iso-propanol (15 mL) at room temperature under an argon atmosphere. The resulting ash suspension was heated to reflux (110° C., bath temperature) which produced a clear light brown solution when the temperature reached ~90° C. Within few minutes some yellow precipitate started to form which was stirred for 4 h.

Then, it was cooled to room temperature and later it was stored in the refrigerator for 1 h. The resulting light yellow solids were collected by filtration and washed with iso-propanol. The solids were dried over weekend to obtain 660 mg (85%) of N-[4-[[(3S,3aR,6S,6aR)-3-benzyloxy-2,3,3a,5,6,6a-hexahydrofuro[3,2-b]furan-6-yl]oxy]phenyl]-6,7-dimethoxy-quinazolin-4-amine. TLC analysis (1:1, Hex:EA) indicated the presence of some impurity. Then, it was triturated with hot EA and the solids were collected by filtration to obtain 400 mg (52%) of pure N-[4-[[(3S,3aR,6S,6aR)-3-benzyloxy-2,3,3a,5,6,6a-hexahydrofuro[3,2-b]furan-6-yl]oxy]phenyl]-6,7-dimethoxy-quinazolin-4-amine as off-white solid. $^1$H-NMR (DMSO-d6): δ 11.35 (s, 1H), 8.75 (s, 1H), 8.32 (s, 1H), 7.58-755 (m, 2H), 7.4-7.37 (m, 6H), 7.09 (d, J=8.9 Hz, 2H), 4.9 (d, J=2.4 Hz, 1H), 4.72 (d, J=4.2 Hz, 1H), 4.62 (d, J=3.9 Hz, 1H), 4.59 (s, 2H), 4.56 (d, J=11.9 Hz, 1H), 4.09 (d, J=3.4 Hz, 1H), 4.02 (dd, J=10.2, 4.2 Hz, 1H), 4.01 (s, 3H), 3.99 (s, 3H), 3.97-3.84 (m, 2H). LC/MS calcd. for $C_{29}H_{29}N_3O_6$ [(M+H)$^+$] 516, obsd. 516.

Example AA

Synthesis of N-[4-[[(3S,3aR,6S,6aR)-3-benzyloxy-2,3,3a,5,6,6a-hexahydrofuro[3,2-b]furan-6-vi]oxy]-3-chloro-phenyl]-6,7-dimethoxy-quinazolin-4-amine

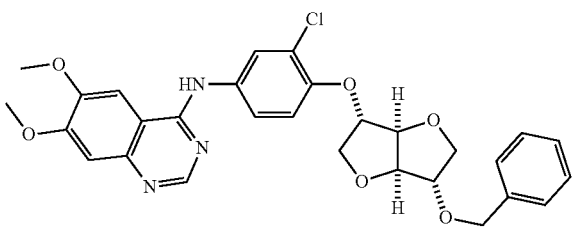 [SMILES: COc1cc2ncnc(Nc3ccc(O[C@H]4CO[C@H]5[C@@H]4OC[C@@H]5OCc4ccccc4)c(Cl)c3)c2cc1OC]

Step 1: Preparation of (3S,3aR,6S,6aR)-3-benzyloxy-6-(2-chloro-4-nitrophenoxy)-2,3,3a,5,6,6a-hexahydrofuro[3,2-b]furan

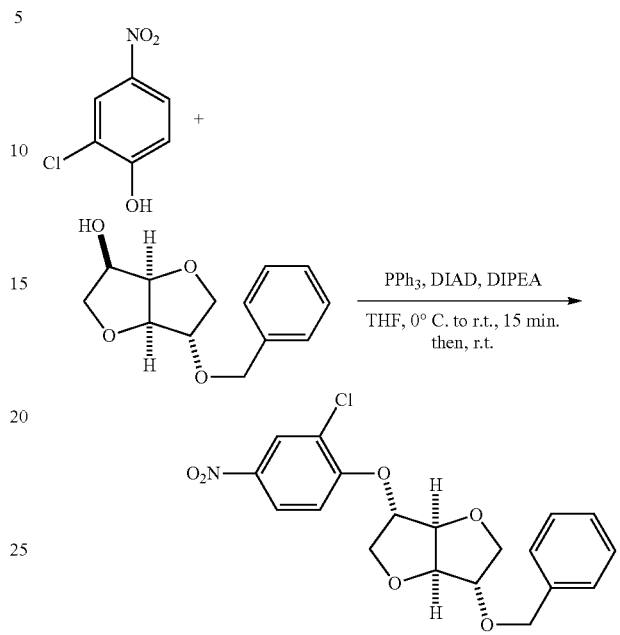

To a solution of triphenylphosphine (5.9 g, 22.5 mmol) in THF (150 mL) in a 500 mL 3-neck RB flask was added di-isopropylazodicarboxylate (4.55 g, 4.43 mL, 22.5 mmol) at 0-5° C. (ice+water) for 5-10 minutes under an argon atmosphere. The resulting light yellow suspension was stirred for 10-15 minutes at this temperature. Then, a clear solution of 2-chloro-4-nitrophenol (2.6 g, 15 mmol) in THF (100 mL) was added drop-wise over 5-10 minutes. After 2 minutes, the cooling bath was removed to allow the reaction mixture to warm to room temperature where it was stirred for 10-15 minutes.

Then, a solution of isosorbide 2-benzyl ether (4.25 g, 18 mmol) (prepared following the literature procedure, Carbohydrate Research 1994, 261, 255-266) in THF (100 mL) was slowly added followed by the neat triethylamine (2.28 g, 3.2 mL, 22.5 mmol) at room temperature. The resulting light yellow suspension was stirred for 48 h by which time TLC (1:1, Hex:EA) analysis of the reaction mixture indicated the appearance of a new spot. Then, the solvent was removed under vacuum and the crude residue was purified using an ISCO (330 g) column chromatography to afford 5.29 g (90%) of (3S,3aR,6S,6aR)-3-benzyloxy-6-(2-chloro-4-nitrophenoxy)-2,3,3a,5,6,6a-hexahydrofuro[3,2-b]furan as a light brown viscous oil. LC/MS calcd. for $C_{19}H_{18}ClNO_6$ [(M-H)$^-$] 390, obsd. 390.

Step 2: Preparation of 4-[[(3S,3aR,6S,6aR)-3-benzyloxy-2,3,3a,5,6,6a-hexahydrofuro[3,2-b]furan-6-yl]oxy]-3-chloro-aniline

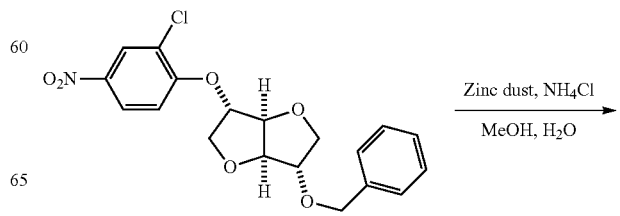

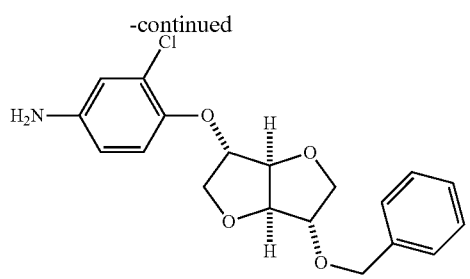

To a solution of (3S,3aR,6S,6aR)-3-benzyloxy-6-(2-chloro-4-nitrophenoxy)-2,3,3a,5,6,6a-hexahydrofuro[3,2-b]furan (5.29 g, 13.5 mmol) in methanol (150 mL) in a 500 mL single neck RB flask were added an excess of zinc dust (9.81 g, 150 mmol) and ammonium chloride (12.03 g, 225 mmol). Then, water (25 mL) was added at room temperature under an argon atmosphere. It was exothermic reaction after the addition of water. Cement colored clusters formed after the addition of water. It was stirred for 2 h and then the reaction mixture was heated with a heat gun.

After being stirred for another 1 h at room temperature, TLC analysis of the mixture indicated the absence of starting material. The excess zinc dust was filtered off and the solid cake was washed with methanol and water. The solvent was removed under vacuum and the organic compound was extracted into EA (2×100 mL) while the combined extracts were washed with brine solution. The organic layer was dried over anhydrous MgSO₄, filtration and concentration gave 4.79 g (98%) of 4-[[(3S,3aR,6S,6aR)-3-benzyloxy-2,3,3a,5,6,6a-hexahydrofuro[3,2-b]furan-6-yl]oxy]-3-chloro-aniline as a light brown oil. LC/MS calcd. for $C_{19}H_{20}ClNO_4$ [(M−H)⁻]360, obsd. 360.

Step 3: Preparation of N-[4-[[(3S,3aR,6S,6aR)-3-benzyloxy-2,3,3a,5,6,6a-hexahydrofuro[3,2-b]furan-6-yl]oxy]-3-chloro-phenyl]-6,7-dimethoxy-quinazolin-4-amine

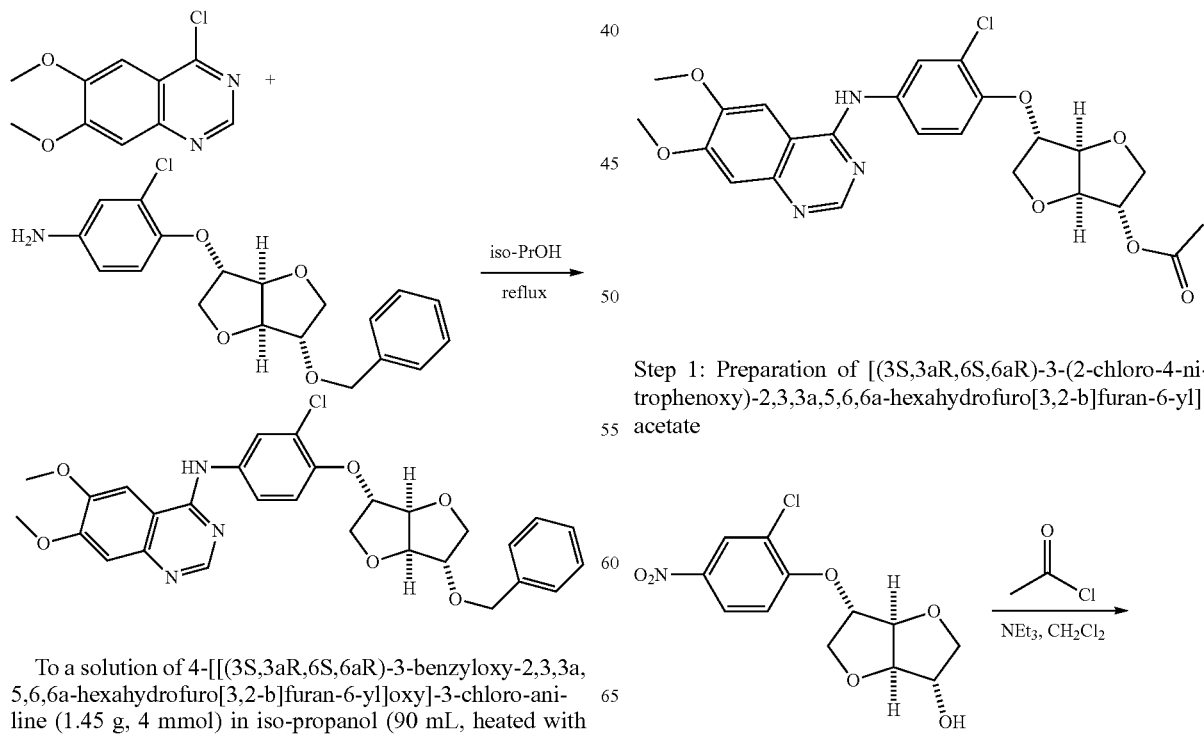

To a solution of 4-[[(3S,3aR,6S,6aR)-3-benzyloxy-2,3,3a,5,6,6a-hexahydrofuro[3,2-b]furan-6-yl]oxy]-3-chloro-aniline (1.45 g, 4 mmol) in iso-propanol (90 mL, heated with heat gun to dissolve) in a 250 mL single neck RB flask was added a solid 4-chloro-6,7-dimethoxyquinazoline (673 mg, 3 mmol) at room temperature under an argon atmosphere. The resulting suspension was heated to reflux (110° C., bath temperature) which produced a clear light brown solution when the temperature reached ~90° C. Within few minutes some yellow precipitate started to form which was stirred for 4 h.

Then, it was cooled to room temperature and the resulting light yellow solids were collected by filtration and washed with iso-propanol. The solids were dried to obtain 880 mg of N-[4-[[(3S,3aR,6S,6aR)-3-benzyloxy-2,3,3a,5,6,6a-hexahydrofuro[3,2-b]furan-6-yl]oxy]-3-chloro-phenyl]-6,7-dimethoxy-quinazolin-4-amine. TLC analysis (1:1, Hex:EA) indicated the presence of some impurity. Then, it was attempted to dissolve in hot methanol, but it was not dissolved completely. Then, the suspension was stored in the freezer for 15 h and the solids were collected by filtration to obtain 780 mg (47%) of pure N-[4-[[(3S,3aR,6S,6aR)-3-benzyloxy-2,3,3a,5,6,6a-hexahydrofuro[3,2-b]furan-6-yl]oxy]-3-chloro-phenyl]-6,7-dimethoxy-quinazolin-4-amine a light yellow solid. ¹H-NMR (DMSO-d6): δ 11.35 (s, 1H), 8.81 (s, 1H), 8.38 (s, 1H), 7.9 (s, 1H), 7.64 (d, J=8.9 Hz, 1H), 7.4-7.28 (m, 7H), 5.0 (d, J=2.2 Hz, 1H), 4.74 (d, J=4.2 Hz, 1H), 4.64 (d, J=4.2 Hz, 1H), 4.59 (s, 2H), 4.58 (d, J=12.0 Hz, 1H), 4.1 (d, J=3.0 Hz, 1H), 4.04 (d, J=4.2 Hz, 1H), 4.02 (s, 3H), 3.99 (s, 3H), 3.94-3.92 (m, 1H) 3.87 (dd, J=10.2, 4.2 Hz, 1H). LC/MS calcd. for $C_{29}H_{28}ClN_3O_6$ [(M+H)⁺] 551, obsd. 551.

Example BB

Synthesis of [(3S,3aR,6S,6aR)-3-[2-chloro-4-[(6,7-dimethoxyquinazolin-4-yl)amino]phenoxy]-2,3,3a,5,6,6a-hexahydrofuro[3,2-b]furan-6-yl] acetate Step 1: Preparation of [(3S,3aR,6S,6aR)-3-(2-chloro-4-nitrophenoxy)-2,3,3a,5,6,6a-hexahydrofuro[3,2-b]furan-6-yl] acetate

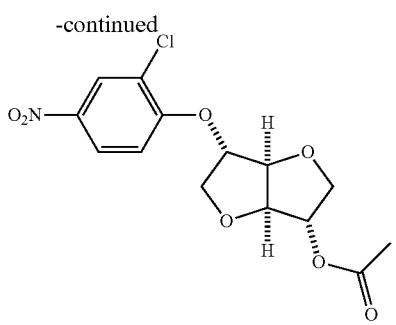

To a colorless solution of (3S,3aR,6S,6aR)-6-(2-chloro-4-nitro-phenoxy)-2,3,3a,5,6,6a-hexahydrofuro[3,2-b]furan-3-ol (1.05 g, 3.5 mmol) in dichloromethane (30 mL) in a 100 mL single neck RB flask were added first acetyl chloride (353 mg, 319 uL, 4.5 mmol) followed by the neat triethylamine (911 mg, 1.25 mL, 9 mmol) at 0-5° C. under an argon atmosphere. The resulting light brown solution was allowed to warm to room temperature without removing the cooling bath and then it was stirred for 15 h at room temperature by which time TLC (1:1, Hex:EA) analysis of the reaction mixture indicated the appearance of a new spot.

Then, it was diluted with water and the organic compound was extracted into dichloromethane (2×50 mL). The combined organic extracts were washed with brine solution and dried over anhydrous MgSO$_4$. Filtration and concentration gave the crude light brown oil which was purified using an ISCO (120 g) column chromatography to obtain 1.14 g (95%) of [(3S,3aR,6S,6aR)-3-(2-chloro-4-nitrophenoxy)-2,3,3a,5,6,6a-hexahydrofuro[3,2-b]furan-6-yl]acetate as a light yellow colored paste. LC/MS calcd. for $C_{14}H_{14}ClNO_7$ [(M–H)$^-$] 342, obsd. 342.

Step 2: Preparation of [(3S,3aR,6S,6aR)-3-(4-amino-2-chloro-phenoxy)-2,3,3a,5,6,6a-hexahydrofuro[3,2-b]furan-6-yl] acetate

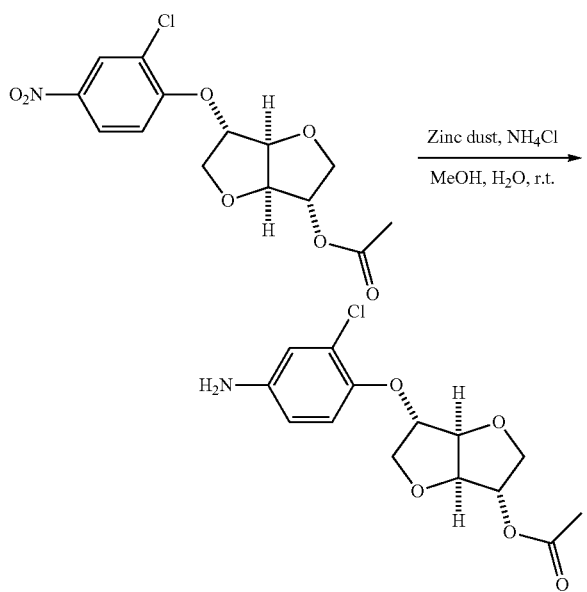

To a solution of [(3S,3aR,6S,6aR)-3-(2-chloro-4-nitrophenoxy)-2,3,3a,5,6,6a-hexahydrofuro[3,2-b]furan-6-yl] acetate (1.14 g, 3.3 mmol) in methanol (40 mL) in a single neck 100 mL RB flask were added an excess zinc dust (2.15 g, 33 mmol) and ammonium chloride (2.64 g, 49.5 mmol) followed by water (20 mL) was added at room temperature under an argon atmosphere. It was an exothermic reaction after the addition of water. The reaction mixture was stirred for 30 minutes and then heated with a heat gun. Then, it was stirred for another 2.5 h at room temperature at which time TLC analysis of the mixture indicated the absence of starting material.

The excess zinc dust was filtered off and the solid cake was washed with EA and water. The solvent was removed under vacuum and the organic compound was extracted into EA (3×50 mL) while the combined extracts were washed with brine solution. The organic layer was dried over anhydrous MgSO$_4$, filtration and concentration gave the crude oil which was purified using an ISCO (220 g) column chromatography to obtain 880 mg (84%) of [(3S,3aR,6S,6aR)-3-(4-amino-2-chloro-phenoxy)-2,3,3a,5,6,6a-hexahydrofuro[3,2-b]furan-6-yl] acetate as a viscous colorless oil. LC/MS calcd. for $C_{14}H_{16}ClNO_5$ [(M–H)$^-$] 312, obsd. 312.

Step 3: Preparation of [(3S,3aR,6S,6aR)-3-[2-chloro-4-[(6,7-dimethoxyquinazolin-4-yl)amino]phenoxy]-2,3,3a,5,6,6a-hexahydrofuro[3,2-b]furan-6-yl] acetate

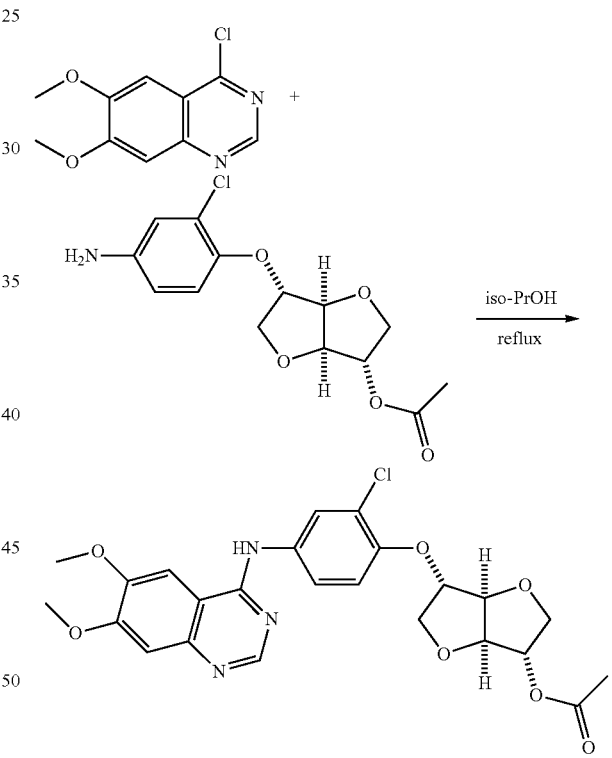

To a suspension of 4-chloro-6,7-dimethoxyquinazoline (337 mg, 1.5 mmol) in iso-propanol (35 mL) in a single neck 100 mL RB flask was added a solution of [(3S,3aR,6S,6aR)-3-(4-amino-2-chloro-phenoxy)-2,3,3a,5,6,6a-hexahydrofuro[3,2-b]furan-6-yl] acetate (627 mg, 2.0 mmol) in iso-propanol (10 mL) at room temperature under an argon atmosphere. The resulting suspension was heated to reflux (110° C., bath temperature) which produced a clear solution at ~80° C. Within a few minutes some yellow precipitate started to form which was stirred for 4 h at reflux.

Then, it was cooled to room temperature and the resulting light yellow solids were collected by filtration and washed with EA. After air drying, 750 mg (100%) of [(3S,3aR,6S, 6aR)-3-[2-chloro-4-[(6,7-dimethoxyquinazolin-4-yl)amino]phenoxy]-2,3,3a,5,6,6a-hexahydrofuro[3,2-b]furan-6-yl] acetate was isolated as a light yellow solid. $^1$H-NMR (DMSO-d6): δ 11.49 (s, 1H), 8.82 (s, 1H), 8.37 (s, 1H), 7.89 (d, J=2.2 Hz, 1H), 7.68 (dd, J=8.4, 2.2 Hz, 1H), 7.35-7.33 (m, 2H), 5.10 (d, J=3.4 Hz, 1H), 5.04 (s, 1H), 4.69-4.66 (m, 2H), 4.07-4.04 (m, 2H), 4.01 (s, 3H), 3.99 (s, 3H), 3.97-3.95 (m, 1H), 3.89 (d, J=7.8 Hz, 1H), 2.04 (s, 3H). LC/MS calcd. for $C_{24}H_{24}ClN_3O_7$ [(M+H)$^+$] 502, obsd. 502.

Example CC

Preparation of [(3S,3aR,6S,6aR)-3-[2-chloro-4-(thieno[3,2-d]pyrimidin-4-ylamino)phenoxy]-2,3,3a,5,6,6a-hexahydrofuro[3,2-b]furan-6-yl] acetate

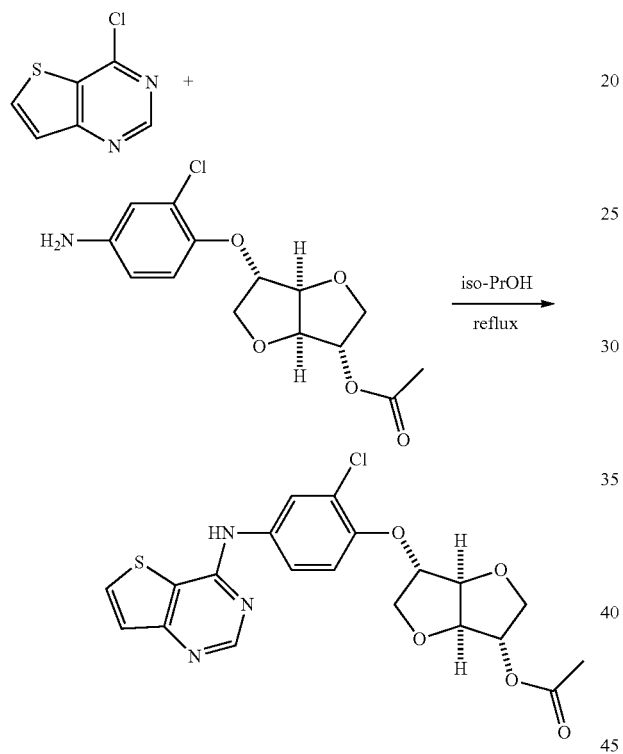

To a mixture of 4-chlorothieno[3,2-d]pyrimidine (256 mg, 1.5 mmol) and [(3S,3aR,6S,6aR)-3-(4-amino-2-chlorophenoxy)-2,3,3a,5,6,6a-hexahydrofuro[3,2-b]furan-6-yl]acetate (530 mg, 1.7 mmol) in a single neck 100 mL RB flask was added iso-propanol (25 mL) at room temperature under an argon atmosphere. It gave mostly a clear solution at room temperature with a few solid particles in the bottom which dissolved at reflux. After 1 h reflux (110° C., bath temperature), a light yellow precipitate formed and it was stirred for 4 h.

The light yellow suspension was diluted with EA (~10 mL) during reflux and then cooled to room temperature. The resulting light yellow solids were collected by filtration and washed with EA. After air drying, 595 mg (89%) of [(3S,3aR,6S,6aR)-3-[2-chloro-4-(thieno[3,2-d]pyrimidin-4-ylamino)phenoxy]-2,3,3a,5,6,6a-hexahydrofuro[3,2-b]furan-6-yl] acetate was isolated as a light yellow solid. $^1$H-NMR (DMSO-d6): δ 11.23 (s, 1H), 8.89 (s, 1H), 8.49 (d, J=5.6 Hz, 1H), 7.89 (d, J=2.8 Hz, 1H), 7.63 (d, J=8.9 Hz, 1H), 7.58 (d, J=5.0 Hz, 1H), 7.35 (d, J=8.4 Hz, 1H), 5.1 (d, J=3.4 Hz, 1H), 5.04 (s, 1H), 4.68-4.65 (m, 2H), 4.06 (dd, J=10.1, 3.9 Hz, 1H), 3.99-3.95 (m, 2H), 3.89 (d, J=9.5 Hz, 1H), 2.04 (s, 3H). LC/MS calcd. for $C_{20}H_{18}ClN_3O_5S$ [(M+H)$^+$] 448, obsd. 448.

Example DD

Synthesis of [(3S,3aR,6S,6aR)-3-[2-chloro-4-[(6,7-dimethoxyquinazolin-4-yl)amino]phenoxy]-2,3,3a,5,6,6a-hexahydrofuro[3,2-b]furan-6-yl] benzoate

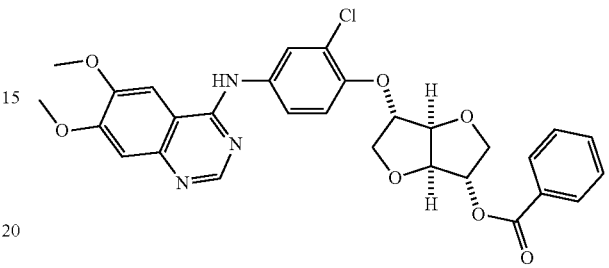

Step 1: Preparation of [(3S,3aR,6S,6aR)-3-(2-chloro-4-nitro-phenoxy)-2,3,3a,5,6,6a-hexahydrofuro[3,2-b]furan-6-yl] benzoate

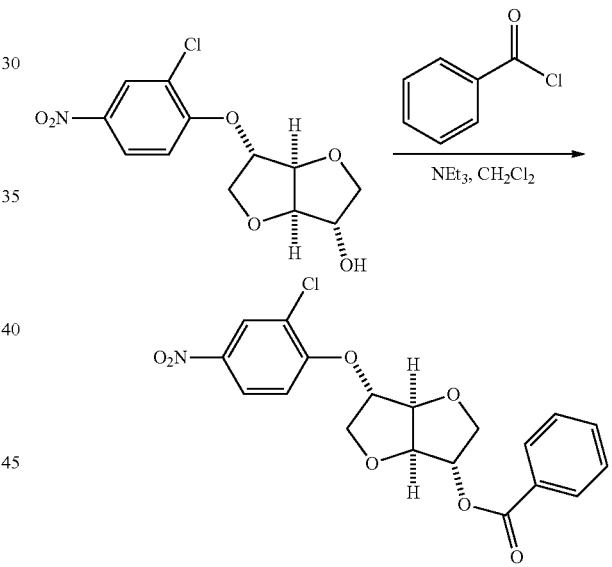

To a colorless solution of (3S,3aR,6S,6aR)-6-(2-chloro-4-nitro-phenoxy)-2,3,3a,5,6,6a-hexahydrofuro[3,2-b]furan-3-ol (3.01 g, 10 mmol) in dichloromethane (60 mL) in a 100 mL single neck RB flask were added first benzoyl chloride (1.68 g, 1.4 mL, 12 mmol) then followed by an excess of triethylamine (2.53 g, 3.48 mL, 25 mmol) at 0-5° C. under argon atmosphere. The resulting light brown solution was warmed to room temperature without removing the cooling bath and then stirred for 36 h at which time TLC (1:1, Hex:EA) analysis of the reaction mixture indicated the appearance of a new less polar spot.

Then, it was diluted with water and the organic compound was extracted into dichloromethane. The combined organic extracts were washed with brine solution and dried over anhydrous MgSO$_4$. Filtration and concentration gave the crude light brown oil which was purified using an ISCO (220 g) column chromatography to afford 3.8 g (94%) of [(3S, 3aR,6S,6aR)-3-(2-chloro-4-nitro-phenoxy)-2,3,3a,5,6,6a-hexahydrofuro[3,2-b]furan-6-yl]benzoate as a viscous light brown oil. LC/MS calcd. for $C_{19}H_{16}ClNO_7$ [(M−H)⁻] 404, obsd. 404.

Step 2: Preparation of [(3S,3aR,6S,6aR)-3-(4-amino-2-chloro-phenoxy)-2,3,3a,5,6,6a-hexahydrofuro[3,2-b]furan-6-yl] benzoate

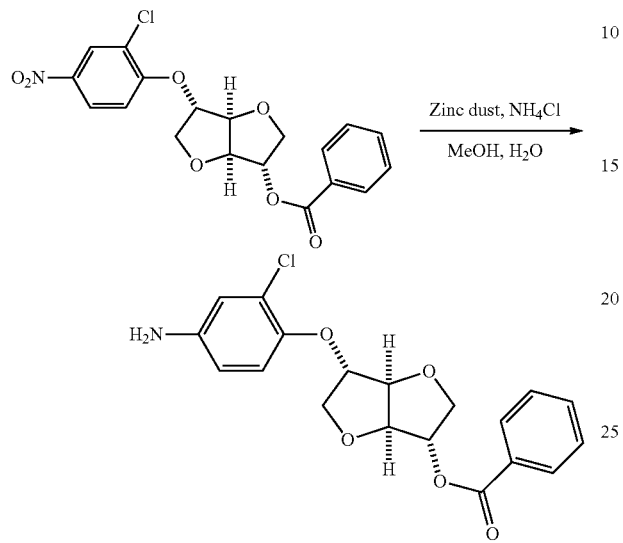

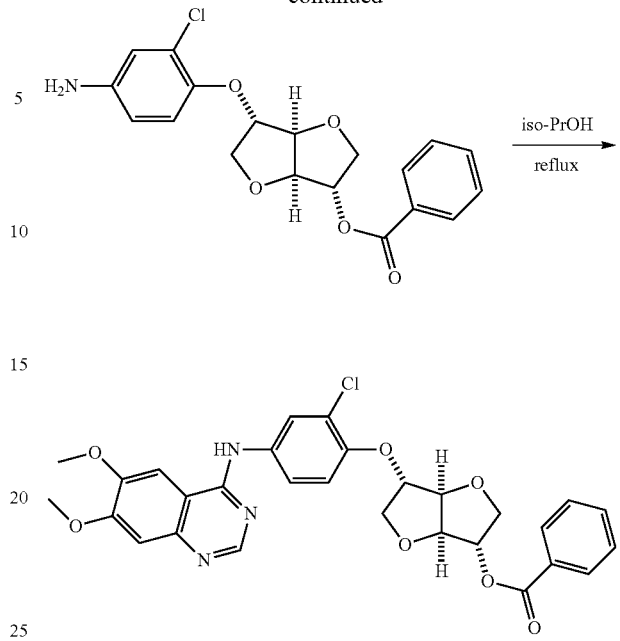

To a solution of [(3S,3aR,6S,6aR)-3-(2-chloro-4-nitro-phenoxy)-2,3,3a,5,6,6a-hexahydrofuro[3,2-b]furan-6-yl] benzoate (3.04 g, 7.5 mmol) in methanol (70 mL) in a 250 mL single neck RB flask were added an excess zinc dust (4.9 g, 75 mmol) and ammonium chloride (6.02 g, 112.5 mmol) followed by water (35 mL) at room temperature under an argon atmosphere. It was an exothermic reaction after the addition of water. The reaction mixture was heated with a heat gun twice at 30 minute intervals.

Then, it was stirred for a total 3-4 h at room temperature by which time TLC analysis of the mixture indicated the presence of additional starting material. Then, the reaction mixture was heated to 60° C. and stirred for 1.5 h. The reaction mixture was cooled to room temperature and the excess zinc dust was filtered off using cotton plug while the solid cake was washed with methanol and water. The filtrate was removed under vacuum and the aqueous layer was saturated with the solid NaCl. Then, the organic compound was extracted with EA (3×50 mL) and the combined extracts were washed with brine solution. The organic layer was dried over anhydrous MgSO₄, filtration and concentration yielded a crude 2.4 g (85%) of [(3S,3aR,6S,6aR)-3-(4-amino-2-chloro-phenoxy)-2,3,3a,5,6,6a-hexahydrofuro[3,2-b]furan-6-yl] benzoate as a light brown oil which was directly used for the next step without purification. LC/MS calcd. for $C_{19}H_{18}ClNO_5$ [(M−H)⁻] 374, obsd. 374.

Step 3: Preparation of [(3S,3aR,6S,6aR)-3-[2-chloro-4-[(6,7-dimethoxyquinazolin-4-yl)amino]phenoxy]-2,3,3a,5,6,6a-hexahydrofuro[3,2-b]furan-6-yl] benzoate

To a mixture of 4-chloro-6,7-dimethoxyquinazoline (562 mg, 2.5 mmol) and [(3S,3aR,6S,6aR)-3-(4-amino-2-chloro-phenoxy)-2,3,3a,5,6,6a-hexahydrofuro[3,2-b]furan-6-yl] benzoate (1.4 g, 3.7 mmol) in a 100 mL single neck RB flask was added iso-propanol (40 mL) at room temperature under an argon atmosphere. The resulting suspension was heated to reflux (110° C., bath temperature) which gave a clear solution when the temperature reached 95° C. After 30 minutes reflux, a light yellow precipitate formed and it was stirred for 6 h.

The reaction mixture (suspension) was diluted with EA at reflux and cooled to room temperature. The resulting light yellow solids were collected by filtration and washed with EA. After air drying, 959 mg (70%) of [(3S,3aR,6S,6aR)-3-[2-chloro-4-[(6,7-dimethoxyquinazolin-4-yl)amino]phenoxy]-2,3,3a,5,6,6a-hexahydrofuro[3,2-b]furan-6-yl] benzoate was isolated as a light yellow solid. ¹H-NMR (DMSO-d6): δ 11.45 (s, 1H), 8.84 (s, 1H), 8.32 (s, 1H), 8.0 (d, J=7.3 Hz, 2H), 7.87 (d, J=2.8 Hz, 1H), 7.69-7.66 (m, 2H), 7.55 (t, J=7.8 Hz, 2H), 7.39 (d, J=8.4 Hz, 1H), 7.33 (s, 1H), 5.37 (d, J=2.8 Hz, 1H), 5.09 (d, J=2.2 Hz, 1H) 4.85-4.83 (m, 2H), 4.13 (d, J=3.4 Hz, 1H), 4.11 (d, 3.4 Hz, 1H), 4.09 (d, J=3.4 Hz, 1H), 4.06 (d, J=10.1 Hz, 1H), 4.01 (s, 3H), 3.99 (s, 3H). LC/MS calcd. for $C_{29}H_{26}ClN_3O_7$ [(M+H)⁺] 564, obsd. 564.

Example EE

Preparation of [(3S,3aR,6S,6aR)-3-[2-chloro-4-(thieno[3,2-d]pyrimidin-4-ylamino)phenoxy]-2,3,3a,5,6,6a-hexahydrofuro 3,2-b]furan-6-yl benzoate -continued

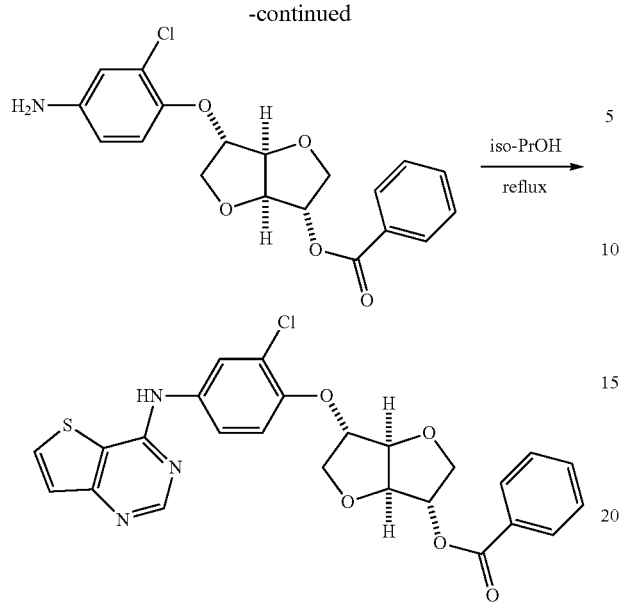

To a mixture of 4-chlorothieno[3,2-d]pyrimidine (171 mg, 1.0 mmol) and [(3S,3aR,6S,6aR)-3-(4-amino-2-chlorophenoxy)-2,3,3a,5,6,6a-hexahydrofuro[3,2-b]furan-6-yl] benzoate (420 mg, 1.1 mmol) in a 50 mL single neck RB flask was added iso-propanol (30 mL) at room temperature under an argon atmosphere. The resulting suspension was heated to reflux (110° C., bath temperature) which gave a clear solution when the temperature reached 100° C. After 3 h reflux, a white precipitate started to form which was stirred for 6 h. It was cooled to 80° C. and stirred for another 15 h at this temperature.

Then, the reaction mixture (suspension) was diluted with EA (5 mL) and cooled to room temperature. The resulting light yellow solids were collected by filtration and washed with EA. After air drying, 448 mg (88%) of [(3S,3aR,6S,6aR)-3-[2-chloro-4-(thieno[3,2-d]pyrimidin-4-ylamino)phenoxy]-2,3,3a,5,6,6a-hexahydrofuro[3,2-b]furan-6-yl] benzoate was isolated as a light yellow solid. $^1$H-NMR (DMSO-d6): δ 11.4 (s, 1H), 8.9 (s, 1H), 8.5 (d, J=5.0 Hz, 1H), 8.0-7.98 (m, 2H), 7.9 (d, J=2.2 Hz, 1H), 7.69-7.64 (m, 2H), 7.6 (d, J=5.6 Hz, 1H), 7.55-7.52 (m, 2H), 7.37 (d, J=8.4 Hz, 1H), 5.37 (d, J=3.4 Hz, 1H), 5.09 (d, J=2.8 Hz, 1H) 4.85-4.83 (m, 2H), 4.12 (d, J=3.4 Hz, 1H), 4.11 (dd, J=9.5, 3.4 Hz, 1H), 4.06 (d, J=10.1, 1H), 4.02 (dd, J=10.1, 1.1 Hz, 1H). LC/MS calcd. for $C_{25}H_{20}ClN_3O_5S$ [(M+H)$^+$] 510, obsd. 510.

Example FF

Synthesis of [(3S,3aR,6S,6aR)-3-[2-[(1-methylsulfonyl-4-piperidyl)amino]pyrimidin-4-yl]oxy-2,3,3a,5,6,6a-hexahydrofuro[3,2-b]furan-6-yl] acetate

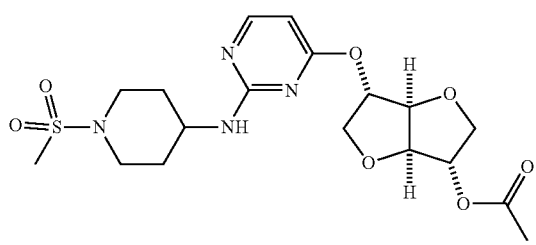 [SMILES: CC(=O)O[C@H]1CO[C@H]2[C@@H]1OC[C@@H]2Oc1ccnc(NC2CCN(S(C)(=O)=O)CC2)n1]

Step 1: Preparation of (3S,3aR,6S,6aR)-6-(2-methylsulfanylpyrimidin-4-yl)oxy-2,3,3a,5,6,6a-hexahydrofuro[3,2-b]furan-3-ol

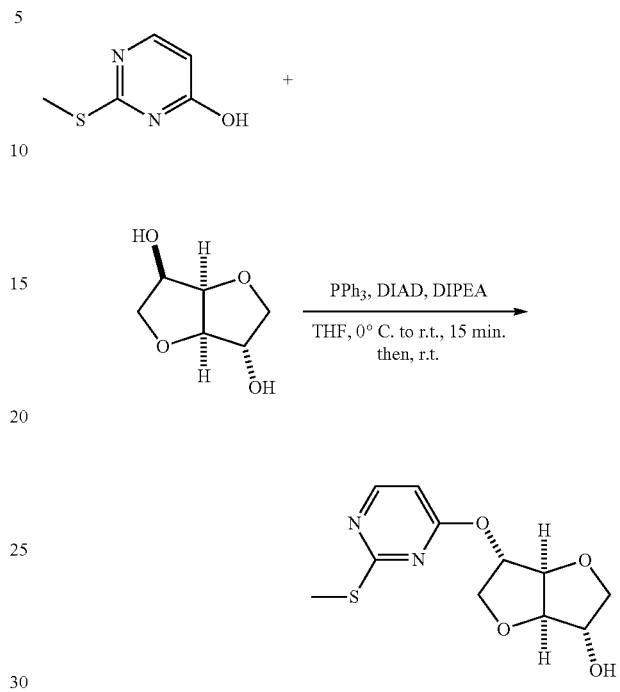

To a solution of triphenylphosphine (3.94 g, 15 mmol) in THF (60 mL) in a 250 mL 2-neck RB flask was added di-isopropylazodicarboxylate (3.04 g, 2.96 mL, 15 mmol) at 0-5° C. (ice+water) for 5 minutes under an argon atmosphere. The resulting light yellow suspension was stirred for 10-15 minutes at this temperature. A solution of 2-methylthiopyrimidin-4-ol (1.42 g, 10 mmol) in THF (80 mL, heated to dissolve) was added drop-wise over 5 minutes which resulted in the formation of a very thick suspension. After 2 minutes, the cooling bath was removed to allow the reaction mixture to warm to room temperature and it was stirred for 10 minutes.

Then, a solution of isosorbide (1.75 g, 12 mmol) in THF (50 mL) was slowly added followed by the neat DIPEA (1.94 g, 2.62 mL, 15 mmol) at room temperature. The resulting light yellow suspension was stirred for 48 h. During this period (after 15 h), it turned into a light brown solution and after 48 h TLC (1:1, Hex:EA) analysis of the reaction mixture indicated the appearance of a new spot. The solvent was removed under vacuum and the LCMS analysis of the reaction mixture indicated the presence of the desired mass. The crude residue was purified using an ISCO (220 g) column chromatography to obtain 2.43 g (90%) of (3S,3aR,6S,6aR)-6-(2-methylsulfanylpyrimidin-4-yl)oxy-2,3,3a,5,6,6a-hexahydrofuro[3,2-b]furan-3-ol as a white low melting solid (paste). $^1$H-NMR (DMSO-d6): δ 8.15 (d, J=5.7 Hz, 1H), 6.02 (d, J=5.6 Hz, 1H), 5.30 (d, J=3.4 Hz, 1H), 5.16 (d, 3.9 Hz, 1H), 4.64 (d, J=3.7 Hz, 1H), 4.48 (d, J=3.4 Hz, 1H), 4.15 (br, s, 1H), 4.02 (dd, J=10.1, 3.4 Hz, 1H), 3.93 (d, J=9.8 Hz, 1H), 3.81 (dd, J=10.0, 3.4 Hz, 1H), 3.74 (d, J=9.9 Hz, 1H), 2.56 (s, 3H). LC/MS calcd. for $C_{11}H_{14}N_2O_4S$ [(M+H)$^+$] 271, obsd. 271.

Step 2: Preparation of [(3S,3aR,6S,6aR)-3-(2-methylsulfanylpyrimidin-4-yl)oxy-2,3,3a,5,6,6a-hexahydrofuro[3,2-b]furan-6-yl] acetate

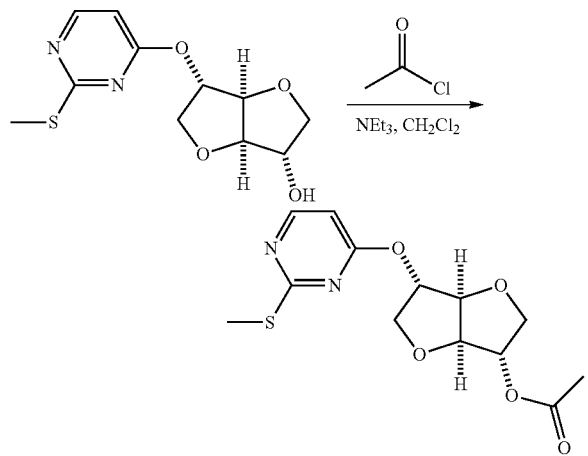

To a colorless solution of (3S,3aR,6S,6aR)-6-(2-methylsulfanylpyrimidin-4-yl)oxy-2,3,3a,5,6,6a-hexahydrofuro[3,2-b]furan-3-ol (2.4 g, 8.8 mmol) in dichloromethane (80 mL) in a 250 mL 2-neck RB flask were added first acetyl chloride (902 mg, 817 uL, 11.5 mmol) followed by an excess of triethylamine (2.32 g, 3.2 mL, 23 mmol) at 0-5° C. under an argon atmosphere. The resulting light brown solution was warmed to room temperature without removing cooling bath and then stirred for 15 h at which time TLC (1:1, Hex:EA) analysis of the reaction mixture indicated the appearance of a new spot.

Then, it was diluted with water and the organic compound was extracted into dichloromethane (2×100 mL). The combined organic extracts were washed with brine solution and dried over anhydrous MgSO$_4$. Filtration and concentration yielded crude light brown oil which was purified using an ISCO (220 g) column chromatography to obtain 2.61 g (95%) of [(3S,3aR,6S,6aR)-3-(2-methylsulfanylpyrimidin-4-yl)oxy-2,3,3a,5,6,6a-hexahydrofuro[3,2-b]furan-6-yl] acetate as a viscous light yellow oil.

Step 3: Preparation of [(3S,3aR,6S,6aR)-3-(2-methylsulfinylpyrimidin-4-yl)oxy-2,3,3a,5,6,6a-hexahydrofuro[3,2-b]furan-3-yl] acetate

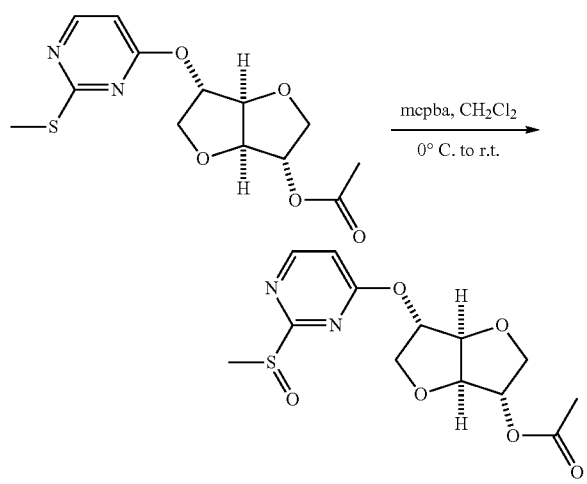

To a solution of [(3S,3aR,6S,6aR)-3-(2-methylsulfanylpyrimidin-4-yl)oxy-2,3,3a,5,6,6a-hexahydrofuro[3,2-b]furan-3-yl] acetate (2.6 g, 8.3 mmol) in dichloromethane (100 mL) in a 250 mL 2-neck RB flask was added mcpba (2.24 g, 13 mmol, 77%) at 0-5° C. (ice+water) in one portion under an argon atmosphere. The resulting colorless solution was stirred for 4 h at 0° C. to r.t. (the cooling bath was not removed) at which time TLC analysis of the mixture indicated the presence of two polar spots and the disappearance of starting material.

Then, the reaction mixture was diluted with water and the two layers were separated and the aqueous layer was extracted one more time with dichloromethane. The combined extracts were washed with saturated sodium bicarbonate solution (2×150 mL) followed by water and brine solution. The organic layer was dried over anhydrous MgSO$_4$, filtered and concentrated to obtain 2.9 g of paste which was purified using an ISCO (220 g) column chromatography to obtain 1.59 g (58%) of [(3S,3aR,6S,6aR)-3-(2-methylsulfinylpyrimidin-4-yl)oxy-2,3,3a,5,6,6a-hexahydrofuro[3,2-b]furan-3-yl] acetate (more polar) as a white solid and 437 mg of [(3S,3aR,6S,6aR)-3-(2-methylsulfonylpyrimidin-4-yl)oxy-2,3,3a,5,6,6a-hexahydrofuro[3,2-b]furan-3-yl] acetate (less polar) as a white solid.

Step 4: Preparation of tert-butyl-4-[[4-[[(3S,3aR,6S,6aR)-6-acetoxy-2,3,3a,5,6,6a-hexahydrofuro[3,2-b]furane-3-yl]oxy]pyrimidine-2-yl]amino]piperidine-1-carboxylate

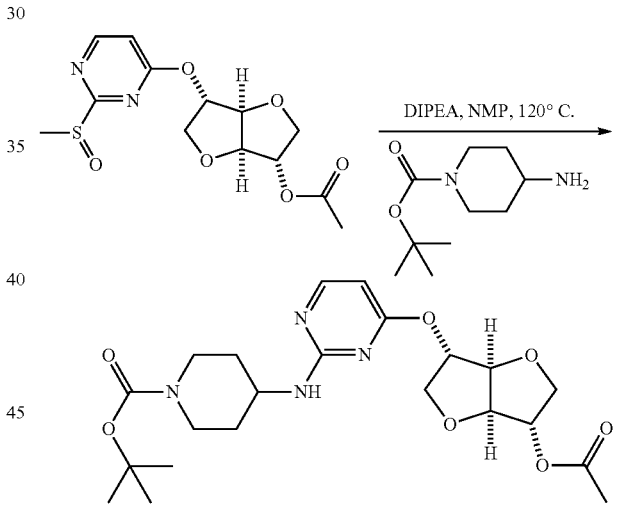

To a solution of [(3S,3aR,6S,6aR)-3-(2-methylsulfinylpyrimidin-4-yl)oxy-2,3,3a,5,6,6a-hexahydrofuro[3,2-b]furan-3-yl] acetate (1.59 g, 4.8 mmol) in NMP (20 mL) in a 100 mL 2-neck RB flask were added 4-aminopiperidine-1-carboxylic acid tert-butyl ester (1.94 g, 9.68 mmol) followed by DIPEA (1.25 g, 1.68 mL, 9.68 mmol) at room temperature under an argon atmosphere. The resulting cloudy solution was heated to 120° C. (bath temperature) which gave a clear solution (slightly yellowish). Then, the reaction mixture was stirred for 3 h at this temperature by which time it turned into a brown solution which indicated that the reaction was complete. Also, TLC (1:1, Hex:EA) analysis of the mixture indicated the presence of a new spot and disappearance of the starting material. The reaction mixture was cooled to room temperature and diluted with water. After water addition, a white precipitate formed, but it completely dissolved after stirring for 15 minutes.

Then, the organic compound was extracted into EA (3×100 mL). The combined extracts were washed with water (2×200 mL, to remove NMP) and brine solution. The organic layer was dried over anhydrous MgSO₄, filtered and concentrated to obtain the crude white paste which was purified using an ISCO (220 g) column chromatography to afford 2.0 g (90%) of tert-butyl-4-[[4-[[(3S,3aR,6S,6aR)-6-acetoxy-2,3,3a,5,6,6a-hexahydrofuro[3,2-b]furane-3-yl]oxy]pyrimidine-2-yl]amino]piperidine-1-carboxylate as a white amorphous solid.

Step 5: Preparation of [(3S,3aR,6S,6aR)-3-[2-(4-piperidylamino)pyrimidin-4-yl]oxy-2,3,3a,5,6,6a-hexahydrofuro[3,2-b]furan-6-yl] acetate

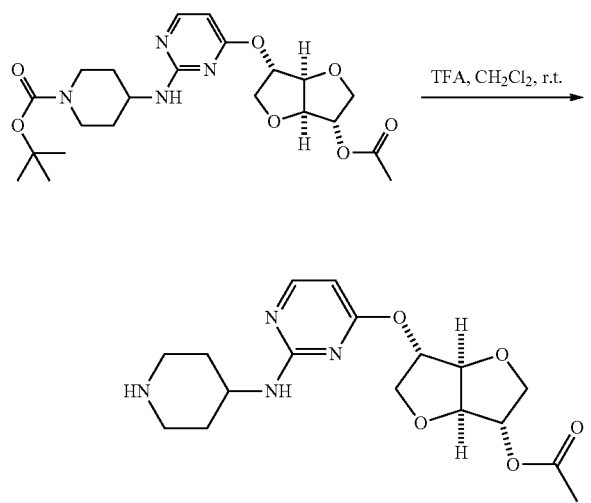

To a solution of tert-butyl-4-[[4-[[(3S,3aR,6S,6aR)-6-acetoxy-2,3,3a,5,6,6a-hexahydrofuro[3,2-b]furane-3-yl]oxy]pyrimidine-2-yl]amino]piperidine-1-carboxylate (2.0 g, 4.3 mmol) in dichloromethane (40 mL) in a 100 mL 2-neck RB flask was added TFA (10 mL) at room temperature under an argon atmosphere. The resulting light brown solution was stirred for 5 h at room temperature by which time TLC analysis of the reaction mixture indicated the absence of starting material. The solvent was removed under vacuum and the residue was dissolved again in minimal amount of dichloromethane and diluted with hexanes.

Then, the solvent was removed under vacuum and the residue was dried under high vacuum to obtain 3.5 g (more than theoretical yield) of [(3S,3aR,6S,6aR)-3-[2-(4-piperidylamino)pyrimidin-4-yl]oxy-2,3,3a,5,6,6a-hexahydrofuro[3,2-b]furan-6-yl] acetate as a viscous light brown oil.

Step 6: Preparation of [(3S,3aR,6S,6aR)-3-[2-[(1-methylsulfonyl-4-piperidyl)amino]pyrimidin-4-yl]oxy-2,3,3a,5,6,6a-hexahydrofuro[3,2-b]furan-6-yl] acetate

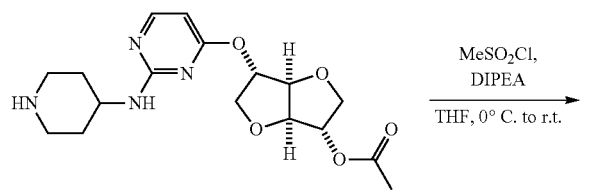

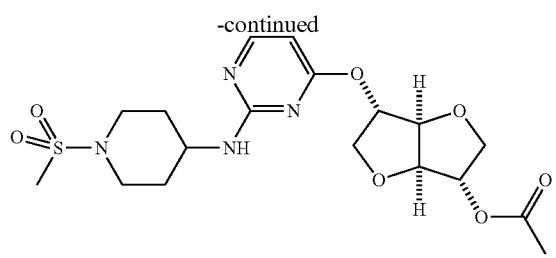

To a solution of [(3S,3aR,6S,6aR)-3-[2-(4-piperidylamino)pyrimidin-4-yl]oxy-2,3,3a,5,6,6a-hexahydrofuro[3,2-b]furan-6-yl] acetate (3.5 mmol) in THF (57 mL) in a 100 mL 2-neck RB flask were added methanesulfonyl chloride (618 mg, 418 uL, 5.4 mmol) followed by an large excess of DIPEA (4.39 g, 5.92 mL, 34 mmol) at 0-5° C. under an argon atmosphere. The resulting light brown solution was warmed to room temperature without removing the cooling bath. The reaction mixture was stirred for 6 h by which time TLC analysis of the mixture indicated the presence of a new spot.

Then, the reaction mixture was quenched with water and the organic compound was extracted into EA (2×100 mL). The combined extracts were washed with brine solution and dried over anhydrous MgSO₄. Filtration and concentration gave the crude product which completely dissolved in EA (~5 mL) under hot conditions and then diluted with hexanes (~10 mL). A precipitation developed at room temperature. After 15 h, the solids were collected by filtration and washed with EA. After air drying, 1.18 g of (76%) of [(3S,3aR,6S,6aR)-3-[2-[(1-methylsulfonyl-4-piperidyl)amino]pyrimidin-4-yl]oxy-2,3,3a,5,6,6a-hexahydrofuro[3,2-b]furan-6-yl] acetate was isolated as an off-white solid. ¹H-NMR (DMSO-d6): δ 8.05 (d, J=6.4 Hz, 1H), 7.02 (br, s, 1H), 6.02 (d, J=6.2 Hz, 1H), 5.32 (s, 1H), 5.12 (d, J=3.4 Hz, 1H), 4.68 (d, J=3.4 Hz, 1H), 4.54 (d, J=3.4 Hz, 1H), 4.06-3.71 (m, 5H), 3.6-3.5 (m, 2H), 2.92 (s, 3H), 2.9-2.81 (m, 2H), 2.03 (s, 3H), 2.01-1.89 (m, 2H), 1.6-1.45 (m, 2H). LC/MS calcd. for $C_{18}H_{26}N_4O_7S$ $[(M+H)^{+1}]$443, obsd. 443.

Example GG

Preparation of [(3S,3aR,6S,6aR)-3-[2-[(1-tolylsulfonyl-4-piperidvl)amino]pyrimidin-4-yl]oxy-2,3,3a,5,6,6a-hexahydrofuro[3,2-b]furan-6-yl] acetate

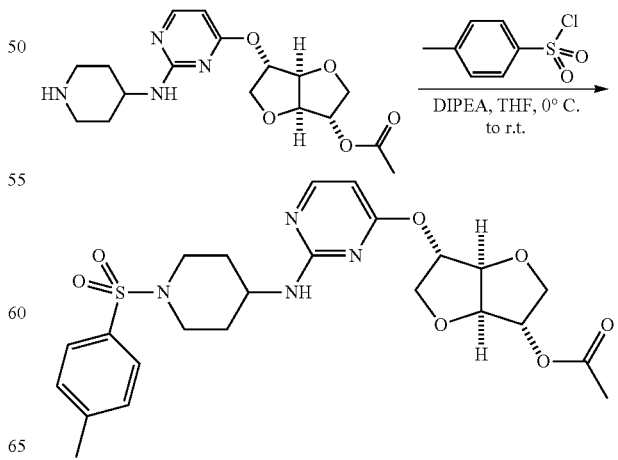

To a light brown solution of [(3S,3aR,6S,6aR)-3-[2-(4-piperidylamino)pyrimidin-4-yl]oxy-2,3,3a,5,6,6a-hexahydrofuro[3,2-b]furan-6-yl] acetate (0.5 mmol) in THF (5 mL) in a 25 mL 2-neck RB flask was added an excess of DIPEA (610 mg, 822 uL, 4.7 mmol) at 0-5° C. under an argon atmosphere. After 5 minutes, the cooling bath was removed and the light brown mixture was warmed to room temperature. After 30 minutes stirring at room temperature, solid p-toluenesulfonyl chloride (142 mg, 0.75 mmol) was added. It slowly became a clear and light brown solution and it was stirred for 15 h by which time TLC analysis (1:1, Hex:EA) of the reaction mixture indicated the presence of new spot.

The reaction mixture was quenched with water and the organic compound was extracted into EA (2×50 mL). The combined extracts were washed with brine solution and dried over anhydrous $MgSO_4$. Filtration and concentration gave the crude product which was purified using an ISCO (80 g) column chromatography to afford 220 mg (85%) of [(3S,3aR,6S,6aR)-3-[2-[(1-tolylsulfonyl-4-piperidyl)amino]pyrimidin-4-yl]oxy-2,3,3a,5,6,6a-hexahydrofuro[3,2-b]furan-6-yl] acetate as an off-white solid. $^1$H-NMR (CDCl$_3$): δ 8.0 (d, J=6.3 Hz, 1H), 7.75 (d, J=8.2 Hz, 2H), 7.45 (d, J=8.0 Hz, 2H), 6.02 (d, J=6.4 Hz, 1H), 5.35 (s, 1H), 5.25 (s, 1H), 4.75 (s, 1H), 4.65 (s, 1H), 4.06-3.81 (m, 5H), 3.8-3.62 (m, 4H), 2.65-2.43 (m, 5H), 2.14 (s, 3H), 1.7-1.55 (m, 2H). LC/MS calcd. for $C_{24}H_{30}N_4O_7S$ [(M+H)$^+$] 519, obsd. 519.

Example HH

Preparation of [(3S,3aR,6S,6aR)-3-[2-[[1-(2,2-dimethylpropanoyl)-4-piperidyl]amino]pyrimidin-4-yl]oxy-2,3,3a,5,6,6a-hexahydrofuro[3,2-b]furan-6-yl] acetate

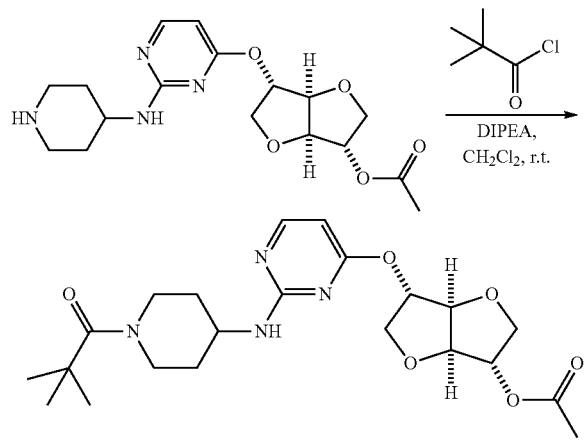

To a solution of [(3S,3aR,6S,6aR)-3-[2-(4-piperidylamino)pyrimidin-4-yl]oxy-2,3,3a,5,6,6a-hexahydrofuro[3,2-b]furan-6-yl] acetate (218 mg, 0.6 mmol) in dichloromethane (10 mL) in a 25 mL 2-neck RB flask were added first an excess of DIPEA (387 mg, 523 uL, 3.0 mmol) and then pivaloyl chloride (85 mg, 0.7 mmol) at room temperature under an argon atmosphere. The resulting light yellow solution was stirred for 15 h at room temperature by which time TLC analysis of the reaction mixture indicated the presence of a new spot. Then, the reaction mixture was diluted with water and dichloromethane and the two layers separated. The aqueous layer was extracted with dichloromethane (50 mL).

The combined extracts were washed with brine solution. The organic layer was dried over anhydrous MgSO$_4$, filtered and concentrated to obtain the crude oil which was purified using an ISCO (40 g) column chromatography to obtain 111 mg (41%) of [(3S,3aR,6S,6aR)-3-[2-[[1-(2,2-dimethylpropanoyl)-4-piperidyl]amino]pyrimidin-4-yl]oxy-2,3,3a,5,6,6a-hexahydrofuro[3,2-b]furan-6-yl] acetate as a white solid. $^1$H-NMR (CDCl$_3$): δ 8.15 (d, J=6.5 Hz, 1H), 6.05 (d, J=6.6 Hz, 1H), 5.48 (s, 1H), 5.23 (d, J=3.4 Hz, 1H), 4.74 (d, J=3.4 Hz, 1H), 4.6 (d, J=3.5 Hz, 1H), 4.4-4.28 (m, 2H), 4.12-3.81 (m, 5H), 3.18-3.05 (m, 2H), 2.24-2.02 (m, 5H), 1.5-1.25 (m, 11H). LC/MS calcd. for $C_{22}H_{32}N_4O_6$ [(M+H)$^+$] 449, obsd. 449.

Example II

Preparation of [(3S,3aR,6S,6aR)-3-[2-[(4-fluorophenyl)methylamino]pyrimidin-4-yl]oxy-2,3,3a,5,6,6a-hexahydrofuro[3,2-b]furan-6-yl] acetate

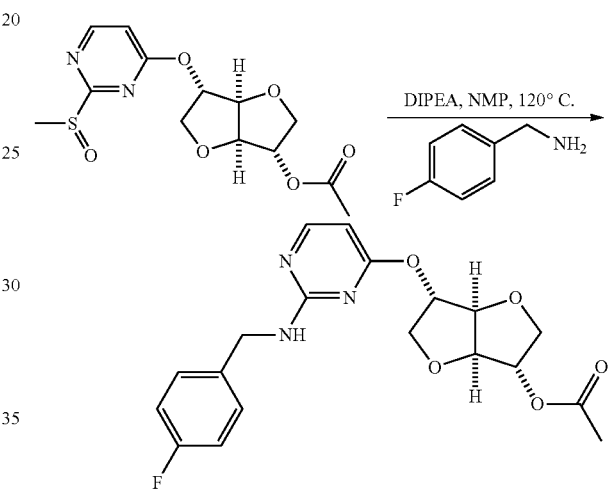

To a solution of [(3S,3aR,6S,6aR)-3-(2-methylsulfinylpyrimidin-4-yl)oxy-2,3,3a,5,6,6a-hexahydrofuro[3,2-b]furan-3-yl] acetate (240 mg, 0.73 mmol) in NMP (5 mL) in a 25 mL 2-neck RB flask were added 4-fluorobenzylamine (188 mg, 1.5 mmol) followed by DIPEA (194 mg, 261 uL, 1.5 mmol) at room temperature under an argon atmosphere. The resulting colorless solution was heated to 120° C. (bath temperature) and stirred for 2 h. During this period, it slowly turned into a light brown solution. LCMS analysis of the reaction mixture indicated the presence of a new peak and disappearance of the starting material peak.

Then, the reaction mixture was cooled to room temperature and diluted with water and then, the organic compound was extracted into EA (2×50 mL). The combined extracts were washed with water (2×100 mL, to remove NMP) and brine solution. The organic layer was dried over anhydrous MgSO$_4$, filtered and concentrated to obtain a crude white paste that was purified using an ISCO (40 g) column chromatography to isolate 210 mg (74%) of [(3S,3aR,6S,6aR)-3-[2-[(4-fluorophenyl)methylamino]pyrimidin-4-yl]oxy-2,3,3a,5,6,6a-hexahydrofuro[3,2-b]furan-6-yl] acetate as a light brown paste. $^1$H-NMR (CDCl$_3$): δ 8.13 (d, J=6.5 Hz, 1H), 7.42-7.23 (m, 2H), 7.12-6.98 (m, 2H), 6.11 (d, J=6.4 Hz, 1H), 5.48 (s, 1H), 5.23 (d, J=3.4 Hz, 1H), 4.69 (d, J=3.9 Hz, 1H), 4.61 (d, J=3.5 Hz, 1H), 4.51-4.50 (m, 2H), 4.12-3.82 (m, 4H), 2.05 (s, 3H). LC/MS calcd. for $C_{19}H_{20}FN_3O_5$ [(M+H)$^+$] 390, obsd. 390.

Example JJ

Synthesis of [(3S,3aR,6S,6aR)-3-[2-[(1-methylsulfonyl-4-piperidyl)amino]pyrimidin-4-yl]oxy-2,3,3a,5,6,6a-hexahydrofuro[3,2-b]furan-6-yl] benzoate

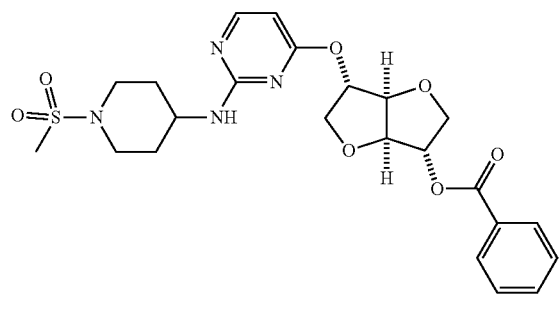 [SMILES: CS(=O)(=O)N1CCC(Nc2nccc(O[C@H]3CO[C@H]4[C@@H]3OC[C@@H]4OC(=O)c3ccccc3)n2)CC1]

Step 1: Preparation of [(3S,3aR,6S,6aR)-3-(2-methylsulfanylpyrimidin-4-yl)oxy-2,3,3a,5,6,6a-hexahydrofuro[3,2-b]furan-6-yl] benzoate

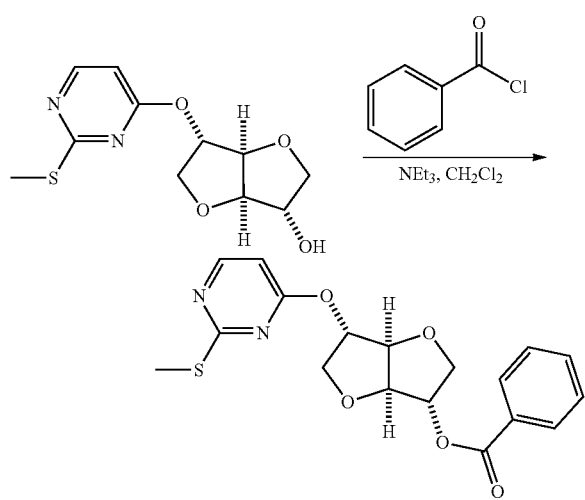

To a colorless solution of (3S,3aR,6S,6aR)-6-(2-methylsulfanylpyrimidin-4-yl)oxy-2,3,3a,5,6,6a-hexahydrofuro[3,2-b]furan-3-ol (1.72 g, 6.4 mmol) in dichloromethane (60 mL) in a 100 mL 2-neck RB flask were added first benzoyl chloride (1.4 g, 1.16 mL, 10 mmol) followed by an excess of triethylamine (2.02 g, 2.78 mL, 20 mmol) at 0-5° C. under an argon atmosphere. The resulting colorless solution was warmed to room temperature without removing cooling bath and then stirred for 15 h at room temperature by which time TLC (1:1, Hex:EA) analysis of the reaction mixture indicated the appearance of a new spot.

Then, it was diluted with water and the organic compound was extracted into dichloromethane (2×100 mL). The combined organic extracts were washed with brine solution and dried over anhydrous $MgSO_4$. Filtration and concentration yielded a crude light brown oil that was purified using an ISCO (220 g) column chromatography to obtain 1.91 g (80%) of [(3S,3aR,6S,6aR)-3-(2-methylsulfanylpyrimidin-4-yl)oxy-2,3,3a,5,6,6a-hexahydrofuro[3,2-b]furan-6-yl] benzoate as a white paste.

Step 2: Preparation of [(3S,3aR,6S,6aR)-3-(2-methylsulfonylpyrimidin-4-yl)oxy-2,3,3a,5,6,6a-hexahydrofuro[3,2-b]furan-3-yl] benzoate

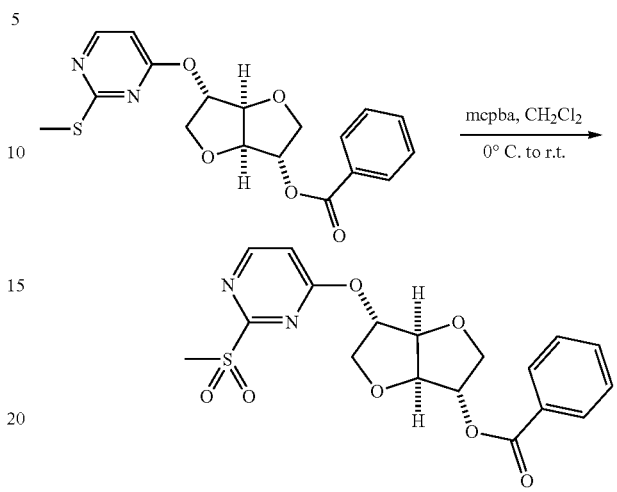

To a solution of [(3S,3aR,6S,6aR)-3-(2-methylsulfanylpyrimidin-4-yl)oxy-2,3,3a,5,6,6a-hexahydrofuro[3,2-b]furan-3-yl] benzoate (1.12 g, 3 mmol) in dichloromethane (40 mL) in a 100 mL 2-neck RB flask was added mcpba (1.38 g, 8 mmol, 77%) at 0-5° C. (ice+water) in one portion under an argon atmosphere. The resulting colorless solution was stirred for 4 h at 0° C. to r.t. (cooling bath was warmed to r.t.) by which time TLC analysis of the mixture indicated the presence of two polar spots and the disappearance of starting material.

Then, the reaction mixture was diluted with water and the two layers separated while aqueous layer extracted again with dichloromethane. The combined extracts were washed with saturated sodium bicarbonate solution (2×150 mL) followed by water and brine solution. The organic layer was dried over anhydrous $MgSO_4$, filtered and concentrated to obtain crude oil that was purified using an ISCO (220 g) column chromatography to obtain 644 mg (53%) of [(3S,3aR,6S,6aR)-3-(2-methylsulfonylpyrimidin-4-yl)oxy-2,3,3a,5,6,6a-hexahydrofuro[3,2-b]furan-3-yl] benzoate as a white solid.

Step 3: Preparation of tert-butyl-4-[[4-[[(3S,3aR,6S,6aR)-6-benzoyloxy-2,3,3a,5,6,6a-hexahydrofuro[3,2-b]furane-3-yl]oxy]pyrimidine-2-yl]amino]piperidine-1-carboxylate

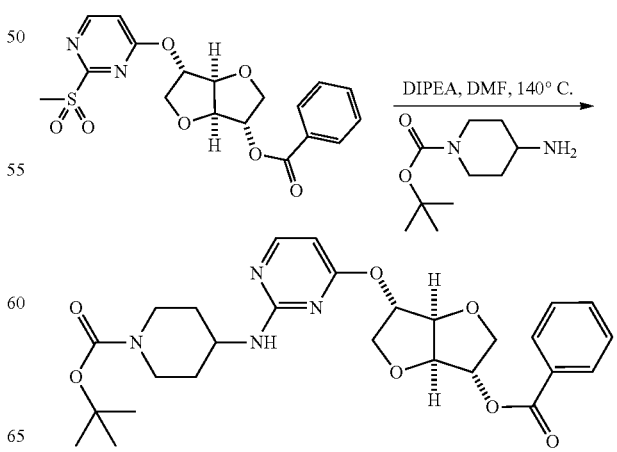

To a solution of [(3S,3aR,6S,6aR)-3-(2-methylsulfonylpyrimidin-4-yl)oxy-2,3,3a,5,6,6a-hexahydrofuro[3,2-b]furan-3-yl] benzoate (102 mg, 0.25 mmol) in DMF (3 mL) in a 25 mL sealed tube were added 4-aminopiperidine-1-carboxylic acid tert-butyl ester (103 mg, 0.5 mmol) followed by an excess of triethylamine (101 mg, 139 uL, 1.0 mmol) at room temperature under an argon atmosphere. The rubber septum was replaced with a screw cap and the light cloudy solution was heated to 140° C. (bath temperature).

Then, the reaction mixture was stirred for 3 h at this temperature by which time it turned into a brown solution. TLC (1:1, Hex:EA) analysis of the aliquot, which was hydrolyzed with water and EA indicated the presence of a new spot. The reaction mixture was cooled to room temperature and diluted with water. Then, the organic compound was extracted into EA (3×30 mL). The combined extracts were washed with water (2×100 mL) and brine solution. The organic layer was dried over anhydrous MgSO$_4$, filtered and concentrated to obtain the crude white compound which was purified using an ISCO (120 g) column chromatography to obtain 117 mg (88%) of tert-butyl-4-[[4-[[(3S,3aR,6S,6aR)-6-benzoyloxy-2,3,3a,5,6,6a-hexahydrofuro[3,2-b]furane-3-yl]oxy]pyrimidine-2-yl]amino]piperidine-1-carboxylate as a white amorphous solid.

Step 4: Preparation of [(3S,3aR,6S,6aR)-3-[2-(4-piperidylamino)pyrimidin-4-yl]oxy-2,3,3a,5,6,6a-hexahydrofuro[3,2-b]furan-6-yl] benzoate

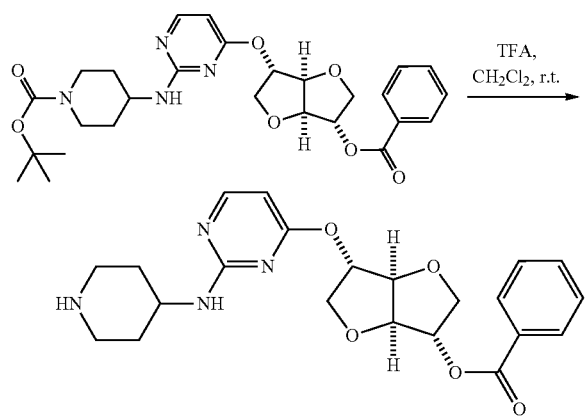

To a solution of tert-butyl-4-[[4-[[(3S,3aR,6S,6aR)-6-benzoyloxy-2,3,3a,5,6,6a-hexahydrofuro[3,2-b]furane-3-yl]oxy]pyrimidine-2-yl]amino]piperidine-1-carboxylate (117 mg, 0.22 mmol) in dichloromethane (10 mL) in a 50 mL 2-neck RB flask was added TFA (1 mL) at room temperature under an argon atmosphere. The resulting light yellow solution was stirred for 4 h at room temperature by which time TLC analysis of the reaction mixture indicated the absence of the starting material.

Then, the solvent was removed under vacuum and the residue was dissolved again in minimal amount of dichloromethane and diluted with toluene. The solvent was removed under vacuum and the residue was dried under high vacuum to obtain the crude [(3S,3aR,6S,6aR)-3-[2-(4-piperidylamino)pyrimidin-4-yl]oxy-2,3,3a,5,6,6a-hexahydrofuro[3,2-b]furan-6-yl] benzoate as a viscous light brown oil.

Step 5: Preparation of [(3S,3aR,6S,6aR)-3-[2-[(1-methylsulfonyl-4-piperidyl)amino]pyrimidin-4-yl]oxy-2,3,3a,5,6,6a-hexahydrofuro[3,2-b]furan-6-yl]benzoate

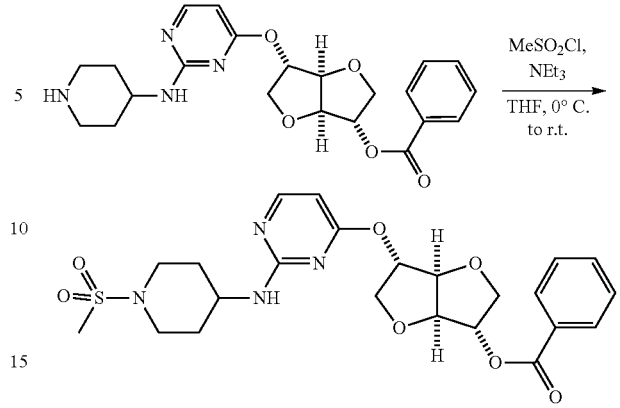

To a solution of [(3S,3aR,6S,6aR)-3-[2-(4-piperidylamino)pyrimidin-4-yl]oxy-2,3,3a,5,6,6a-hexahydrofuro[3,2-b]furan-6-yl] benzoate (0.22 mmol) in THF (10 mL) in a 50 mL 2-neck RB flask were added methanesulfonyl chloride (38 mg, 26 uL, 0.33 mmol) followed by a large excess of triethylamine (101 mg, 139 uL, 1.0 mmol) at 0-5° C. under an argon atmosphere. Within 5 minutes, a white precipitate formed which was warmed to room temperature without removing the cooling bath and the reaction mixture was stirred for 15 h at room temperature.

Then, the reaction mixture was diluted with water and the organic compound was extracted into EA (2×20 mL). The combined extracts were washed with brine solution and dried over anhydrous MgSO$_4$. Filtration and concentration produced a crude product that was purified using an ISCO (80 g) column chromatography to afford 89 mg (80%) of [(3S,3aR,6S,6aR)-3-[2-[(1-methylsulfonyl-4-piperidyl)amino]pyrimidin-4-yl]oxy-2,3,3a,5,6,6a-hexahydrofuro[3,2-b]furan-6-yl] benzoate as a white solid. $^1$H-NMR (DMSO-d6): δ 8.06 (d, J=5.6 Hz, 1H), 7.98 (dd, J=7.8, 1.1 Hz, 2H), 7.69 (m, 1H), 7.54 (t, J=6.7 Hz, 2H), 7.02 (br, d, 1H), 6.05 (d, J=2.8 Hz, 1H), 5.45 (s, 1H), 5.34 (d, J=2.8 Hz, 1H), 4.79-4.77 (m, 2H), 4.07-4.05 (m, 2H), 4.02 (d, J=10.1 Hz, 1H), 3.96-3.95 (m, 1H), 3.82-3.75 (m, 1H), 3.54-3.52 (m, 2H), 2.92-2.84 (m, 5H), 1.95-1.93 (m, 2H), 1.55-1.53 (m, 2H). LC/MS calcd. for $C_{23}H_{28}N_4O_7S$ [(M+H)$^+$] 505, obsd. 505.

Example KK

Preparation of [(3S,3aR,6S,6aR)-3-hydroxy-2,3,3a,5,6,6a-hexahydrofuro[3,2-b]furan-6-yl] 5-bromo-2-methylsulfanyl-pyrimidine-4-carboxylate

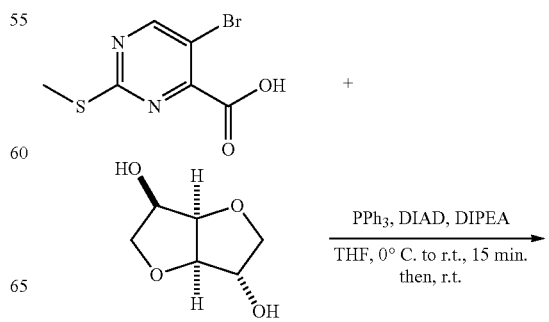

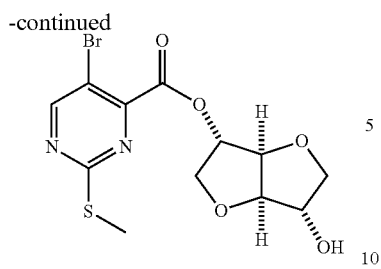

To a solution of triphenylphosphine (577 mg, 2.2 mmol) in THF (15 mL) in a 100 mL 2-neck RB flask was added di-isopropylazodicarboxylate (445 mg, 433 uL, 2.2 mmol) at 0-5° C. (ice+water) for 5 minutes under an argon atmosphere. The resulting light yellow suspension was stirred for 10-15 minutes at this temperature. Then, a solution of 5-bromo-2-methylsulfanyl-pyrimidine-4-carboxylic acid (360 mg, 1.45 mmol) in THF (12 mL) was added drop-wise over 3 minutes. After 2 minutes, the cooling bath was removed to allow the reaction mixture to warm to room temperature and it was stirred for 10-15 minutes.

Then, a solution of isosorbide (254 mg, 1.74 mmol) in THF (10 mL) was slowly added followed by the neat DIPEA (284 mg, 383 uL, 2.2 mmol) at room temperature. It became a clear solution within 5 minutes after which it was stirred for 36 h. TLC (1:1, Hex:EA) analysis of the reaction mixture indicated the appearance of a new spot. The solvent was removed under vacuum and the crude residue was purified using an ISCO (220 g) column chromatography to obtain 409 mg (75%) of [(3S,3aR,6S,6aR)-3-hydroxy-2,3,3a,5,6,6a-hexahydrofuro[3,2-b]furan-6-yl] 5-bromo-2-methylsulfanyl-pyrimidine-4-carboxylate as a light yellow solid. $^1$H-NMR (DMSO-d6): δ 8.86 (s, 1H), 5.37 (s, 1H), 5.28 (d, J=3.9 Hz, 1H), 4.65 (d, J=3.9 Hz, 1H), 4.44 (d, J=2.8 Hz, 1H), 4.12 (br, s, 1H), 3.94 (d, J=1.7 Hz, 1H), 3.77 (dd, J=8.4, 2.8 Hz, 1H), 3.71 (d, J=8.4 Hz, 1H), 3.31 (d, J=12.9S Hz, 1H), 2.53 (s, 3H). LC/MS calcd. for $C_{12}H_{13}BrN_2O_5S$ $[(M+H)^{+}]$ 377, obsd. 377.

Example LL

Preparation of [(3S,3aR,6S,6aR)-3-hydroxy-2,3,3a,5,6,6a-hexahydrofuro[3,2-b]furan-6-yl] (2S)-2-[(2-chloro-6-methyl-benzoyl)amino]-3-[4-[(2,6 dichlorobenzoyl)amino]phenyl]propanoate

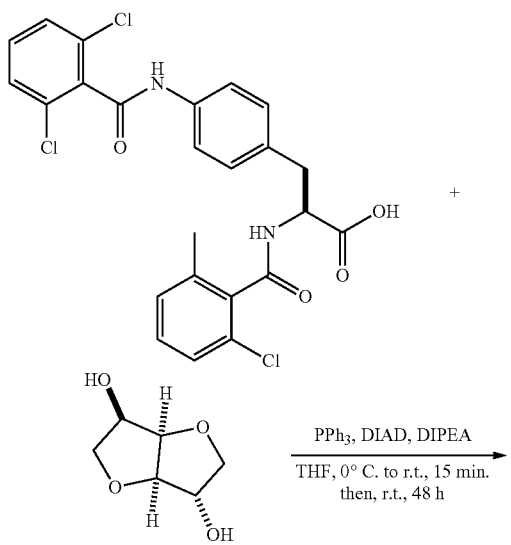

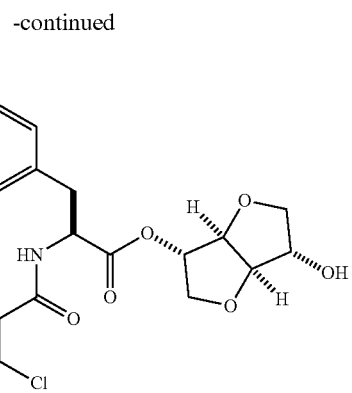

To a solution of triphenylphosphine (393 mg, 1.5 mmol) in THF (5 mL) in a 25 mL 2-neck RB flask was added di-isopropylazodicarboxylate (303 mg, 295 uL, 1.5 mmol) at 0-5° C. (ice+water) for 2-3 minutes under an argon atmosphere. The resulting light yellow suspension was stirred for 10 minutes at this temperature. Then, a solution of (2S)-2-[(2-chloro-5-methyl-benzoyl)amino]-3-[4-[(2,6-dichlorobenzoyl)amino]phenyl]propanoic acid (200 mg, 0.5 mmol) (for preparation, see WO1999/10312) in THF (3 mL) was added drop-wise for 5 minutes. After 2 minutes, the cooling bath was removed to allow the reaction mixture to warm to room temperature where it was stirred for 10 minutes.

Then, a solution of isosorbide (88 mg, 0.6 mmol) in THF (2 mL) was added slowly followed by the neat DIPEA (194 mg, 261 uL, 1.5 mmol) at room temperature. The resulting orange color suspension was stirred for 48 h. During this period, it turned to a light yellow solution and after 48 h, TLC analysis of the reaction mixture indicated the appearance of a new and less polar spot, but it was close to triphenylphosphine oxide.

Then, the solvent was removed under vacuum and the crude residue was purified using an ISCO (120 g) column chromatography to obtain 284 mg (90%) of [(3S,3aR,6S, 6aR)-3-hydroxy-2,3,3a,5,6,6a-hexahydrofuro[3,2-b]furan-6-yl] (2S)-2-[(2-chloro-6-methyl-benzoyl)amino]-3-[4-[(2, 6-dichlorobenzoyl)amino]phenyl]propanoate as a white solid. $^1$H-NMR (CDCl$_3$): δ 7.63 (d, J=8.6 Hz, 2H), 7.4-7.2 (m, 7H), 7.1-7.02 (m, 1H), 6.25 (d, J=7.8 Hz, 1H), 5.25-5.1 (m, 3H), 4.55 (d, J=3.4 Hz, 2H), 4.0-3.92 (m, 4H), 3.2 (d, J=7.5 Hz, 2H), 2.05 (s, 3H). LC/MS calcd. for $C_{30}H_{27}Cl_3N_2O_7$ $[(M+H)^{+}]$ 633, obsd. 633.

Example MM

Preparation of [(3S,3aR,6S,6aR)-3-acetoxy-2,3,3a,5,6,6a-hexahydrofuro[3,2-b]furan-6-yl] (2S)-2-[(2-chloro-6-methyl-benzoyl)amino]-3-[4-[(2,6-dichlorobenzoyl)amino] phenyl]propanoate

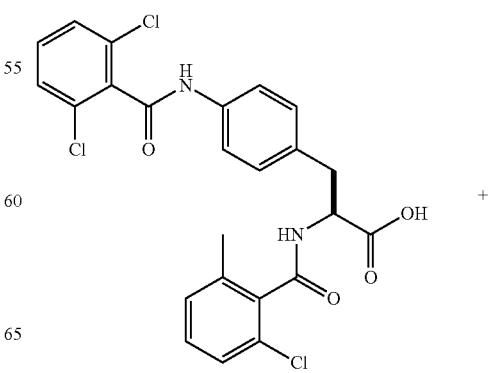

-continued

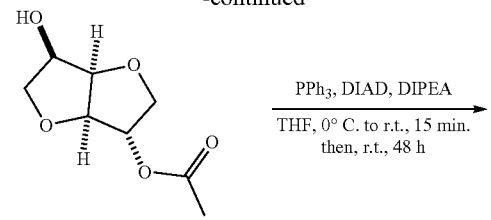

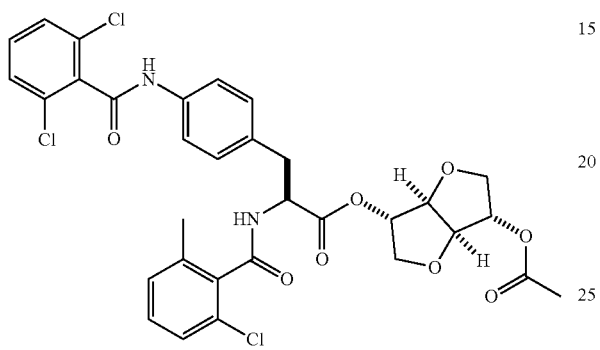

To a solution of triphenylphosphine (1.57 g, 6.0 mmol) in THF (50 mL) in a 250 mL 3-neck RB flask was added di-isopropylazodicarboxylate (1.21 g, 1.18 mL, 6.0 mmol) at 0-5° C. (ice+water) for 4-5 minutes under an argon atmosphere. The resulting light yellow suspension was stirred for 10 minutes at this temperature. Then, a solution of (2S)-2-[(2-chloro-5-methyl-benzoyl)amino]-3-[4-[(2,6-dichlorobenzoyl)amino]phenyl]propanoic acid (2.02 g, 4.0 mmol) (for preparation, see WO1999/10312) in THF (50 mL) was added drop-wise for 5 minutes. After 2 minutes, the cooling bath was removed to allow the reaction mixture to warm to room temperature where it was stirred for 10 minutes.

Then, a solution of isosorbide 2-acetate (for preparation, see reference Synthesis, 1987, 174) (903 mg, 4.8 mmol) in THF (40 mL) was added slowly followed by the neat DIPEA (775 mg, 1.05 mL, 6.0 mmol) at room temperature. The resulting orange color solution was stirred for 48 h by which time it turned to a clear light brown solution and TLC analysis of the reaction mixture indicated the appearance of a new spot. Then, the solvent was removed under vacuum and the crude residue was purified using an ISCO (220 g) column chromatography to obtain 2.16 g (80%) of [(3S,3aR,6S,6aR)-3-acetoxy-2,3,3a,5,6,6a-hexahydrofuro[3,2-b]furan-6-yl] (2S)-2-[(2-chloro-6-methyl-benzoyl)amino]-3-[4-[(2,6-dichlorobenzoyl)amino]phenyl]propanoate as a white solid. $^1$H-NMR (CDCl$_3$): δ 7.65 (d, J=8.5 Hz, 2H), 7.4-7.2 (m, 7H), 7.1-7.02 (m, 1H), 6.24 (d, J=7.8 Hz, 1H), 5.25-5.1 (m, 2H), 4.6 (d, J=3.4 Hz, 2H), 4.0-3.92 (m, 4H), 3.2 (d, J=7.5 Hz, 2H), 2.15 (s, 3H), 2.05 (s, 3H). LC/MS calcd. for $C_{32}H_{29}Cl_3N_2O_8$ [(M+H)$^+$] 675, obsd. 675.

Example NN

Preparation of [(3S,3aR,6S,6aR)-3-benzyloxy-2,3,3a,5,6,6a-hexahydrofuro[3,2-b]furan-6-yl](2S)-2-[(2-chloro-6-methyl-benzoyl)amino]-3-[4-[(2,6-dichlorobenzoyl)amino]phenyl]propanoate

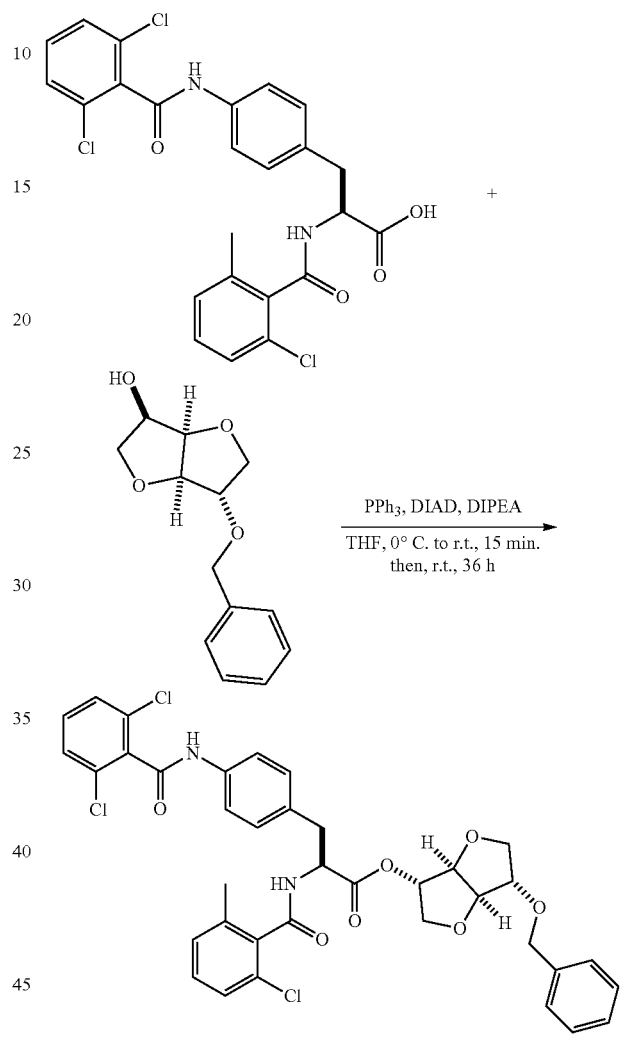

To a solution of triphenylphosphine (1.18 g, 4.5 mmol) in THF (3 mL) in a 250 mL 3-necked RB flask was added di-isopropylazodicarboxylate (910 mg, 886 uL, 4.5 mmol) at 0-5° C. (ice+water) for 4-5 minutes under an argon atmosphere. The resulting light yellow suspension was stirred for 10 minutes at this temperature. Then, a solution of (2S)-2-[(2-chloro-5-methyl-benzoyl)amino]-3-[4-[(2,6-dichlorobenzoyl)amino]phenyl]propanoic acid (1.52 g, 3.0 mmol) (for preparation, see WO1999/10312) in THF (30 mL) was added drop-wise for 5 minutes. After 2 minutes, the cooling bath was removed to allow the reaction mixture to warm to room temperature where it was stirred for 10 minutes.

Then, a solution of isosorbide 2-benzyl ether (851 mg, 3.6 mmol) in THF (20 mL) was added slowly followed by the neat DIPEA (582 mg, 784 uL, 4.5 mmol) at room temperature. The resulting light brown suspension was stirred for 36 h by this time it gave a clear light brown solution and TLC analysis of the reaction mixture indicated the appearance of a new and less polar spot. Then, the reaction mixture was diluted with water (100 mL) and the organic compound was extracted into EA (75 mL). The organic extracts were washed with 4:1 ratio of water and methanol mixture to remove the triphenylphosphine oxide. The organic layer was washed with brine solution and dried over anhydrous MgSO$_4$, filtration and concentration gave the crude amorphous solid which was purified using an ISCO (220 g) column chromatography to afford 1.86 g (86%) of [(3S,3aR,6S,6aR)-3-benzyloxy-2,3,3a,5,6,6a-hexahydrofuro[3,2-b]furan-6-yl] (2S)-2-[(2-chloro-6-methyl-benzoyl)amino]-3-[4-[(2,6-dichlorobenzoyl)amino]phenyl]propanoate as a white solid. $^1$H-NMR (CDCl$_3$): δ 7.51 (d, J=8.6 Hz, 2H), 7.4-7.2 (m, 12H), 7.1-7.02 (m, 1H), 6.25 (d, J=7.8 Hz, 1H), 5.25-5.15 (m, 2H), 4.51-4.49 (m, 4H), 4.1 (d, J=3.4 Hz, 1H), 4.0-3.75 (m, 4H), 3.25-3.2 (m, 1H), 2.2 (s, 3H). LC/MS calcd. for C$_{37}$H$_{33}$Cl$_3$N$_2$O$_7$ [(M+H)$^+$] 723, obsd. 723.

Example OO

Preparation of [(3S,3aR,6S,6aR)-3-acetoxy-2,3,3a,5,6,6a-hexahydrofuro[3,2-b]furan-6-yl] (2S)-2-[(2-chloro-6-methyl-benzoyl)amino]-3-[4-(1,3,4-trimethyl-2,6-dioxo-pyrimidin-5-yl)phenyl]propanoate

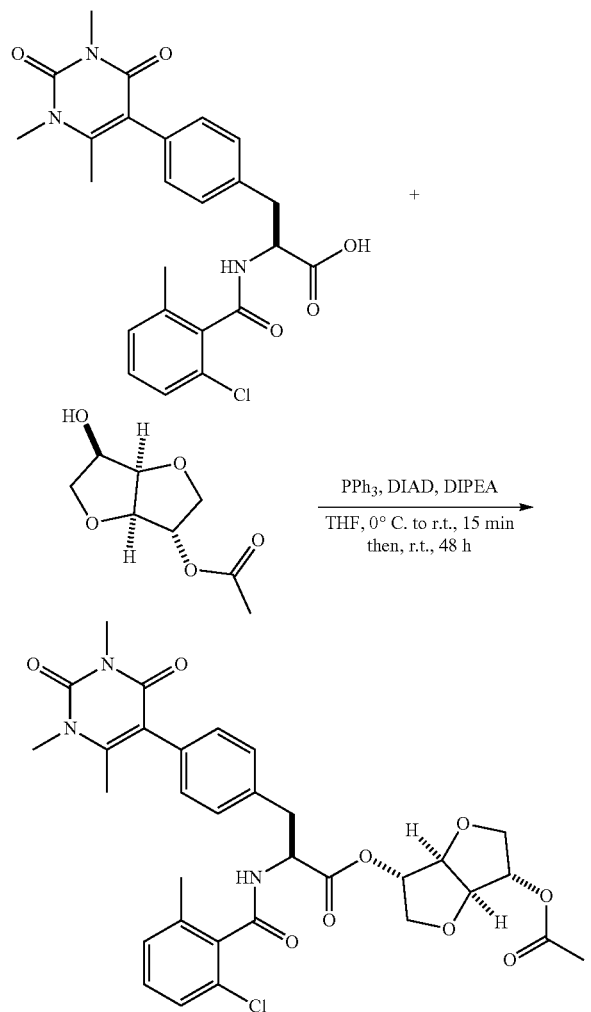

To a solution of triphenylphosphine (1.97 g, 7.5 mmol) in THF (50 mL) in a 250 mL 3-neck RB flask was added di-isopropylazodicarboxylate (1.52 g, 1.48 mL, 7.5 mmol) at 0-5° C. (ice+water) for 5 minutes under an argon atmosphere. The resulting light yellow suspension was stirred for 10-15 minutes at this temperature. Then, a solution of (2S)-2-[(2-chloro-6-methyl-benzoyl)amino]-3-[4-(1,3,4-trimethyl-2,6-dioxo-pyrimidin-5-yl)phenyl]propanoic acid (2.35 g, 5 mmol) (For preparation, see U.S. Ser. No. 00/638, 0387B 1) in THF (70 mL, heated to dissolve) was added drop-wise for 5 minutes. After 2 minutes, the cooling bath was removed to allow the reaction mixture to warm to room temperature where it was stirred for 10-15 minutes.

Then, a solution of isosorbide 2-acetate (1.13 g, 5 mmol) in THF (40 mL) was added followed by the neat DIPEA (969 mg, 1.3 mL, 7.5 mmol) at room temperature. The resulting light yellow solution was stirred for 48 h by which time it turned to a clear colorless solution and TLC analysis of the reaction mixture indicated the appearance of a new spot. Then, the solvent was removed under vacuum and the crude residue was purified using an ISCO (220 g) column chromatography to obtain 2.53 g (79%) of [(3S,3aR,6S,6aR)-3-acetoxy-2,3,3a,5,6,6a-hexahydrofuro[3,2-b]furan-6-yl] (2S)-2-[(2-chloro-6-methyl-benzoyl)amino]-3-[4-(1,3,4-trimethyl-2,6-dioxo-pyrimidin-5-yl)phenyl]propanoate as a white solid. $^1$H-NMR (DMSO-d6): δ 9.08 (d, J=7.8 Hz, 1H), 7.34 (d, J=7.8 Hz, 2H), 7.28-7.24 (m, 2H), 7.17 (d, J=6.6 Hz, 1H), 7.12 (d, J=7.8 Hz, 2H), 5.13 (d, J=3.6 Hz, 1H), 5.04 (d, J=3.4 Hz, 1H), 4.779-4.76 (m, 1H), 4.49 (d, J=4.1 Hz, 1H), 4.46 (d, J=3.9 Hz, 1H), 3.95 (dd, J=10.8, 3.6 Hz, 1H), 3.91 (dd, J=10.8, 3.6 Hz, 1H), 3.85 (t, J=9.6 Hz, 1H), 3.41 (s, 3H), 3.32 (d, J=13.8 Hz, 1H), 3.22 (s, 3H), 3.21 (dd, J=13.4, 5.4 Hz, 1H), 3.01 (dd, J=13.8, 10.2 Hz, 1H), 2.11 (s, 3H), 2.06 (s, 3H), 2.02 (s, 3H). LC/MS calcd. for C$_{32}$H$_{34}$ClN$_3$O$_9$ [(M+H)$^+$] 640, obsd. 640.

Example PP

Preparation of [(3S,3aR,6S,6aR)-3-hydroxy-2,3,3a,5,6,6a-hexahydrofuro[3,2-b]furan-6-yl] (2S)-2-[(2-chloro-6-methyl-benzoyl)amino]-3-[4-(1,3,4-trimethyl-2,6-dioxo-pyrimidin-5-yl)phenyl]propanoate

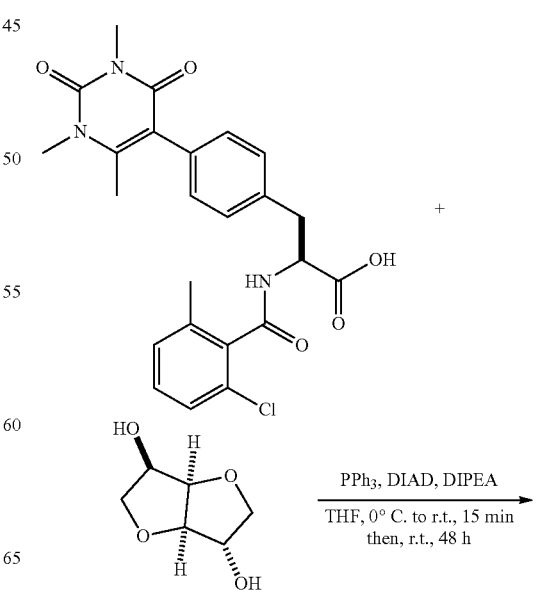

-continued

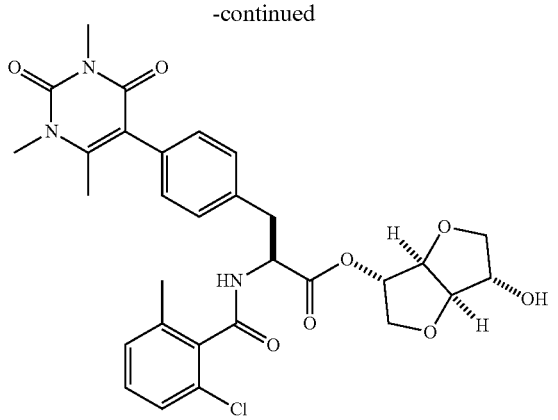

To a solution of triphenylphosphine (787 mg, 3 mmol) in THF (20 mL) in a 100 mL 3-neck RB flask was added di-isopropylazodicarboxylate (606 mg, 591 uL, 3 mmol) at 0-5° C. (ice+water) for 5 minutes under an argon atmosphere. The resulting light yellow suspension was stirred for 10-15 minutes at this temperature. Then, a solution of (2S)-2-[(2-chloro-6-methyl-benzoyl)amino]-3-[4-(1,3,4-trimethyl-2,6-dioxo-pyrimidin-5-yl)phenyl]propanoic acid (940 mg, 2 mmol) (For preparation, see U.S. Ser. No. 00/638,0387B 1) in THF (30 mL, heated to dissolve) was added drop-wise for 5 minutes. After 2 minutes, the cooling bath was removed to allow the reaction mixture to warm to room temperature where it was stirred for 10-15 minutes.

Then, a solution of isosorbide (351 mg, 2.4 mmol) in THF (15 mL) was added followed by the neat DIPEA (388 mg, 523 uL, 3 mmol) at room temperature. The resulting light yellow solution was stirred for 48 h by which time it turned to a clear colorless solution and TLC analysis of the reaction mixture indicated the appearance of a new spot. Then, the solvent was removed under vacuum and the crude residue was dissolved in ethyl acetate at hot condition and then diluted with hexanes. The resulting solution was stored in the freezer for 15 h. The white solids were collected by filtration and washed with hexanes. This solid residue (1.5 g) was then purified using an ISCO (80 g) column chromatography to obtain 950 mg (80%) of [(3S,3aR,6S,6aR)-3-hydroxy-2,3,3a,5,6,6a-hexahydrofuro[3,2-b]furan-6-yl] (2S)-2-[(2-chloro-6-methyl-benzoyl)amino]-3-[4-(1,3,4-trimethyl-2,6-dioxo-pyrimidin-5-yl)phenyl]propanoate as a white solid. $^1$H-NMR (DMSO-d6): δ 9.07 (d, J=7.8 Hz, 1H), 7.33 (d, J=7.3 Hz, 2H), 7.28-7.24 (m, 2H), 7.16 (d, J=6.6 Hz, 1H), 7.11 (d, J=7.8 Hz, 2H), 5.25 (d, J=4.2 Hz, 1H), 5.09 (d, J=3.6 Hz, 1H), 4.82-4.79 (m, 1H), 4.45 (d, J=3.6 Hz, 1H), 4.36 (d, J=3.6 Hz, 1H), 4.1 (br, s, 1H), 3.88 (dd, J=11.4, 4.2 Hz, 1H), 3.79 (d, J=10.8 Hz, 1H), 3.73 (dd, J=8.9, 2.9 Hz, 1H), 3.67 (d, J=9.6 Hz, 1H), 3.41 (s, 3H), 3.33 (s, 3H), 3.21 (dd, J=13.4, 5.4 Hz, 1H), 3.01 (dd, J=13.8, 10.2 Hz, 1H), 2.11 (s, 3H), 2.02 (s, 3H). LC/MS calcd. for $C_{30}H_{32}ClN_3O_8$ [(M+H)$^+$] 598, obsd. 598.

Example QQ: Macrophage Migration Inhibitory Factor (MIF) as a Drug Target Assay Conditions a) PBMC Isolation:
Heparinized blood (10 ml) was diluted with equal volume of phosphate buffer saline (PBS). To the Ficoll solution (5 ml) add 5 ml of blood:PBS mixture and centrifuge at 1600 rpm for 30 minutes. Take the buffy coat and wash with PBS at 1200 rpm for 5 minutes (twice). After two washes with PBS, the PBMCs were washed with RPMI medium. The PBMC were counted and plated in 96 well plates (1×10$^6$ cells/well).

b) Expression of TNF-α and IL-1β in PBMCs in the Presence of MIF Inhibitors:
After overnight incubation, the cells were treated with different concentration of MIF inhibitors. After 6 hr, cells were treated with LPS (10 ng/ml) and LPS+MIF combination (10 ng/ml) and further incubated for overnight. PBMCs treated with 10 ng/ml of LPS and MIF in the presence of different concentrations of test compounds. After the incubation period, the supernatant were collected and human TNF-α and IL-1β were determined using the ELISA kits (R&D Systems).

TABLE 1

Inhibition and IC$_{50}$ values of TNF-α and IL-1β (LPS-stimulated PBMCs)

| Example | TNF-α IC$_{50}$ (uM) | IL-1β IC$_{50}$ (uM) |
|---|---|---|
| A | >1.0 | >1.0 |
| B | >10 | >10 |
| C | >0.5 | >0.5 |
| D | >10 | >10 |
| E | >0.5 | >0.5 |
| F | >10 | >10 |
| G | >0.1 | >0.1 |
| H | >10 | >10 |
| I | >0.5 | >0.5 |
| J | >0.1 | >0.1 |
| K | >0.1 | >0.1 |
| L | >1.0 | >1.0 |
| M | >0.5 | >0.5 |
| N | >0.1 | >10 |
| O | >0.1 | >10 |
| P | >10 | >10 |
| Q | >0.1 | >0.1 |
| R | >0.1 | >0.1 |
| S | >0.5 | >0.5 |

Example RR: EGFR as a Drug Target Assay Conditions

The IC50s of the compounds on EGFR activity were determined using the Luminescent ATP/ADP detection assay system. Briefly, the assay method measures ADP formed from EGFR kinase activity using luminescence derived from ATP-Luciferase detection system. Purified EGFR kinase was incubated with different concentrations of test compound in the kinase reaction buffer for 10 min. The reaction was stopped by depleting the unused ATP in the kinase reaction buffer using the depletion buffer for 40 min. The levels of ADP generated during the kinase reaction was detected by measuring the luminescence using the Luciferase system.

TABLE 2

Inhibitory effect of new compounds against EGFR kinase

| Example | EGFR IC$_{50}$ (uM) |
|---|---|
| T | >0.1 |
| U | >0.1 |
| V | Inactive |
| W | Inactive |
| X | >0.5 |
| Y | >1.0 |
| Z | >0.1 |

TABLE 2-continued

Inhibitory effect of new compounds against EGFR kinase

| Example | EGFR IC$_{50}$ (uM) |
|---|---|
| AA | >0.1 |
| BB | >0.5 |
| CC | >0.5 |
| DD | >0.1 |
| EE | >0.5 |
| FF | Inactive |
| GG | Inactive |
| HH | Inactive |
| II | Inactive |
| JJ | Inactive |
| KK | Inactive |

The compounds of the present invention are indicated for the inhibition, treatment or prevention of diseases mediated by MIF. MIF is a proinflammatory cytokine as a result several diseases mediated by MIF, e.g., inflammatory diseases, autoimmune diseases, neuropathic disorders, neurodegenerative diseases, cerebrovascular diseases, central nervous infections, traumatic diseases, colitis, heart and vascular conditions, liver and kidney diseases, respiratory diseases, allergic diseases, fibrotic diseases, metabolic disorders, infectious diseases, nephritis, sarcoidosis, transplantation, angiogenesis and cancers. Particularly arthritis, rheumatoid arthritis, osteoarthritis, psoriatic arthritis, lupus syndromes, systemic lupus erythematosus, sclerosis, multiple sclerosis, atherosclerosis, arteriosclerosis, systemic sclerosis, reactive arthritis, osteoporosis, brain disorders, Alzheimer's disease, colitis, inflammatory bowel disease, Crohn's disease, ulcerative disease, peptic ulceration, gastritis, oseophagitis, ischaemia, ischaemic heart disease, myocardial infraction, stroke, pulmonary hypertension, cirrhosis, chronic pulmonary disease, acute respiratory distress syndrome, asthma, asthma bronchitis, psoriasis, dermatomyositis, allergic rhinitis, diabetes, diabetic retinopathy, insulin-dependent diabetes, diabetes mellitus, obesity, endometriosis, testicular dysfunction, Lyme disease, viral diseases, parasitic diseases, fungal diseases, malaria, sepsis, septic shock, interstitial nephritis, angiogenesis, multiple myeloma, leukemia, non-small cell lung cancer, breast cancer, brain cancer, prostate cancer, pancreas cancer, skin cancer, metastatic bone disease and other forms of metastasis.

The compounds of the present invention are also indicated for the inhibition, treatment or prevention of diseases mediated by the EGFR. Diseases mediated by EGFR are primary or metastatic cancers, cervical cancer, solid tumors, tumor growth, lymphoma, B-cell lymphoma, T-cell lymphoma, premalignant conditions, benign tumors, benign dysproliferative disorders, renal carcinoma, esophageal cancer, stomach cancer, colon cancer, lung cancer, non-small cell lung cancer, melanoma, nasopharyngeal cancer, osteocarcinoma, ovarian cancer, breast cancer, brain cancer, renal carcinoma, bladder carcinoma, uterine cancer, prostate cancer, pancreas cancer, skin cancer, leukemia, tumor neovascularization, angiomas, myelodysplastic diseases, and metastatic bone disease and other forms of metastasis.

The compounds of the present invention are also useful for the inhibition, treatment or prevention of diseases that mediated by the kinases. Diseases mediated by kinases are primary or metastatic cancers, cervical cancer, solid tumors, tumor growth, lymphoma, B-cell lymphoma, T-cell lymphoma, premalignant conditions, benign tumors, benign dysproliferative disorders, renal carcinoma, esophageal cancer, stomach cancer, colon cancer, lung cancer, small cell lung cancer, melanoma, nasopharyngeal cancer, osteocarcinoma, ovarian cancer, breast cancer, renal carcinoma, bladder carcinoma, uterine cancer, prostate cancer, skin cancer, leukemia, tumor neovascularization, angiomas, myelodysplastic diseases.

The prodrug compounds of the alpha4 beta1 and alpha4 beta7 integrin antagonists of the present invention are indicated for the inhibition, treatment or prevention of diseases mediated by integrin receptors. Integrins, especially alpha4 beta1 and alpha4 beta7, are cell surface receptors as a result several diseases mediated by these integrin receptors, e.g., inflammatory diseases, autoimmune diseases, respiratory diseases, allergic diseases, fibrotic diseases, angiogenesis and cancers. Particularly arthritis, rheumatoid arthritis, osteoarthritis, sclerosis, multiple sclerosis, atherosclerosis, inflammatory bowel disease, Crohn's disease, ulcerative disease, asthma, asthma bronchitis, breast cancer, brain cancer, metastatic bone disease and other forms of metastasis.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A compound of Formula II:

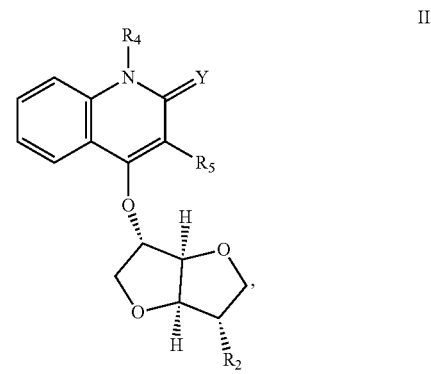

wherein:
  $R_2$ is hydrogen, hydroxyl, $C_1$-$C_{10}$ alkoxy, $C_2$-$C_6$ alkenyloxy, $C_1$-$C_{10}$ alkyl, $C_2$-$C_6$ alkenyl, $C_2$-$C_6$ alkynyl, —OC(O)($C_1$-$C_{10}$ alkyl), —OC(O)($C_1$-$C_{10}$ haloalkyl), or —OC(O)(aryl);
  $R_4$ is cyano, amino, $C_1$-$C_{10}$ aminoalkyl, $C_1$-$C_{10}$ alkyl, (aryl)alkyl, or aryl;
  $R_5$ is C(O)O$R^c$ or cyano;
  $R^c$ is hydrogen, $C_1$-$C_3$ alkyl, $CF_3$ or aryl;
  each aryl is independently phenyl or naphthyl;
  each alkyl, alkenyl, alkynyl, alkoxy, alkenoxy, phenyl, naphthyl, or aryl is independently optionally substituted with at least one substituent selected from the group consisting of halogen, hydroxyl, cyano, oxo, amino, $C_1$-$C_{10}$ aminoalkyl, $C_1$-$C_{10}$ aminoalkoxy, $C_1$-$C_{10}$ alkyl, $C_2$-$C_6$ alkenyl, $C_2$-$C_6$ alkynyl, $C_1$-$C_{10}$ alkoxy, $C_1$-$C_{10}$ hydroxyalkyl, (aryl)alkyl, aryloxy, (($C_1$-$C_{10}$ alkoxy)$C_1$-$C_{10}$ alkyl))amino, aryl, haloaryl, C(O)OC$_n$H$_{2n+1}$, —NR$^a$R$^b$, deuterium, and hydroxy aryl;
  $R^a$ is $C_1$-$C_{10}$ alkyl, $C_1$-$C_{10}$ alkoxy, or (aryl)alkyl;

$R^b$ is hydrogen or halogen;
Y is S or O; and
n is 0, 1, 2, or 3;
or a salt or tautomer thereof.

2. The compound of claim 1, wherein $R_4$ is selected from the group consisting of:

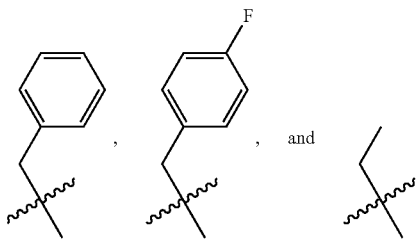

3. The compound of claim 1, wherein:
$R_4$ is $C_1$-$C_{10}$ alkyl(aryl);
$R_5$ is $C(O)OC_nH_{2n+1}$, and
n is 0, 1, 2, or 3.

4. The compound of claim 1, wherein $R_5$ is:

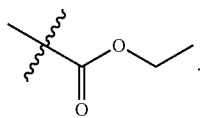 [SMILES: *C(=O)OCC]

5. A compound selected from the group consisting of:
Ethyl 4-[[(3S,3aR,6S,6aR)-3-hydroxy-2,3,3a,5,6,6a-hexahydrofuro[3,2-b]furan-6-yl]oxy]-1-ethyl-2-oxo-1,2-dihydroquinoline-3-carboxylate;
Ethyl 4-[[(3S,3aR,6S,6aR)-6-acetoxy-2,3,3a,5,6,6a-hexahydrofuro[3,2-b]furan-3-yl]oxy]-1-ethyl-2-oxo-1,2-dihydroquinoline-3-carboxylate;
Ethyl 4-[[(3S,3aR,6S,6aR)-6-(2-chloroacetyl)oxy-2,3,3a,5,6,6a-hexahydrofuro[3,2-b]furan-3-yl]oxy]-1-ethyl-2-oxo-1,2-dihydroquinoline-3-carboxylate;
Ethyl 4-[[(3S,3aS,6aR)-2,3,3a,6a-tetrahydrofuro[3,2-b]furan-3-yl]oxy]-1-ethyl-2-oxo-1,2-dihydroquinoline-3-carboxylate;
Ethyl 4-[[(3S,3aR,6S,6aR)-3-hydroxy-2,3,3a,5,6,6a-hexahydrofuro[3,2-b]furan-6-yl]oxy]-1-benzyl-2-oxo-1,2-dihydroquinoline-3-carboxylate;
Ethyl 4-[[(3S,3aR,6S,6aR)-6-acetoxy-2,3,3a,5,6,6a-hexahydrofuro[3,2-b]furan-3-yl]oxy]-1-benzyl-2-oxo-1,2-dihydroquinoline-3-carboxylate;
Ethyl 4-[[(3S,3aR,6S,6aR)-6-(2-chloroacetyl)oxy-2,3,3a,5,6,6a-hexahydrofuro[3,2-b]furan-3-yl]oxy]-1-benzyl-2-oxo-1,2-dihydroquinoline-3-carboxylate;
Ethyl 4-[[(3S,3aS,6aR)-2,3,3a,6a-tetrahydrofuro[3,2-b]furan-3-yl]oxy]-1-benzyl-2-oxo-1,2-dihydroquinoline-3-carboxylate;
Ethyl 4-[[(3S,3aR,6S,6aR)-3-hydroxy-2,3,3a,5,6,6a-hexahydrofuro[3,2-b]furan-6-yl]oxy]-1-[(4-fluorophenyl)methyl]-2-oxo-1,2-dihydroquinoline-3-carboxylate;
Ethyl 4-[[(3S,3aR,6S,6aR)-6-(2-chloroacetyl)oxy-2,3,3a,5,6,6a-hexahydrofuro[3,2-b]furan-3-yl]oxy]-1-[(4-fluorophenyl)methyl]-2-oxo-1,2-dihydroquinoline-3-carboxylate;
4-[[(3S,3aR,6S,6aR)-3-Hydroxy-2,3,3a,5,6,6a-hexahydrofuro[3,2-b]furan-6-yl]oxy]-1-benzyl-2-oxo-1,2-dihydroquinoline-3-carbonitrile;
[(3S,3aR,6S,6aR)-3-[(1-Benzyl-3-cyano-2-oxo-4-quinolyl)oxy]-2,3,3a,5,6,6a-hexahydrofuro[3,2-b]furan-6-yl]acetate;
[(3S,3aR,6S,6aR)-3-[(1-Benzyl-3-cyano-2-oxo-4-quinolyl)oxy]-2,3,3a,5,6,6a-hexahydrofuro[3,2-b]furan-6-yl]2-chloroacetate;
4-[[(3S,3aR,6S,6aR)-3-Hydroxy-2,3,3a,5,6,6a-hexahydrofuro[3,2-b]furan-6-yl]oxy]-1-[(4-fluorophenyl)methyl]-2-oxo-1,2-dihydroquinoline-3-carbonitrile;
[(3S,3aR,6S,6aR)-3-[[3-Cyano-1-[(4-fluorophenyl)methyl]-2-oxo-4-quinolyl]oxy]-2,3,3a,5,6,6a-hexahydrofuro[3,2-b]furan-6-yl]acetate;
[(3S,3aR,6S,6aR)-3-[[3-Cyano-1-[(4-fluorophenyl)methyl]-2-oxo-4-quinolyl]oxy]-2,3,3a,5,6,6a-hexahydrofuro[3,2-b]furan-6-yl]benzoate;
[(3S,3aR,6S,6aR)-3-[[3-Cyano-1-[(4-fluorophenyl)methyl]-2-oxo-4-quinolyl]oxy]-2,3,3a,5,6,6a-hexahydrofuro[3,2-b]furan-6-yl]2-chloroacetate;
4-[4-[[(3S,3aR,6S,6aR)-3-Hydroxy-2,3,3a,5,6,6a-hexahydrofuro[3,2-b]furan-6-yl]oxy]-3-chloro-anilino]-1-benzyl-2-oxo-1,2-dihydroquinoline-3-carbonitrile;
Ethyl 4-[4-[[(3S,3aR,6S,6aR)-3-hydroxy-2,3,3a,5,6,6a-hexahydrofuro[3,2-b]furan-6-yl]oxy]-3-chloro-anilino]-1-benzyl-2-oxo-1,2-dihydroquinoline-3-carboxylate;
[(3S,3aR,6S,6aR)-3-[4-[(6,7-Dimethoxyquinazolin-4-yl)amino]phenoxy]-2,3,3a,5,6,6a-hexahydrofuro[3,2-b]furan-6-yl]acetate;
N-[4-[[(3S,3aR,6S,6aR)-3-benzyloxy-2,3,3a,5,6,6a-hexahydrofuro[3,2-b]furan-6-yl]oxy]phenyl]-6,7-dimethoxy-quinazolin-4-amine;
N-[4-[[(3S,3aR,6S,6aR)-3-benzyloxy-2,3,3a,5,6,6a-hexahydrofuro[3,2-b]furan-6-yl]oxy]-3-chloro-phenyl]-6,7-dimethoxy-quinazolin-4-amine;
(3S,3aR,6S,6aR)-6-[2-Chloro-4-[(6,7-dimethoxyquinazolin-4-yl)amino]phenoxy]-2,3,3a,5,6,6a-hexahydrofuro[3,2-b]furan-3-ol;
[(3S,3aR,6S,6aR)-3-[2-Chloro-4-[(6,7-dimethoxyquinazolin-4-yl)amino]phenoxy]-2,3,3a,5,6,6a-hexahydrofuro[3,2-b]furan-6-yl]acetate;
[(3S,3aR,6S,6aR)-3-[2-Chloro-4-[(6,7-dimethoxyquinazolin-4-yl)amino]phenoxy]-2,3,3a,5,6,6a-hexahydrofuro[3,2-b]furan-6-yl]benzoate;
[(3S,3aR,6S,6aR)-3-[4-(Thieno[3,2-d]pyrimidin-4-ylamino)phenoxy]-2,3,3a,5,6,6a-hexahydrofuro[3,2-b]furan-6-yl]acetate;
(3S,3aR,6S,6aR)-6-[2-Chloro-4-(thieno[3,2-d]pyrimidin-4-ylamino)phenoxy]-2,3,3a,5,6,6a-hexahydrofuro[3,2-b]furan-3-ol;
[(3S,3aR,6S,6aR)-3-[2-Chloro-4-(thieno[3,2-d]pyrimidin-4-ylamino)phenoxy]-2,3,3a,5,6,6a-hexahydrofuro[3,2-b]furan-6-yl]acetate;
[(3S,3aR,6S,6aR)-3-[2-Chloro-4-(thieno[3,2-d]pyrimidin-4-ylamino)phenoxy]-2,3,3a,5,6,6a-hexahydrofuro[3,2-b]furan-6-yl]benzoate;
(3S,3aR,6S,6aR)-6-[2-Chloro-4-[(2-methylsulfanylpyrimidin-4-yl)amino]phenoxy]-2,3,3a,5,6,6a-hexahydrofuro[3,2-b]furan-3-ol;
[(3S,3aR,6S,6aR)-3-[2-[(1-Methylsulfonyl-4-piperidyl)amino]pyrimidin-4-yl]oxy-2,3,3a,5,6,6a-hexahydrofuro[3,2-b]furan-6-yl]acetate;
[(3S,3aR,6S,6aR)-3-[2-[(1-Tolylsulfonyl-4-piperidyl)amino]pyrimidin-4-yl]oxy-2,3,3a,5,6,6a-hexahydrofuro[3,2-b]furan-6-yl]acetate;
[(3S,3aR,6S,6aR)-3-[2-[[1-(2,2-Dimethylpropanoyl)-4-piperidyl]amino]pyrimidin-4-yl]oxy-2,3,3a,5,6,6a-hexahydrofuro[3,2-b]furan-6-yl]acetate;

[(3S,3aR,6S,6aR)-3-[2-[(4-Fluorophenyl)methylamino]pyrimidin-4-yl]oxy-2,3,3a,5,6,6a-hexahydrofuro[3,2-b]furan-6-yl]acetate;

[(3S,3aR,6S,6aR)-3-[2-[(1-Methylsulfonyl-4-piperidyl)amino]pyrimidin-4-yl]oxy-2,3,3a,5,6,6a-hexahydrofuro[3,2-b]furan-6-yl]benzoate;

[(3S,3aR,6S,6aR)-3-Acetoxy-2,3,3a,5,6,6a-hexahydrofuro[3,2-b]furan-6-yl]5-bromo-2-[(1-methylsulfonyl-4-piperidyl)amino]pyrimidine-4-carboxylate;

(3S,3aR,6S,6aR)-6-[4-[[2-[4-[[(3S,3aR,6S,6aR)-3-Hydroxy-2,3,3a,5,6,6a-hexahydrofuro[3,2-b]furan-6-yl]oxy]-3-chloro-anilino]pyrimidin-4-yl]amino]-2-chloro-phenoxy]-2,3,3a,5,6,6a-hexahydrofuro[3,2-b]furan-3-ol;

[(3S,3aR,6S,6aR)-3-Hydroxy-2,3,3a,5,6,6a-hexahydrofuro[3,2-b]furan-6-yl](2S)-2-[(2-chloro-6-methyl-benzoyl)amino]-3-[4-[(2,6-dichlorobenzoyl)amino]phenyl]propanoate;

[(3S,3aR,6S,6aR)-3-Acetoxy-2,3,3a,5,6,6a-hexahydrofuro[3,2-b]furan-6-yl](2S)-2-[(2-chloro-6-methyl-benzoyl)amino]-3-[4-[(2,6-dichlorobenzoyl)amino]phenyl]propanoate;

[(3S,3aR,6S,6aR)-3-Benzyloxy-2,3,3a,5,6,6a-hexahydrofuro[3,2-b]furan-6-yl](2S)-2-[(2-chloro-6-methyl-benzoyl)amino]-3-[4-[(2,6-dichlorobenzoyl)amino]phenyl]propanoate;

[(3S,3aR,6S,6aR)-3-Acetoxy-2,3,3a,5,6,6a-hexahydrofuro[3,2-b]furan-6-yl](2S)-2-[(2-chloro-6-methyl-benzoyl)amino]-3-[4-(1,3,4-trimethyl-2,6-dioxo-pyrimidin-5-yl)phenyl]propanoate;

[(3S,3aR,6S,6aR)-3-Hydroxy-2,3,3a,5,6,6a-hexahydrofuro[3,2-b]furan-6-yl](2S)-2-[(2-chloro-6-methyl-benzoyl)amino]-3-[4-(1,3,4-trimethyl-2,6-dioxo-pyrimidin-5-yl)phenyl]propanoate;

or a salt or tautomer thereof.

6. A pharmaceutical composition comprising at least one compound of claim 1, or a pharmaceutically acceptable salt or tautomer thereof, and at least one pharmaceutically acceptable carrier.

7. The pharmaceutical composition of claim 6, further comprising one or more additional therapeutic agents.

8. A pharmaceutical composition comprising at least one compound of claim 5, or a pharmaceutically acceptable salt or tautomer thereof, and at least one pharmaceutically acceptable carrier.

9. The pharmaceutical composition of claim 8, further comprising one or more additional therapeutic agents.

\* \* \* \* \*